US012478398B2

(12) United States Patent
Lazzari et al.

(10) Patent No.: US 12,478,398 B2
(45) Date of Patent: Nov. 25, 2025

(54) SURGICAL INSTRUMENT FOR ROBOTIC SURGERY

(71) Applicant: MEDICAL MICROINSTRUMENTS, INC., Wilmington, DE (US)

(72) Inventors: Giorgio Lazzari, Pisa (IT); Massimiliano Simi, Pisa (IT); Nicola Pineschi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 167 days.

(21) Appl. No.: 18/570,486

(22) PCT Filed: Jun. 16, 2022

(86) PCT No.: PCT/IB2022/055597
§ 371 (c)(1),
(2) Date: Dec. 14, 2023

(87) PCT Pub. No.: WO2022/269421
PCT Pub. Date: Dec. 29, 2022

(65) Prior Publication Data

US 2024/0285299 A1 Aug. 29, 2024

(30) Foreign Application Priority Data

Jun. 21, 2021 (IT) ........................ 102021000016154

(51) Int. Cl.
*A61B 17/295* (2006.01)
*A61B 34/37* (2016.01)
*A61B 17/00* (2006.01)

(52) U.S. Cl.
CPC ............ *A61B 17/295* (2013.01); *A61B 34/37* (2016.02); *A61B 2017/00353* (2013.01)

(58) Field of Classification Search
CPC .................. A61B 17/295; A61B 34/37; A61B 2017/00353
See application file for complete search history.

(56) References Cited

U.S. PATENT DOCUMENTS 5,254,129 A * 10/1993 Alexander ........... A61B 17/295 606/174
5,439,471 A * 8/1995 Kerr ................... A61B 17/0467 606/174

(Continued)

FOREIGN PATENT DOCUMENTS

DE 102010009065 A1 8/2011
DE 102014006264 A1 11/2015

(Continued)

OTHER PUBLICATIONS

International Search Report and Written Opinion issued for International Patent Appl. No. PCT/IB2022/055597 mailed Sep. 20, 2022, 11 pgs.

*Primary Examiner* — Phong Son H Dang
(74) *Attorney, Agent, or Firm* — Merchant & Gould P.C.

(57) ABSTRACT

A needle-holder/cutter type surgical instrument includes an articulated end-effector including a support structure including two prongs, a first tip link having an elongated body including an integral first proximal attachment root, a first distal free end and a first gripping surface therebetween. A second tip link has an elongated body including an integral second proximal attachment root, a second distal free end, and a second gripping surface therebetween. A blade link includes an integral third proximal attachment root, an elastically deformable bending body and a cutting edge. The blade link rotates with the first tip link. The first root, the second root, and the third root are arranged axially. A counter-blade surface rotates with the second tip link. The counter blade surface abuts against the cutting edge, bending (Continued)

the blade link axially, so the cutting edge and the counter-blade surface attain a mechanical interference contact to exert a cutting action.

14 Claims, 23 Drawing Sheets

(56) References Cited

U.S. PATENT DOCUMENTS 5,904,702 A * 5/1999 Ek .......................... A61B 17/29 606/208
6,063,095 A 5/2000 Wang et al.
6,206,877 B1 * 3/2001 Kese .................. A61B 18/1445 606/41
6,364,888 B1 4/2002 Niemeyer et al.
6,424,885 B1 7/2002 Niemeyer et al.
6,459,926 B1 10/2002 Nowlin et al.
6,554,844 B2 * 4/2003 Lee ...................... A61B 5/0084 606/1
6,594,552 B1 7/2003 Nowlin et al.
6,671,581 B2 12/2003 Niemeyer et al.
6,766,204 B2 7/2004 Niemeyer et al.
6,879,880 B2 4/2005 Nowlin et al.
7,087,049 B2 8/2006 Nowlin et al.
7,155,315 B2 12/2006 Niemeyer
7,331,967 B2 2/2008 Lee et al.
7,373,219 B2 5/2008 Nowlin et al.
7,686,804 B2 * 3/2010 Johnson ............. A61B 18/1445 606/51
7,778,733 B2 8/2010 Nowlin et al.
7,806,891 B2 10/2010 Nowlin et al.
7,886,743 B2 2/2011 Cooper et al.
7,947,050 B2 5/2011 Lee et al.
7,967,137 B2 6/2011 Fulbrook et al.
8,004,229 B2 8/2011 Nowlin et al.
8,005,571 B2 8/2011 Sutherland et al.
8,123,740 B2 2/2012 Madhani et al.
8,220,468 B2 7/2012 Cooper et al.
8,281,670 B2 10/2012 Larkin et al.
8,368,649 B2 2/2013 Hall
8,375,808 B2 2/2013 Blumenkranz et al.
8,521,331 B2 8/2013 Itkowitz
8,540,748 B2 9/2013 Murphy et al.
8,620,473 B2 12/2013 Diolaiti et al.
8,677,820 B2 3/2014 Nakagawa et al.
8,812,160 B2 8/2014 Hagn et al.
8,831,782 B2 9/2014 Itkowitz
8,935,003 B2 1/2015 Itkowitz et al.
8,939,963 B2 1/2015 Rogers et al.
8,996,173 B2 3/2015 Itkowitz et al.
9,060,796 B2 6/2015 Seo
9,101,379 B2 8/2015 Au et al.
9,333,042 B2 5/2016 Diolaiti et al.
9,408,668 B2 8/2016 Durant et al.
9,452,020 B2 9/2016 Griffiths et al.
9,492,927 B2 11/2016 Diolaiti et al.
9,554,866 B2 1/2017 Cunningham et al.
9,629,680 B2 4/2017 Winer
9,632,573 B2 4/2017 Ogawa et al.
9,743,989 B2 8/2017 Itkowitz et al.
9,770,300 B2 9/2017 Kwon et al.
9,901,402 B2 2/2018 Itkowitz et al.
9,949,799 B2 4/2018 Hingwe et al.
9,968,405 B2 5/2018 Cooper et al.
10,013,082 B2 7/2018 Schecter
10,034,718 B2 7/2018 Griffiths et al.
10,052,164 B2 8/2018 Overmyer
10,085,810 B2 10/2018 Vakharia et al.
10,123,844 B2 11/2018 Nowlin et al.
10,188,472 B2 1/2019 Diolaiti et al.
10,219,870 B2 3/2019 Mondry et al.
10,219,898 B2 3/2019 Forsell
10,271,915 B2 4/2019 Diolaiti et al.
10,292,661 B1 5/2019 LaBorde
10,299,873 B2 5/2019 Hares et al.
10,299,883 B2 5/2019 Kilroy et al.
10,307,199 B2 6/2019 Farritor et al.
10,321,964 B2 6/2019 Grover et al.
10,357,320 B2 7/2019 Beira
10,357,324 B2 7/2019 Flatt et al.
10,376,323 B2 8/2019 Farritor et al.
10,376,337 B2 8/2019 Kilroy et al.
10,383,699 B2 8/2019 Kilroy et al.
10,393,109 B2 8/2019 Wu et al.
10,413,374 B2 9/2019 Chassot et al.
10,420,618 B2 9/2019 Grover et al.
10,470,830 B2 11/2019 Hill et al.
10,485,621 B2 11/2019 Morrissette et al.
10,512,514 B2 12/2019 Nowlin et al.
10,512,515 B2 12/2019 Bailey
10,524,871 B2 1/2020 Liao
10,531,929 B2 1/2020 Widenhouse et al.
10,543,050 B2 1/2020 Itkowitz et al.
10,561,468 B2 2/2020 Cunningham et al.
10,568,703 B2 2/2020 Nobles et al.
10,568,704 B2 2/2020 Savall et al.
10,582,975 B2 3/2020 Simi
10,603,123 B2 3/2020 Vakharia et al.
10,617,484 B2 4/2020 Kilroy et al.
10,624,708 B2 4/2020 Hunter
10,639,114 B2 5/2020 Schuh et al.
10,653,489 B2 5/2020 Kopp
10,661,453 B2 5/2020 Koenig et al.
10,736,701 B2 8/2020 Savall et al.
10,736,706 B2 8/2020 Scheib
10,751,136 B2 8/2020 Farritor et al.
10,758,298 B2 9/2020 Felder et al.
10,779,898 B2 9/2020 Hill et al.
10,786,327 B2 9/2020 Anderson et al.
10,789,329 B2 9/2020 Lanting
10,813,713 B2 10/2020 Koch, Jr. et al.
10,820,953 B2 11/2020 Kralicky et al.
10,842,577 B2 11/2020 Kilroy et al.
10,842,581 B2 11/2020 Bailey
10,864,051 B2 12/2020 Simi
10,881,477 B1 1/2021 Genova et al.
10,888,390 B2 1/2021 Higuchi et al.
10,898,281 B2 1/2021 Cooper et al.
10,912,618 B2 2/2021 Vakharia et al.
10,959,798 B2 3/2021 Diolaiti et al.
10,987,192 B2 4/2021 Garcia Kilroy et al.
11,037,464 B2 6/2021 Ho et al.
11,045,268 B2 6/2021 Grover et al.
11,083,532 B2 8/2021 Liao
11,083,534 B2 8/2021 Hares
11,096,746 B2 8/2021 Savall et al.
11,109,925 B2 9/2021 Cooper et al.
11,135,031 B2 10/2021 Savall et al.
11,160,601 B2 * 11/2021 Worrell .............. A61B 18/1445
11,172,997 B2 11/2021 Kostrzewski et al.
11,179,209 B2 11/2021 Kralicky et al.
11,179,211 B2 11/2021 Zemlok et al.
11,213,364 B2 1/2022 Popovic
11,246,670 B2 2/2022 Swayze et al.
11,266,469 B2 3/2022 Fuerst et al.
11,284,957 B2 3/2022 Denlinger et al.
11,284,959 B2 3/2022 Bailey
11,344,374 B2 5/2022 Tekiela et al.
11,357,597 B2 6/2022 Jhaveri et al.
11,399,908 B2 8/2022 Diolaiti et al.
11,406,465 B2 8/2022 Zemlok et al.
11,417,928 B2 8/2022 Cheng
11,439,478 B2 9/2022 Anderson et al.
11,446,097 B2 9/2022 Savall et al.
11,457,987 B2 10/2022 He et al.
11,478,318 B2 10/2022 Cone et al.
11,484,379 B2 11/2022 Sutherland et al.
11,504,197 B1 11/2022 Noonan et al.
11,504,203 B2 11/2022 Flatt et al.
11,534,246 B2 12/2022 Fuerst et al.
11,534,252 B2 12/2022 DiMaio et al.
11,576,733 B2 2/2023 Anglese
11,607,279 B2 3/2023 Chaplin

(56) References Cited

U.S. PATENT DOCUMENTS

| | | | |
|---|---|---|---|
| 11,666,401 B2 | 6/2023 | Denlinger et al. | |
| 11,684,434 B2 | 6/2023 | Shelton, IV | |
| 2002/0055795 A1 | 5/2002 | Niemeyer et al. | |
| 2002/0128552 A1 | 9/2002 | Nowlin et al. | |
| 2003/0004610 A1 | 1/2003 | Niemeyer et al. | |
| 2003/0195664 A1 | 10/2003 | Nowlin et al. | |
| 2004/0039485 A1 | 2/2004 | Niemeyer et al. | |
| 2005/0194507 A1 | 9/2005 | White | |
| 2006/0030840 A1 | 2/2006 | Nowlin et al. | |
| 2006/0106493 A1 | 5/2006 | Niemeyer et al. | |
| 2006/0241414 A1 | 10/2006 | Nowlin et al. | |
| 2007/0244515 A1* | 10/2007 | Fanous | A61B 17/295 606/174 |
| 2008/0154246 A1 | 6/2008 | Nowlin et al. | |
| 2009/0301927 A1 | 12/2009 | Fvlbrook et al. | |
| 2010/0053085 A1 | 3/2010 | Hall | |
| 2010/0274087 A1 | 10/2010 | Diolaiti et al. | |
| 2010/0298638 A1* | 11/2010 | Slater | A61B 17/295 600/106 |
| 2010/0298853 A1* | 11/2010 | Slater | A61B 17/29 606/170 |
| 2011/0118748 A1 | 5/2011 | Itkowitz | |
| 2012/0011932 A1 | 1/2012 | Nakagawa et al. | |
| 2012/0059391 A1 | 3/2012 | Diolaiti et al. | |
| 2012/0071891 A1 | 3/2012 | Itkowitz et al. | |
| 2012/0071892 A1 | 3/2012 | Itkowitz et al. | |
| 2013/0035697 A1 | 2/2013 | Ogawa et al. | |
| 2013/0316681 A1 | 11/2013 | Huang et al. | |
| 2013/0321262 A1 | 12/2013 | Schecter | |
| 2014/0018960 A1 | 1/2014 | Itkowitz | |
| 2014/0222021 A1 | 8/2014 | Diolaiti et al. | |
| 2015/0025549 A1 | 1/2015 | Kilroy et al. | |
| 2015/0038981 A1 | 2/2015 | Kilroy et al. | |
| 2015/0038982 A1 | 2/2015 | Kilroy et al. | |
| 2015/0066051 A1 | 3/2015 | Kwon et al. | |
| 2015/0080909 A1 | 3/2015 | Itkowitz et al. | |
| 2015/0157410 A1 | 6/2015 | Kilroy et al. | |
| 2015/0182289 A1 | 7/2015 | Itkowitz et al. | |
| 2016/0242860 A1 | 8/2016 | Diolaiti et al. | |
| 2017/0035521 A1 | 2/2017 | Diolaiti et al. | |
| 2017/0095295 A1 | 4/2017 | Overmyer | |
| 2017/0095298 A1 | 4/2017 | Vakharia et al. | |
| 2017/0224428 A1 | 8/2017 | Kopp | |
| 2017/0252112 A1 | 9/2017 | Crawford et al. | |
| 2017/0265949 A1 | 9/2017 | Crawford et al. | |
| 2017/0312043 A1 | 11/2017 | Ogawa et al. | |
| 2017/0319284 A1 | 11/2017 | Itkowitz et al. | |
| 2018/0025666 A1 | 1/2018 | Ho et al. | |
| 2018/0036088 A1 | 2/2018 | Kilroy et al. | |
| 2018/0078034 A1 | 3/2018 | Savall et al. | |
| 2018/0078319 A1 | 3/2018 | Nobles et al. | |
| 2018/0078321 A1 | 3/2018 | Liao | |
| 2018/0092706 A1 | 4/2018 | Anderson et al. | |
| 2018/0161108 A1 | 6/2018 | Savall et al. | |
| 2018/0168759 A1 | 6/2018 | Kilroy et al. | |
| 2019/0012006 A1 | 1/2019 | Schecter | |
| 2019/0029770 A1 | 1/2019 | Bailey | |
| 2019/0069960 A1 | 3/2019 | Vakharia et al. | |
| 2019/0105032 A1 | 4/2019 | Crews | |
| 2019/0110847 A1 | 4/2019 | Diolaiti et al. | |
| 2019/0201152 A1 | 7/2019 | Diolaiti et al. | |
| 2019/0239972 A1 | 8/2019 | Chassot et al. | |
| 2019/0298465 A1 | 10/2019 | Chin | |
| 2019/0307524 A1 | 10/2019 | Popovic | |
| 2019/0314097 A1 | 10/2019 | Diolaiti | |
| 2019/0336156 A1* | 11/2019 | Hammerland, III | A61B 17/295 |
| 2019/0336157 A1* | 11/2019 | Ahrens | A61B 17/1606 |
| 2019/0343594 A1 | 11/2019 | Garcia Kilroy et al. | |
| 2019/0380791 A1 | 12/2019 | Fuerst et al. | |
| 2019/0380802 A1 | 12/2019 | Savall et al. | |
| 2019/0380809 A1 | 12/2019 | Fuerst et al. | |
| 2020/0008901 A1 | 1/2020 | Garcia Kilroy et al. | |
| 2020/0022775 A1 | 1/2020 | Garcia Kilroy et al. | |
| 2020/0046439 A1 | 2/2020 | Tekiela et al. | |
| 2020/0046450 A1 | 2/2020 | Tsao et al. | |
| 2020/0069388 A1 | 3/2020 | Bailey | |
| 2020/0085522 A1 | 3/2020 | Liao | |
| 2020/0107894 A1 | 4/2020 | Wallace | |
| 2020/0113641 A1 | 4/2020 | Itkowitz et al. | |
| 2020/0138534 A1 | 5/2020 | Garcia Kilroy et al. | |
| 2020/0170726 A1 | 6/2020 | Simi | |
| 2020/0170727 A1 | 6/2020 | Simi | |
| 2020/0197112 A1 | 6/2020 | Chin et al. | |
| 2020/0197115 A1 | 6/2020 | Vakharia et al. | |
| 2020/0205922 A1 | 7/2020 | Cone et al. | |
| 2020/0214773 A1 | 7/2020 | Nobles et al. | |
| 2020/0214779 A1 | 7/2020 | Masuda et al. | |
| 2020/0222134 A1 | 7/2020 | Savall et al. | |
| 2020/0289212 A1 | 9/2020 | Savall et al. | |
| 2020/0289223 A1 | 9/2020 | Denlinger et al. | |
| 2020/0330170 A1 | 10/2020 | Farritor et al. | |
| 2020/0360097 A1 | 11/2020 | DiMaio et al. | |
| 2020/0390510 A1 | 12/2020 | Thompson et al. | |
| 2020/0397517 A1 | 12/2020 | Unsworth | |
| 2020/0397529 A1 | 12/2020 | Anderson et al. | |
| 2020/0405408 A1 | 12/2020 | Shelton, IV et al. | |
| 2020/0405434 A1 | 12/2020 | Schuh et al. | |
| 2021/0030495 A1 | 2/2021 | Savall et al. | |
| 2021/0052338 A1 | 2/2021 | Hill et al. | |
| 2021/0052341 A1 | 2/2021 | Bailey | |
| 2021/0059776 A1 | 3/2021 | Simi | |
| 2021/0059781 A1 | 3/2021 | Peine et al. | |
| 2021/0085301 A1 | 3/2021 | Au et al. | |
| 2021/0106393 A1 | 4/2021 | Simi | |
| 2021/0121260 A1 | 4/2021 | Genova et al. | |
| 2021/0153964 A1 | 5/2021 | Diolaiti et al. | |
| 2021/0153965 A1 | 5/2021 | Lau et al. | |
| 2021/0153966 A1 | 5/2021 | Lau et al. | |
| 2021/0196411 A1 | 7/2021 | Vakharia et al. | |
| 2021/0196413 A1 | 7/2021 | Inoue | |
| 2021/0197401 A1 | 7/2021 | Weintraub et al. | |
| 2021/0290326 A1 | 9/2021 | Diolaiti et al. | |
| 2021/0290328 A1 | 9/2021 | Miller et al. | |
| 2021/0304639 A1 | 9/2021 | Ho et al. | |
| 2021/0322117 A1 | 10/2021 | Liao | |
| 2021/0322119 A1 | 10/2021 | Hares | |
| 2021/0353381 A1 | 11/2021 | Usui et al. | |
| 2021/0369365 A1 | 12/2021 | Goswami et al. | |
| 2022/0015839 A1 | 1/2022 | Savall et al. | |
| 2022/0015852 A1 | 1/2022 | Savall et al. | |
| 2022/0031415 A1 | 2/2022 | Vargas et al. | |
| 2022/0047345 A1 | 2/2022 | Choi et al. | |
| 2022/0054193 A1* | 2/2022 | Perets | A61B 18/22 |
| 2022/0096189 A1 | 3/2022 | Popovic | |
| 2022/0184823 A1 | 6/2022 | Bonny et al. | |
| 2022/0192763 A1 | 6/2022 | Fuerst et al. | |
| 2022/0211452 A1 | 7/2022 | Clark et al. | |
| 2022/0218418 A1 | 7/2022 | Jolaeimoghaddam et al. | |
| 2022/0226056 A1 | 7/2022 | Beckman et al. | |
| 2022/0265380 A1 | 8/2022 | Bailey | |
| 2022/0361736 A1 | 11/2022 | Danna et al. | |
| 2022/0361970 A1 | 11/2022 | Griffiths et al. | |
| 2022/0370163 A1 | 11/2022 | Schuh et al. | |
| 2022/0378526 A1 | 12/2022 | Balicki et al. | |
| 2022/0378527 A1 | 12/2022 | Basafa et al. | |
| 2022/0378533 A1 | 12/2022 | McDiarmid et al. | |
| 2022/0387131 A1 | 12/2022 | Anderson et al. | |
| 2022/0395346 A1 | 12/2022 | Ihara et al. | |
| 2022/0401162 A1 | 12/2022 | Unsworth | |
| 2023/0028689 A1 | 1/2023 | Rabindran et al. | |
| 2023/0045591 A1 | 2/2023 | de la Fuente Klein et al. | |
| 2023/0149105 A1 | 5/2023 | Thornycroft et al. | |

FOREIGN PATENT DOCUMENTS

| | | | |
|---|---|---|---|
| EP | 2845556 | A1 | 3/2015 |
| EP | 3245975 | A1 | 11/2017 |
| EP | 3424651 | A1 | 1/2019 |
| EP | 3459429 | A1 | 3/2019 |
| EP | 3574860 | A1 | 12/2019 |
| EP | 3586780 | A1 | 1/2020 |
| EP | 3852668 | A1 | 7/2021 |
| WO | 2013071071 | A1 | 5/2013 |

(56) References Cited

FOREIGN PATENT DOCUMENTS

| | | | |
|---|---|---|---|
| WO | 2014151621 | A1 | 9/2014 |
| WO | 2016053657 | A1 | 4/2016 |
| WO | 2016171757 | A1 | 10/2016 |
| WO | 2016201207 | A1 | 12/2016 |
| WO | 2017-064301 | A1 | 4/2017 |
| WO | 2017-064303 | A1 | 4/2017 |
| WO | 2017-064306 | A1 | 4/2017 |
| WO | 2017094844 | A1 | 6/2017 |
| WO | 2018104252 | A1 | 6/2018 |
| WO | 2018107062 | A1 | 6/2018 |
| WO | 2018-189721 | A1 | 10/2018 |
| WO | 2018-189722 | A1 | 10/2018 |
| WO | 2018-189729 | A1 | 10/2018 |
| WO | 2019050878 | A2 | 3/2019 |
| WO | 2019099584 | A1 | 5/2019 |
| WO | 2019103954 | A1 | 5/2019 |
| WO | 2019-220407 | A1 | 11/2019 |
| WO | 2019-220408 | A1 | 11/2019 |
| WO | 2019-220409 | A1 | 11/2019 |
| WO | 2019240825 | A1 | 12/2019 |
| WO | 2020139405 | A1 | 7/2020 |
| WO | 2020153411 | A1 | 7/2020 |
| WO | 2021141920 | A1 | 7/2021 |
| WO | 2021188127 | A1 | 9/2021 |
| WO | 2022155067 | A1 | 7/2022 |

* cited by examiner

SURGICAL INSTRUMENT FOR ROBOTIC SURGERY

CROSS-REFERENCE TO RELATED APPLICATIONS

This application is a National Stage Application of PCT/IB2022/055597, filed Jun. 16, 2022, which claims benefit of priority to application No. 102021000016154, filed Jun. 21, 2021 in Italy, and which applications are incorporated herein by reference. To the extent appropriate, a claim of priority is made to each of the above-disclosed applications.

FIELD OF THE INVENTION

The present invention relates to a surgical instrument of the needle-holder/cutter type.

The surgical instrument of the needle-holder/cutter type according to the invention is particularly suitable for applications in robotic teleoperated micro-surgery.

The present invention further relates to a robotic surgery system comprising at least one surgical instrument of the needle-holder/cutter type.

Background Art

Robotic surgery apparatuses are generally known in the art and typically comprise a central robotic tower (or cart) and one or more robotic arms extending from the central robotic tower. Each arm comprises a motorized positioning system (or manipulator) for moving a surgical instrument distally attachable thereto, in order to perform surgical procedures on a patient. The patient typically lies on an operating bed located in the operating room, in which sterility is ensured to avoid bacterial contamination due to non-sterile parts of the robotic apparatus.

In the context of traditional, i.e., non-robotic, surgery, instruments of the needle-holder/cutter type are generally known, which typically comprise at the opposite end of the maneuvering rings a needle-holder/cutter formed by the two free ends having gripping surfaces for the surgical needle and blades for cutting the suture. In some cases, the blades are made in a seat or recess made in the body of the gripper that is accessible through a distinct and separate access opening with respect to the opening for accessing the gripping surfaces for the needle.

Furthermore, in the field of robotic surgery, end-effector solutions of the needle-holder/cutter type for laparoscopy have been suggested placed at the distal end of an elongated shaft.

As shown for example in US-2019-298465, typically, the blade is co-molded with the respective gripping surface for the needle forming a cantilevered protrusion with respect to the gripping surface and placed proximally thereto, i.e., between the gripping surface and the articulation hinge of the gripping surfaces. Therefore, a single molded piece usually comprises a root for forming a part of the hinge, a free end, a gripping surface and a blade which extends with respect to the gripping surface in the closing direction towards the opposite and faceable other blade of the end-effector.

At the hinge, a single washer or a plurality of elastic washers of the “Belleville washer” type ensure an elastic preload between the roots of the two pieces forming the end-effector of the needle-holder/cutter type to determine in closing a mechanical interference condition between the blades aimed at making the cut. Therefore, when the end-effector closes, the opposite blades enter interference in a point and cause a transverse sliding away between the respective roots, counteracting the elastic influence action exerted by said elastic Belleville washers to the hinge.

Otherwise, US-2019-0105032 shows a cutting end-effector, in which the blades each comprise in a single piece an elastic cantilevered tab, said two elastic cantilevered tabs extending in a direction parallel to the pin towards each other, so that the elastic preload is given by the contact between the two cantilevered tabs. Thereby, assembling Belleville-type elastic washers on the hinge is avoided, thus allowing an axial space to be left at the hinge between the two blades to accommodate the sliding thereof relative to the variation of the elastic reaction exerted by the cantilevered elastic tabs thereof in mutual contact.

Alternatively, or in addition to the plurality of washers of the “Belleville washer” type, an adjustment screw can be provided at the hinge, usually forming an articulation pin itself, in order to adjust the cutting interference between the blades. If the adjustment screw is provided in combination with the plurality of elastic washers of the “Belleville washer” type, it works by counteracting the elastic action of the springs to allow an end of adjustment in elastic preload.

Usually, the known solutions suggest incorporating further functionalities in the same end-effector, such as electro-thermal-cauterizing treatment capacity by virtue of the provision of electrodes placed on the gripping surfaces. For example, the blades of the needle-holder/cutter instrument can be made in a single piece co-molded with the respective free ends and the gripping surfaces of the end-effector, and comprise electrical connections which make electro-cauterizing electrodes on the gripping surfaces themselves.

Another known example is given by US-2020-0107894 which shows a needle-holder/cutter solution in which the blade is housed in a longitudinal pocket of the gripping link and is rotatable independently with respect thereto, so that it can be extracted if necessary.

The miniaturization of surgical instruments and in particular of the ends or end-effectors thereof for robotic surgery is particularly desirable because it opens up advantageous scenarios of minimal invasiveness for the patient undergoing surgery to the manipulation and treatment capacity of millimeter and sub-millimeter tissues.

The known solutions of the type mentioned above are totally unsuitable for a boosted miniaturization because they would impose impossible processes for the production of the pieces as well as complicated assembly strategies of the pieces to obtain the assembled end-effector. For example, consider the need to assemble micro-parts to the hinge while counteracting the elastic reaction of Belleville-type elastic washers, as well as the objective extreme difficulty of manufacturing by co-molding micro-ridges and micro-undercuts which must be sufficiently robust to withstand rather high stresses when in operation and at the same time geometrically shaped to minimize frictions. In fact, as is well known, at the micro-scale surface forces such as friction are dominant over volume forces.

In addition to the difficulties of making micro-ridges, micro-grooves and undercut micro-machining, the elastic cantilevered tabs obtained in the body of the blades described above with reference to a known solution are also extremely difficult to cut and shape at the micro-scale in a precise and repeatable manner.

Furthermore, as the scale decreases, it becomes increasingly complex to precisely size elements intended to form when rotational joints are assembled, such as end-effector gripping terminals of a surgical instrument, because small machining uncertainties at the level of the fulcrum impose enormous inaccuracies next to the respective cantilevered free ends placed in a distal direction with respect to the rotational joint which are typically responsible for very delicate micro-manipulation operations of surgical needles, suture wires as well as anatomical parts of the patient undergoing surgery.

In an attempt to transmit a high closing force such as to exert a precise cutting action without damaging the actuation tendons, the provision of leverages associated with the blades (a solution in itself known in the art) would also be an obstacle to miniaturization, even for the sole objective difficulty of making the pieces on such a small scale that they simultaneously prove robust when in working conditions, as well as for the footprints in the area proximal to the common rotation axis of the free ends, as well as for the difficulty of assembly.

The end-effector portions which are placed distally with respect to the hinge, i.e., the cutting blades and gripping surfaces, are typically designed to perform extremely precise tasks and at the same time the cutting blades must ensure a precise and clean cutting action.

U.S. Ser. No. 10/864,051, WO-2017-064301, WO-2019-220407, WO-2019-220408, WO-2019-220409 and US-2021-059776 to the same Applicant disclose teleoperated robotic surgery systems having one or more surgical instruments controlled by one or more master interfaces. Furthermore, U.S. Ser. No. 10/582,975, EP-3586780, WO-2017-064303, WO-2018-189721, WO-2018-189729, US-2020-0170727 and US-2020-0170726 to the same Applicant disclose various embodiments of surgical instruments suitable for robotic surgery and microsurgery. These types of surgical instruments typically comprise a proximal interface portion having an interface intended to be driven by a robotic manipulator, a shaft, and an articulated cuff at the distal end of the shaft. The articulated cuff consists of a plurality of links moved by a plurality of tendons (or actuation cables). Two end tip links have a free end and a degree of freedom of opening/closing therebetween and can be adapted to handle a needle as well as a suture wire forming an end-effector of the needle-holder gripper type for teleoperated robotic surgery to perform anastomosis or other surgical therapies.

For example, WO-2017-064306 to same Applicant shows a surgical instrument in which the tendons for actuating the degree of freedom of opening/closing of the articulated end-effector slide on convex ruled sliding surfaces of the end-effector links, simultaneously avoiding routing the tendons inside guide grooves or channels with concave section. Thereby, the cross-section of the sliding contact portion between the tendons and the link is minimized, thus reducing the sliding friction and allowing a boosted miniaturization of the articulated end-effector while ensuring a high dexterity given by the end-effector joints, such as rotational joints of pitch and yaw.

Furthermore, WO-2018-189722 to same applicant discloses a surgical instrument in which the tendons for actuating the degree of freedom of opening/closing of the articulated end-effector, in addition to sliding on convex ruled sliding surfaces of the end-effector links, similar to what was previously discussed, are wound on said convex ruled sliding surfaces, describing arcuate paths which underlie a particularly high winding angle. In fact, by virtue of the low sliding friction of the tendons, they are capable of remaining in contact with the convex ruled surface of a link for a relatively long and arcuate longitudinal section.

In addition, US-2021-0106393 to the same applicant discloses some embodiments of a tendon consisting of intertwined polymer fibers. The use of polymer tendons allows reducing the sliding friction with respect to the use of metal tendons and at the same time an adequate dimensioning of the tendon allows traveling winding longitudinal paths in the articulated end-effector.

Therefore, the need is strongly felt to provide a surgical instrument solution of the needle-holder/cutter type which is suitable for extreme miniaturization and at the same time robust, reliable and capable of providing a precise and repeatable cutting action.

Furthermore, the need is felt to suggest a surgical instrument solution of the needle-holder/cutter type for teleoperated robotic micro-surgery which is simple to assemble and to build as well as reliable and precise and robust when under operating conditions, is adapted to allow a desired and controlled spatial orientation of the cutting action with respect to, for example, the main longitudinal extension direction of the surgical instrument body which can be useful to facilitate the observation of the surgery.

The need is felt to suggest a solution which allows assembling an articulated tip micro-instrument provided with grip and scissors and which consists of the smallest number of components so that it can be assembled easily and in a cost-affordable manner without imposing a small dexterity of the articulated end-effector.

The need is felt to suggest a solution which allows making micromechanical parts and in particular sharpened micromechanical parts with a high geometric precision and repeatability for the formation of an articulated tip micro-instrument provided with grip and scissors.

Solution

It is an object of the present invention to obviate the drawbacks complained of with reference to the background art.

This and other objects are achieved by a surgical instrument of the needle-holder/cutter type.

According to an aspect of the invention, a surgical instrument of the needle-holder/cutter type for a robotic surgery system comprises a articulated end-effector comprising a support structure comprising two prongs, a first tip link having an elongated body comprising in a single piece a first proximal attachment root, a first distal free end and a first gripping surface therebetween, and a second tip link having an elongated body comprising in a single piece a second proximal attachment root, a second distal free end, and a second gripping surface therebetween.

The articulated end-effector further comprises a blade link comprising in a single piece a third proximal attachment root, an elastically deformable bending body and a cutting edge.

The blade link is integral in rotation with said first tip link, which acts as a blade holder link. A drag engagement can be provided between the blade link and the first tip link which can be arranged distally with respect to the cutting edge.

Furthermore, a counter-blade surface is provided which is integral in rotation with the second tip link which therefore acts as a reaction link. A further counter-blade link having a counter-blade link root can be provided.

The counter-blade surface is adapted to abut against said cutting edge of the blade link, elastically bending said blade link axially, so that said cutting edge of the blade link and said counter-blade surface reach a mechanical interference contact condition to exert a cutting action.

The counter-blade can be sharp and comprise a cutting edge.

The support structure, the first tip link, the second tip link and the blade link are separate pieces articulated to one another in a common rotation axis defining an axial direction coincident with or parallel to the common rotation axis.

The roots are axially next to each o and are articulated with respect to the prongs of the support structure, defining a rotational joint of a cutting joint. Said rotational joint can be a rigid rotational joint in the axial direction, in which no elastic elements are provided in the coupling and the elasticity is provided distally with respect to the rotational joint, i.e., on the blade of the blade link.

The support structure can belong to a support link which is made in a single piece.

The support structure can be made in a single piece with a distal end of a rod or shaft of the surgical instrument.

According to an embodiment, the roots are overall interposed in a pack between said two prongs of the support structure and in direct and intimate contact therewith, to provide a reaction to the elastic bending of the blade of the blade link during the cutting action and no preload elastic elements are provided in the axial direction, nor adjustment screws. Said first, second and third root and said prongs of the support structure can comprise respective contact surfaces mutually contacting two by two, which are axially facing and are all parallel to one another.

According to an embodiment, the third root of the blade link is axially interposed between said first root of the first tip link and said second root of the second tip link and in direct and intimate contact therewith to provide a reaction to the elastic bending of the blade of the blade link during the cutting action. A definable axial distance between the prongs can remain constant for any cutting condition. The first attachment root can comprise a first surface facing axially outwards, and the second root can comprise a second surface facing axially outwards, and in which a further distance in the axial direction can be identified between said first surface and said second surface which is constant for any cutting condition.

According to an embodiment, the roots each comprise a through hole, and the through holes can all be in axis to receive an articulation pin.

The counter-blade surface integral in rotation with said second tip link can be made protruding axially to bend the blade link during the movement of the degree of freedom of opening/closing.

According to an embodiment, the counter-blade surface is a curved protruding surface having a concavity facing axially inwards.

According to an embodiment, the blade link body is substantially planar when in non-deformed configuration and lying on a definable lying plane; in which preferably an axially-facing blade surface of the blade link is parallel and aligned with a contact surface of the third root of the blade link in direct and intimate contact with the second root of the second tip link.

The first tip link can define with a portion thereof an axial deformation seat extending axially to receive the elastic bending of the blade of the blade link during the cutting action. According to an embodiment, the axial deformation seat is axially delimited by a surface of the first tip link facing axially inwards which is preferably parallel to the counter-blade surface.

According to an embodiment, the second tip is provided with a thread-stop recess for receiving a suture wire, in order to keep the suture wire in contact with the cutting edge of the blade of the blade link during a cutting closure.

According to an embodiment, the first root of the first tip link comprises in a single piece at least a first termination seat for at least one actuation tendon of the first tip link about said common rotation axis, and the second root of the second tip link comprises in a single piece at least a second termination seat for at least one actuation tendon of the second tip link about said common rotation axis.

The support structure comprising said two prongs can belong to a support link articulated with respect to a distal end of a shaft about a proximal rotation axis and comprises in a single piece at least a third termination seat for at least one actuation tendon of the support link about said proximal rotation axis.

The support link can further comprise in a single piece one or more convex ruled sliding surfaces for the actuation tendons of the first tip link and second tip link.

Preferably, an axial distance definable between a surface of said one or more convex ruled sliding surfaces of the support link and a termination seat between said termination seats of the first root or the second root remains constant in any cutting condition and preferably also gripping condition.

According to an embodiment, the axial elasticity necessary to perform the cutting action is provided by the blade portion and axially the roots are packed with the support structure, making a reaction to the elastic bending of the blade, preventing axial displacements from occurring between the roots.

The body of the counter-blade portion of the second tip can be elastically bendable in the axial direction, preferably axially outwards. Thereby, the axial elasticity necessary to perform the cutting action is provided by the blade portion and the counter-blade portion, jointly or separately for example depending on the opening angle of the tips.

According to an embodiment, a first pair of antagonistic tendons is connected to the first attachment root, for example the blade holder link root, to move the cutting edge about said common distal rotation axis, and a second pair of antagonistic tendons is connected to the second root to move the counter-blade portion about said common distal rotation axis.

According to an embodiment, the first attachment root, for example the blade holder link root, comprises in a single piece at least a first termination seat which receives said first pair of antagonistic tendons and the second attachment root comprises in a single piece at least a second termination seat which receives said second pair of antagonistic tendons.

The first pair of antagonistic tendons and the second pair of antagonistic tendons are adapted to slide longitudinally on said one or more convex ruled surfaces of the connection link if provided and on said one or more convex ruled surfaces of the support link and are adapted to wind/unwind without sliding on the respective convex ruled surface of the blade holder link root, i.e., the first root or the reaction link, i.e., the second root, to move the blade link and the counter-blade portion in opening/closing, respectively.

In accordance with an embodiment, a first cantilevered drag leg extends from the first root forming a free end of the first leg, axially delimiting said first termination seat, and a second cantilevered drag leg extends from the second root forming a free end of the second leg, axially delimiting said second termination seat, said first and second cantilevered legs each comprising abutment and drag walls placed as an undercut with respect to the respective termination seats acting as dragging abutments for the respective tendon termination. In such a case, it is possible to identify a first distance in an axial direction between the first cantilevered leg and a surface of said one or more convex ruled surfaces of the support structure, for example of the support link, is constant for any cutting condition and a second distance in a direction parallel to the common distal rotation axis between the second cantilevered leg and a surface of said one or more convex ruled surfaces of the support structure, for example of the support link, is constant for any cutting condition.

The first distance and the second distance can be mutually equal.

The first distance and/or the second distance can be zero.

According to an embodiment, the overall sliding friction force exchanged between each tendon and all the ruled surfaces of the links on which the tendon slides, when in operating conditions, is much less than the tensile force transmitted by the same tendon to achieve the elastic bending deformation of the blade portion when the degree of freedom of opening/closing is moved in closing to exert a cutting action. In other words, said sliding friction force of the tendons can be much less than the mechanical interference contact friction force between the blade and the counter-blade. For this purpose, the tendons can be made of polymer material, and the links can be made of metallic material, and the convex ruled surfaces with parallel generatrices of the links can be smooth, to reduce the longitudinal sliding friction of the tendons on the links. For example, the ruled surfaces of the links are obtained by wire electro-erosion.

Preferably, all the convex ruled surfaces of the connection link, the support link, the pulley portion of the first root and the pulley portion of the second root lack longitudinal channels. Therefore, the actuation tendons do not slide inside concave channels.

A third pair of antagonistic tendons can be provided for moving the support link about said common proximal rotation axis with respect to the connection link, the support link comprising at least a third termination seat which receives the tendon terminations of said third pair of antagonistic tendons. Preferably, the actuation tendons of the support link of said third pair of antagonistic tendons wind/unwind without sliding longitudinally on said one or more convex ruled surfaces of the support link, which therefore act as pulley surfaces for the actuation tendons of the third pair of antagonistic tendons.

According to an aspect of the invention, a rotational joint of a cutting joint of a surgical instrument of the needle-holder/cutter type is provided.

According to an aspect of the invention, a robotic surgery system comprising at least one surgical instrument of the needle-holder/cutter type is provided.

BRIEF DESCRIPTION OF THE DRAWINGS

Further features and advantages of the surgical instrument of the needle-holder/cutter type will appear from the following description of preferred embodiments, given as an indication and not as limitation, with reference to the accompanying drawings (it should be noted that references to "an" embodiment in this disclosure do not necessarily refer to the same embodiment, and are to be understood as at least one, furthermore, for the purposes of conciseness and reduction of the total number of drawings, a certain drawing can be used to show the features of more than one embodiment, and not all elements of the drawing may be necessary for a certain embodiment), in which.

DETAILED DESCRIPTION OF SOME EMBODIMENTS

Reference throughout this description to "an embodiment" is meant to indicate that a particular feature, structure or function described in relation to the embodiment is included in at least one embodiment of the present invention. Therefore, the formulations "in an embodiment" in various parts of this description do not necessarily require that they all refer to the same embodiment. Furthermore, particular features, structures or functions such as those shown in different drawings can be combined in any suitable manner in one or more embodiments, unless expressly specified otherwise.

In accordance with a general embodiment, a surgical instrument 1 is provided. Said surgical instrument 1 is a surgical instrument of the needle-holder/cutter type 1 (or "needle-driver/suture-cutter" according to a commonly used terminology).

Figure 1:
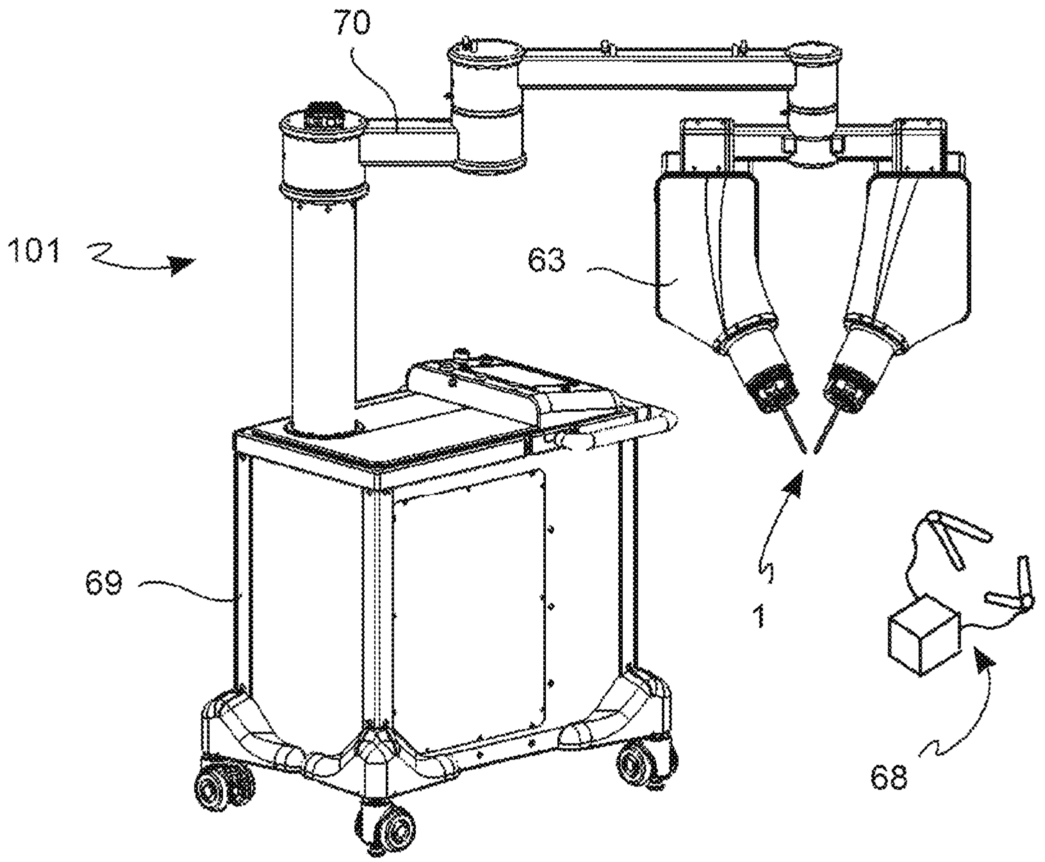
FIG. 1 shows an axonometric view of a robotic surgery system, according to an embodiment.

Said surgical instrument 1 of the needle-holder/cutter type is particularly suitable, but not uniquely intended, for robotic surgery and can be connectable to a robotic manipulator 63 comprising motorized actuators of a robotic surgery system 101, as shown in FIG. 1, for example. For example, said surgical instrument 1 of the needle-holder/cutter type can be associated with a mechanical and manual control and actuation device.

The robotic surgery system 101 comprising said surgical instrument 1 of the needle-holder/cutter type is particularly suitable, but not uniquely intended, for robotic microsurgery operations. The robotic surgery system 101 can be intended for robotic laparoscopy operations.

Said surgical instrument 1 of the needle-holder/cutter type comprises an articulated end-effector 9, in other words an articulated terminal 9. In accordance with an embodiment, said surgical instrument 1 of the needle-holder/cutter type comprises a shaft 7 and said articulated end-effector 9 at the distal end 8 of the shaft 7. Not necessarily said shaft 7 is a rigid shaft and for example can be a bendable shaft and/or an articulated shaft, although in accordance with a preferred embodiment said shaft 7 is a rigid shaft. A proximal interface portion 61 or backend portion 61 of the surgical instrument 1 can be provided at the proximal end 62 of the shaft 7, to form the interface with a robotic manipulator 63 of the robotic surgery system 101, as shown for example in FIG. 2. A sterile barrier can be interposed between the robotic manipulator and the proximal interface portion 61 of the surgical instrument. For example, said proximal interface portion 61 can comprise a set of interface transmission elements for receiving the driving actions imparted by the robotic manipulator 63 and transmitting them to the articulated end-effector 9. In accordance with an embodiment, the surgical instrument 1 of the needle-holder/cutter type is detachably associated with the robotic manipulator 63 of the robotic surgery system 101.

The articulated end-effector 9 at the distal end 8 of the shaft 7 can comprise a plurality of links articulated to one another in one or more rotational joints movable by a number of pairs of antagonistic actuation tendons extending from the proximal interface portion 61 to the articulated end-effector 9 inside the shaft 7 ending in termination seats provided on at least some of the links of the articulated end-effector 9. The pair of actuation tendons of one or more pairs of antagonistic tendons can be obtained with a single tendon forming a round trip path from the proximal interface portion 61 of the instrument to a link of the articulated end-effector of the instrument.

Not necessarily all the links forming the articulated end-effector 9 are articulated, i.e., movable, with respect to the distal end 8 of the shaft 7. For example, said end-effector 9 can be an articulated cuff of the "roll-pitch-yaw" type according to a terminology widely adopted in the field. For example, said end-effector 9 can be an articulated end-effector 9 of the "snake" type, i.e., comprising a multitude of coplanar and/or non-planar rotational joints.

Said articulated end-effector 9 of the surgical instrument of the needle-holder/cutter type 1 comprises a support structure comprising two prongs 3, 4 comprising a first prong 3 and a second prong 4 forming a support fork. Preferably, the support fork (or support structure) is made in a single piece, i.e., said two prongs 3, 4 are made in a single piece. In accordance with a preferred embodiment, said articulated end-effector 9 comprises a support link 2 comprising said support fork comprising said two prongs 3, 4.

Preferably, the term "link" refers to a body made in a single piece, i.e., a monobloc body.

Figure 3:
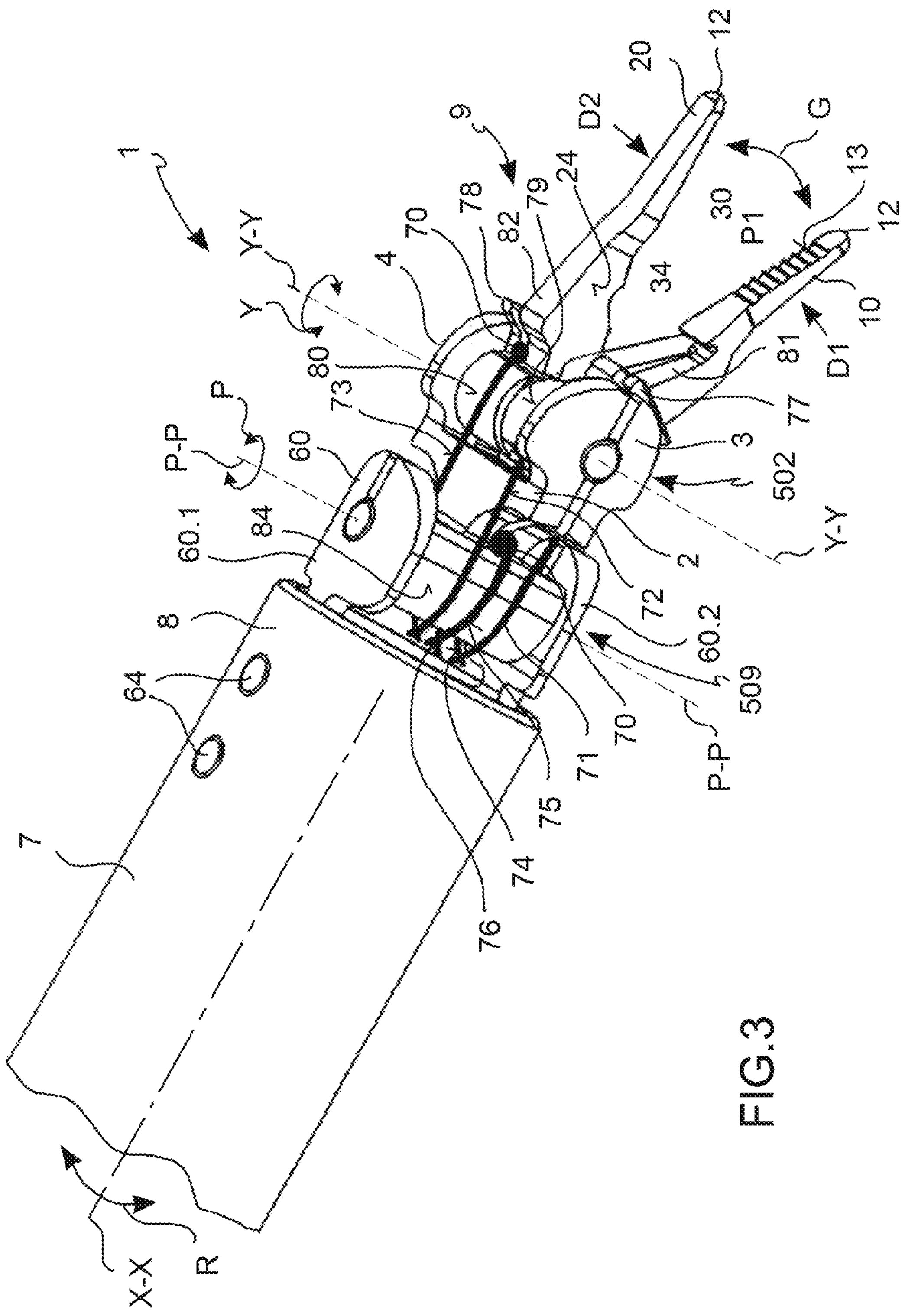
FIG. 3 shows an axonometric view of a portion of a surgical instrument of the needle-holder/cutter type comprising an end-effector at the distal end of the shaft, according to an embodiment, in which the actuation tendons are diagrammatically shown.

In accordance with an embodiment as shown in FIG. 3, for example, the support link 2 comprising the support fork with said prongs 3, 4 is a separate piece with respect to the shaft 7 and articulated thereto, by interposition between the support link 2 and the distal end 8 of the shaft 7 of a further connection link 60 rigidly fixed by means of a fixing device 64 (in the example shown as a pair of fixing pins 64, but alternatively the fixing device 64 can comprise plugs, rivets, staples, one or more threaded elements, interlocking profiles, or the like) at the distal end of the shaft 7 and in turn comprising two prongs 60.1, 60.2 articulated to the support link 2 with respect to the shaft 7 about a common proximal rotation axis P-P, or pitch axis P-P (the term "pitch" is used here arbitrarily and can indicate any orientation of the common rotation axis P-P). In such a case, therefore, the prongs 3 and 4 are articulated with respect to the distal end 8 of the shaft 7.

Figure 8A:
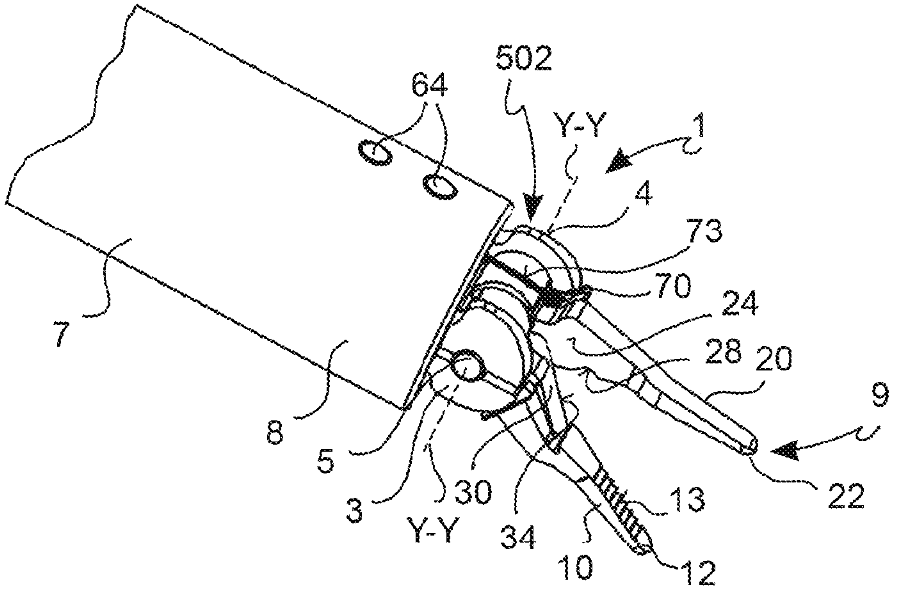
FIG. 8A shows an axonometric view of a surgical instrument of the needle-holder/cutter type comprising an end-effector at the distal end of the shaft, according to an embodiment, in which the actuation tendons are diagrammatically shown.
Figure 8B:
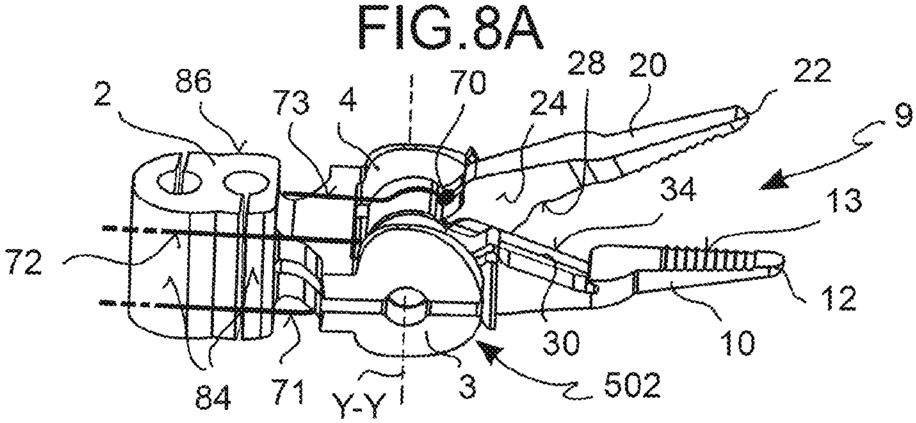
FIG. 8B shows the end-effector and diagrammatically the actuation tendons in FIG. 8A.

In accordance with an embodiment as shown in FIGS. 8A and 8B, for example, the support link 2 comprising the support fork with said prongs 3, 4 is a separate piece with respect to the shaft 7 and rigidly fixed thereto, i.e., not articulated, by means of a fixing device 64 (in the example shown as a pair of pins). In such a case, therefore, the prongs 3 and 4 are integral with the distal end 8 of the shaft 7.

Figure 9:
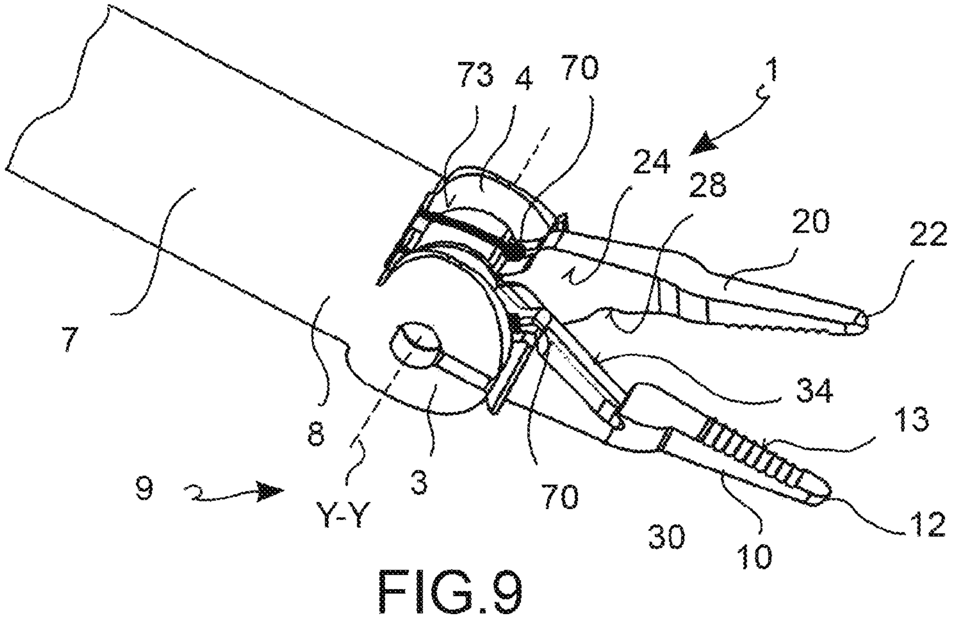
FIG. 9 shows an axonometric view of a surgical instrument of the needle-holder/cutter type comprising an end-effector, according to an embodiment, in which the actuation tendons are diagrammatically shown.
Figure 10:
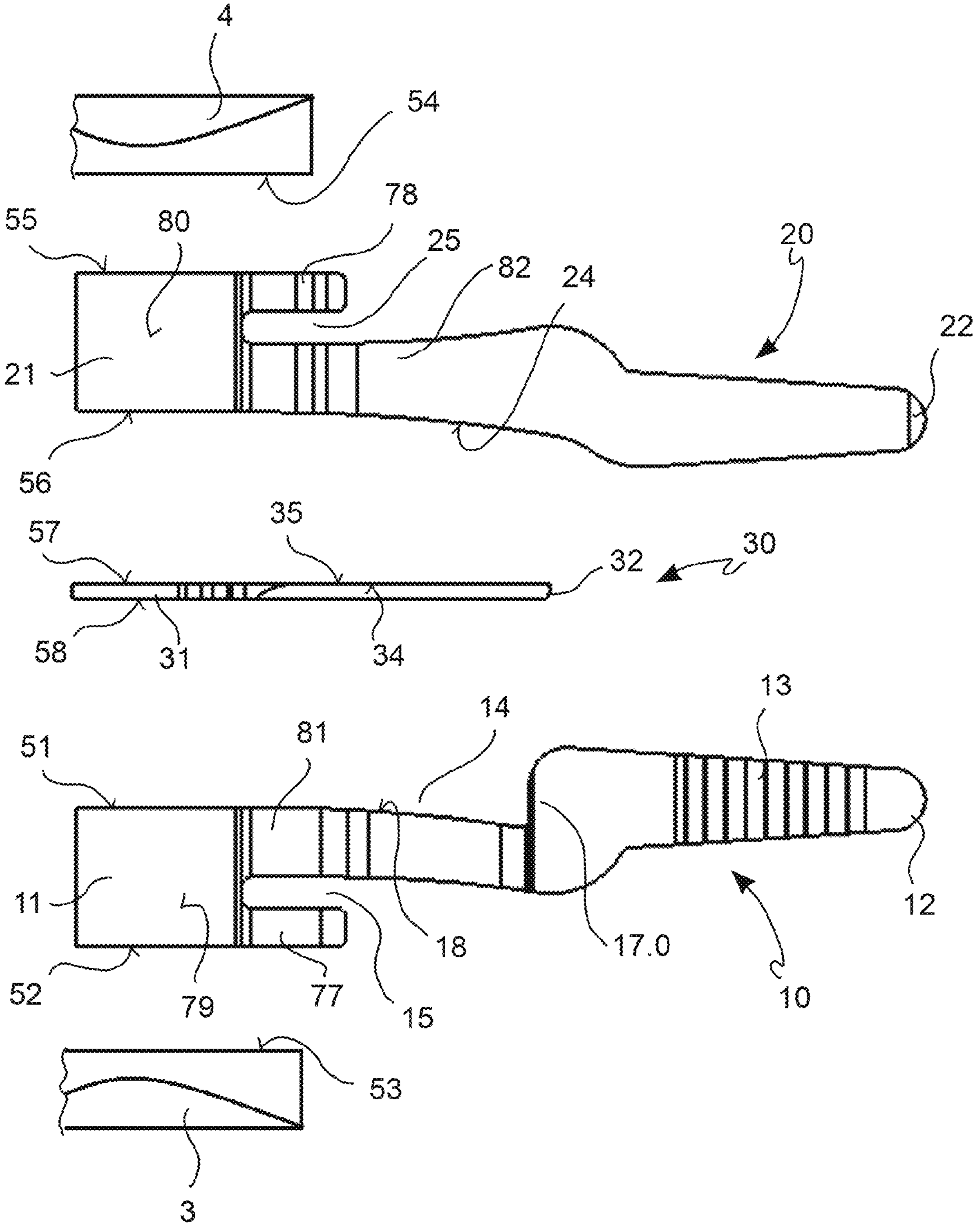
FIG. 10 shows a plan view with separate parts of a portion of an end-effector of a surgical instrument of the needle-holder/cutter type, according to an embodiment.

In accordance with an embodiment as shown in FIG. 9, for example, the support structure or fork comprising said prongs 3, 4 is formed in a single piece with the distal end 8 of the shaft 7. In such a case, therefore, the prongs 3 and 4 are integral with respect to the distal end 8 of the shaft 7 and the articulated end-effector 9 further comprises the distal end 8 of the shaft 7 having the two prongs 3, 4, i.e., for the purposes of this disclosure and in this embodiment the distal end 8 of the shaft 7 comprising two prongs 3, 4 is understood as belonging to the articulated end-effector 9.

Said articulated end-effector 9 of the surgical instrument of the needle-holder/cutter type 1 further comprises a first tip link 10 (or blade holder link 10) and a second tip link 20 (or reaction link 20). Preferably, said first and second tips 10 and 20 each have an elongated body, the elongated bodies of said first and second tips 10 and 20 being constrained to each other in respective proximal portions, or roots 11, 21, to rotate about a common rotation axis Y-Y being intended to form a terminal gripping device of the articulated end-effector 9 to grip a surgical needle.

In particular, the body of the first tip link 10 comprises in a single piece a first proximal attachment root 11, a first free distal end 12 and a first gripping surface 13 therebetween, and the body of the second tip link 20 comprises in a single piece a second proximal attachment root 21, a second free distal end 22 and a second gripping surface 23 therebetween. It is possible to define a connecting portion 81, 82 for each tip link 10, 20 between the attachment root 11 or 21 and the respective gripping surface 13, 23. When in use, the first gripping surface 13 of the first tip link 10 and the second gripping surface 23 of the second tip link 20 are intended to be mutually opposite and facing each other in rotation, to move in mutual contact to exert a gripping action for example on a surgical needle. Each gripping surface 13, 23 can be machined according to known techniques, forming ridges and recesses to increase the gripping capacity.

Advantageously, said articulated end-effector 9 of the surgical instrument of the needle-holder/cutter type 1 further comprises a blade link 30 or blade 30 comprising in a single piece a third proximal attachment root 31 and a cutting edge 34 elastically deformable by bending which can be sharpened, i.e., it can be subject to sharpening to have a locally reduced thickness with respect to the thickness of the body of the blade link 30 and/or a sharp conformation in cross-section. By virtue of the provision of said blade 30, said articulated end-effector 9 of the surgical instrument of the needle-holder/cutter type 1 allows exerting a useful cutting action for cutting a suture wire 6 which can be connected to a surgical needle.

Preferably, the body of the first tip link 10 and the body of the second tip link 20 each have a longitudinally elongated conformation extending from the respective attachment root to the respective free end, in which the respective gripping surface is placed close to the respective free end, and in which the roots 11, 21, 31 of the first tip link 10 of the second tip link 20 and of the blade link 30 are next to one another, while in a respective connecting portion 81, 82 the body of the first tip link 10 and of the second tip link 20 which is longitudinally interposed between the respective root 11, 21 and the respective gripping surface 13, 23, an axial and longitudinal seat is obtained for receiving the body of the blade link 30 with the cutting edge 34 thereof. In other words, the elongated body of the first tip link 10 and of the second tip link 20 are next to each other at the respective root 11, 21 and at the respective connecting portion 81, 82, and are overlapping at the respective gripping surface 13, 23, while the blade link 30 is next to the roots 11, 21 of the first and second tip links 10, 20 at the root 31 thereof and is next to, and interposed between the connecting portions 81, 82 of the first and second tip links 10, 20.

In accordance with a preferred embodiment, the root of the blade link 31 is interposed between the roots 11, 21 of the first and second tip links 10, 20. Preferably, the body of the blade link 30 is also longitudinally elongated and comprises a blade link end 32, but is made shorter with respect to the body of the first tip link 10 and the second tip link 20, and extends substantially in the longitudinal direction from the attachment roots 11, 21, next to each other, to the of the gripping surface area 13, 23 of the first tip link 10 and of the second tip link 23, i.e., the distal end 32 of the blade 30 extends longitudinally to a level which is close to the proximal edge of the gripping surfaces 13, 23 of the first and second tip links 10, 20.

In accordance with an embodiment, said blade link 30 is made by shaping, i.e., by cutting, suitably a substantially flat elastic sheet or strip. For example, the elastic sheet or strip can be made of spring steel and shaped by wire electro-erosion (WEDM) and/or photo-etching and/or laser cutting and/or chemical etching. Preferably, the elastic sheet or strip is sharpened on one edge thereof to form the cutting edge 34 of the blade link 30. The sharpening can be carried out by wire electro-erosion (WEDM) and/or grinding, for example stone or diamond grinding. In accordance with an embodiment, first the elastic sheet or strip is shaped by wire electro-erosion (WEDM) in a step in which the cutting edge flows in a direction substantially orthogonal to the lying plane of the sheet or strip, then one or more edges of the shaped sheet or strip are sharpened by wire electro-erosion (WEDM) in a step in which the cutting edge flows in a direction not orthogonal to the lying plane of the shaped sheet or strip.

In accordance with an embodiment, the body of the blade link 30 has a two-dimensional main extension, i.e., lying on a preferably flat or arched lying surface, and has a substantially reduced thickness with respect to the extension on said preferably flat or arched lying surface.

In accordance with an embodiment, the cutting edge 34 of the blade link 30 is substantially straight in the preferably flat or arched lying surface, avoiding the provision of concavities in the lying surface of the body of the blade link 30.

Preferably, the thickness of the blade link 30 is significantly less with respect to the thickness of said first and second tip links 10, 20 and is chosen so that the blade is elastically bendable when in operating conditions transversely to the longitudinal extension of the blade link 30, i.e., in the direction of the thickness. In particular, the blade link 30 must be more bendable than the second tip link 20 and preferably also more bendable than the first tip link 10. The flexibility of the blade link 30 and thus the flexibility of the cutting edge 34 of the blade link 30 is intended in the direction of the thickness thereof, i.e., in a direction orthogonal to the blade link lying surface. Such a lying surface of the body of the blade link 30 can substantially correspond to the lying plane of the starting metal strip or sheet which suitably processed forms the blade link 30, even though in accordance with a possible embodiment the body of the blade link 30 is forced to have an arched, i.e., concave, conformation having a concavity facing in a direction exiting from/entering the lying plane of the starting elastic strip or sheet and in this case the lying surface of the blade link body will be an arched surface.

Not necessarily the blade link 30 and thus the cutting edge 34 of the blade link 30 must be elastically deformable in the lying surface, i.e., a bendability in a direction orthogonal to the thickness thereof is not necessarily provided.

The material of the blade link 30 can be a different material with respect to the material of the first tip link 10 and/or the second tip link 20. For example, the blade link 30 can be made of spring steel. For example, the first tip link 10 and the second tip link 20 and the support link 2, when present, can be made of a single metal material, for example steel. For example, the counter-blade link 40, when present, can be made of spring steel.

The ratio between the thickness of the blade link 30 at the level of the third root 31 thereof and/or the body of the blade link 30 (excluding in this evaluation the thickness of the cutting edge 34, which as mentioned is preferably sharpened) and the thickness of the first root 11 of the first tip link 10 and/or the thickness of the second root 21 of the second tip link 20 can be between ⅕ and 1/20. In absolute value the thickness of the blade link 30 can be between 0.1 mm and 1 mm.

Said support structure having the prongs 3, 4 (support structure for example formed by the support link 2 or by the distal end 8 of the shaft), the first tip link 10, the second tip link 20 and the blade link 30 are made in separate pieces and said blade link 30 is integral in rotation with said first tip link 10. Therefore, the first tip link 10 acts as a blade holder link. Thereby, the cutting edge 34 is integral in rotation with the first gripping surface 13 and with the first free end 12 of the first tip link 10 and, being elastically bendable, the cutting edge 34 can elastically deform with respect to the first tip link 10 integral in rotation thereto when in operating conditions. The elastic deformation of the cutting edge 34 preferably occurs in a transverse direction with respect to the longitudinal extension direction of the elongated body of the first tip link 10, i.e., in a transverse direction with respect to the direction joining the first proximal attachment root 11 and the first distal free end 12 of the first tip link 10, in other words in the direction of the thickness of the blade link 30.

In particular, the first root 11 of the first tip link 10, the second root 21 of the second tip link 20 and the third root 31 of the blade link 30 are articulated with respect to the prongs 3, 4 of the support structure about said common rotation axis Y-Y defining a degree of freedom of orientation between the support structure and the group formed by: said first tip link 10, said second tip link 20 and said blade link 30. A distal rotational joint 502 of a cutting joint is therefore made. Therefore, the common rotation axis Y-Y (or a straight extension thereof) passes through said two prongs 3, 4, and said first, second and third proximal attachment root 11, 21, 31 and can be defined by an articulation pin 5. Furthermore, the first root 11 of the first tip link 10, the second root 21 of the second tip link 20 and the third root 31 of the blade link 30 are mutually articulated about said common rotation axis Y-Y defining a relative degree of freedom of opening/closing G (or grip G) between the second tip link 20 and the group formed by: the first tip link 10 and the blade link 30. Thereby, the second free end 22 as well as the second gripping surface 23 of the second tip link 20 and the group formed by: the cutting edge 34 of the blade link 30 and the first free end 12, as well as the first gripping surface 13 of the first tip link 10 and are relatively movable in an opening/closing direction, i.e., in a relative approaching/distancing direction.

In accordance with an embodiment, said opposite and facing in rotation first and second gripping surfaces 13, 23 act as closing stroke ends for said articulated end-effector 9 of the surgical instrument of the needle-holder/cutter type 1.

Figure 2:
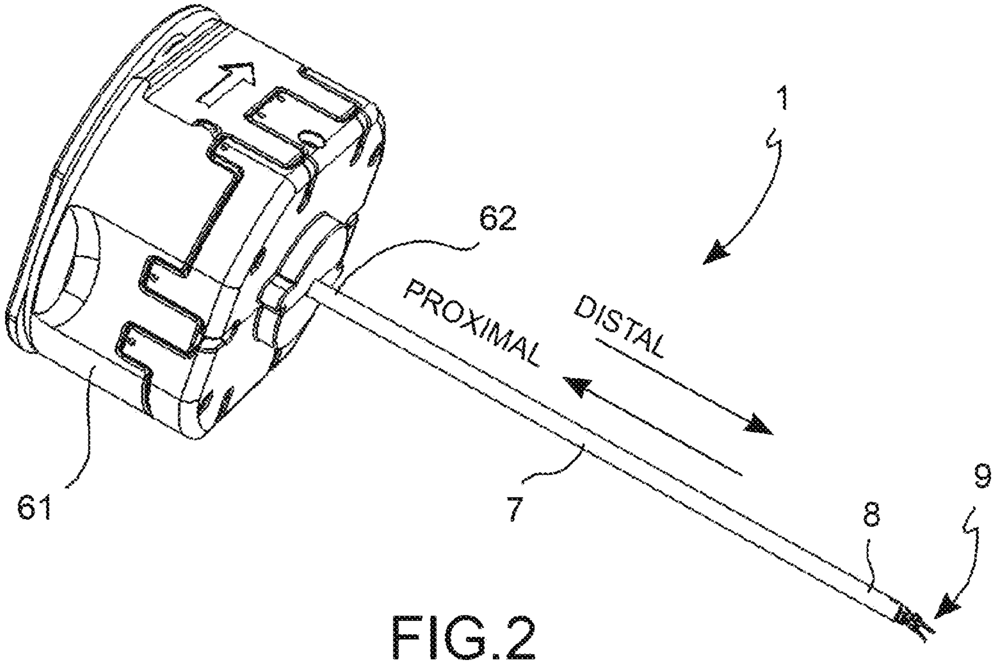
FIG. 2 shows an axonometric view of a surgical instrument of the needle-holder/cutter type, according to an embodiment.

The proximal and distal directions (or senses) are understood as referring in accordance with the common meaning of the terms, as shown by the arrows in FIG. 2. Preferably, for clarity of presentation, an axial direction coincident or parallel with the direction of the common rotation axis Y-Y is defined. Preferably, for clarity of presentation, with reference to the first tip link 10, an internal axial direction facing the second tip link 20 is also defined and similarly said internal axial direction will be with reference to the second tip link 20 facing to be opposite i.e., towards the first tip link 10. Preferably, for clarity of presentation, the term "radial" will refer to a direction which is substantially orthogonal to the common rotation axis Y-Y and incident thereto. Preferably, for clarity of presentation, it also means a longitudinal direction which globally can be substantially coincident with the extension development direction of the surgical instrument of the needle-holder/cutter type 1, as well as locally with the longitudinal extension direction of the elongated body of the first tip link 10 and/or with the longitudinal extension direction of the elongated body of the second tip link 20. Preferably, for clarity of presentation, a first back side D1 of the first tip link 10 and a second back side D2 of the second tip link 20 are defined with reference to the relative degree of freedom of opening/closing G, said first back side D1 and second back side D2 are facing mutually opposite, and a first gripping side P1 of the first tip link 10 is defined in which said first gripping surface 13 belongs to said first gripping side P1 of the first tip link 10, and a second gripping side P2 of the second tip link 20 in which said second gripping surface 23 belongs to said second gripping side P2, said first gripping side P1 of the first tip link 10 and second gripping side P2 of the second tip link 20 are opposite and substantially placed side by side in rotation, although preferably they are mainly placed side by side and can only be in contact in said first and second gripping surfaces 13, 23 when the degree of freedom of opening/closing G is in a closing configuration. In other words, the gripping surfaces 13 and 23 are made on respective internal axial protrusions of the first gripping side P1 of the first tip link 10 and of the second gripping side P2 of the second tip link 20.

As mentioned above, the support structure (e.g., formed by the support link 2 or the distal end 8 of the shaft 7), the first tip link 10, the second tip link 20 and the blade link 30 are made in separate pieces, and are preferably formed by four separate pieces (for example four links 2, 10, 20, 30 or three links 10, 20, 30 and the distal end 8 of the shaft 7 provided with two prongs 3, 4) joined together in a common rotation axis Y-Y which is constrained to rotate with respect to a common rotation axis Y-Y, or common rotation axis of yaw Y-Y (the term "yaw" is used here arbitrarily and can indicate any orientation of the common rotation axis Y-Y, although in accordance with a preferred embodiment it is meant to indicate a common rotation axis of yaw Y-Y which is non-parallel and preferably orthogonal to the common proximal rotation axis of pitch P-P already mentioned above).

Further links as well as further pieces can be present in the end-effector 9, although in accordance with an embodiment the articulated end-effector 9 consists of exactly said four pieces articulated together in said common axis Y-Y and suitably movable by actuation tendons. In accordance with an embodiment, the articulated end-effector 9 consists of exactly said four pieces articulated together in said common axis Y-Y and suitably movable by actuation tendons plus a further piece which is an articulation pin 5 defining said common axis Y-Y (in total five pieces, the actuation tendons are excluded from the count).

In accordance with an embodiment, the articulated end-effector 9 consists of exactly three pieces articulated to one another in said common axis Y-Y with respect to said support structure, which are said first tip link 10, said second tip link 20 and said blade link 30, plus a further piece which is a articulation pin 5 defining said common axis Y-Y (in total four pieces, the actuation tendons are excluded from the count). Actuation tendons can be connected to the first and to the second link.

In accordance with an embodiment, the articulated end-effector 9 consists of exactly said four pieces (i.e., said four links 2, 10, 20, 30) articulated in said common axis Y-Y, plus a further piece which is a articulation pin 5 defining said common axis Y-Y, plus a further connection link 60 with the shaft 7 which is articulated with respect to the support link 2 in the common proximal rotation axis of pitch P-P by means of a further proximal articulation pin 65 defining said common proximal rotation axis of pitch P-P (in total seven pieces; the actuation tendons are excluded from the count). By virtue of this embodiment, where the common rotation axis of pitch P-P is non-parallel (preferably orthogonal) to the common rotation axis of yaw Y-Y, it allows obtaining a articulated cuff at the distal end of the shaft 7 and where the rotation axis of pitch P-P is non-parallel and preferably orthogonal to the common rotation axis of yaw Y-Y, the articulated cuff is provided with the degrees of freedom of pitch, yaw and grip G, in which the degree of freedom of grip G is adapted to manage gripping and cutting. Where the connection link 60 is made in a single piece with the distal end 8 of the shaft 7 (not shown in the figure), the articulated end-effector 9 will still be formed by said seven pieces which are: the distal end 8 of the shaft 7, the support link 2, the blade link 30, the first tip link 10, the second tip link 20, and said two articulation pins 5, 65.

A degree of freedom of roll R integral with the shaft 7 and preferably also with the backend portion 61 can be provided, for example a degree of freedom of roll R which allows the entire surgical instrument 1 to be rotated about the longitudinal extension axis X-X of the shaft 7.

Those skilled in the art will appreciate that minimizing the number of pieces greatly simplifies the assembly of the articulated end-effector 9 of the surgical instrument 1 of the needle-holder/cutter type, making it suitable for an extreme miniaturization. In particular, avoiding the provision of elastic preload elements in the axial direction (such as Belleville-type elastic washers fitted on the articulation pin 5), i.e., in the direction of the common rotation axis Y-Y between the prongs 3, 4 of the support structure, it is possible to simplify the assembly of the pieces and therefore an extreme miniaturization of the articulated end-effector 9 is favored, as well as consequently of the cross-section of the shaft 7, while ensuring a satisfactory strength and resistance to the stresses which can arise when in operating conditions.

Figure 12:
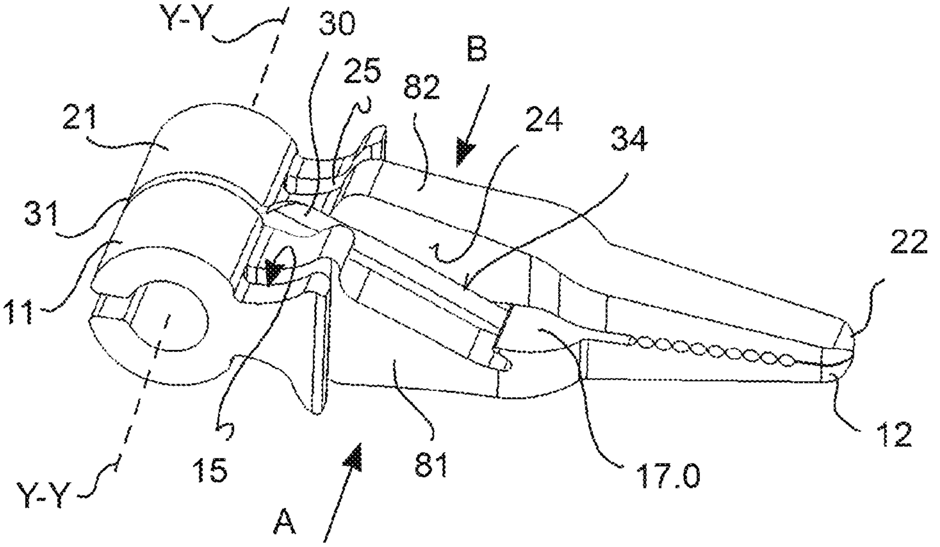
FIG. 12 shows an axonometric view of a portion of the end-effector in the cutting configuration shown in FIG. 11.
Figure 13A:
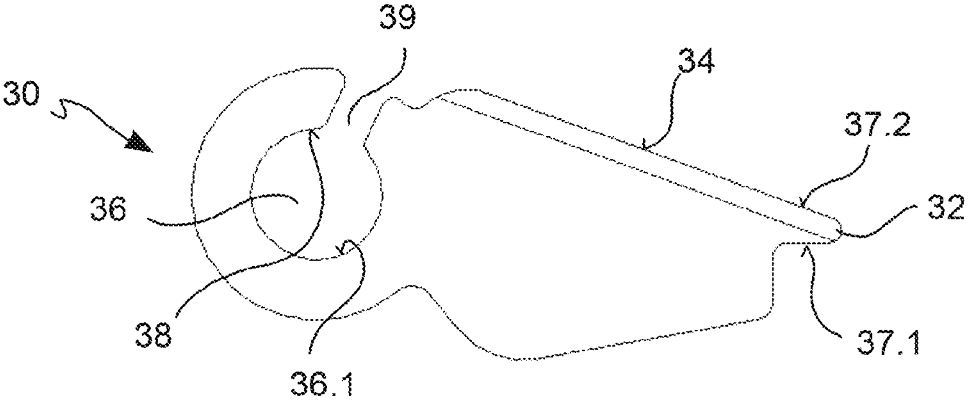
FIG. 13A shows a vertical elevation view of a blade link of the portion of the end-effector in FIG. 10.
Figure 13B:
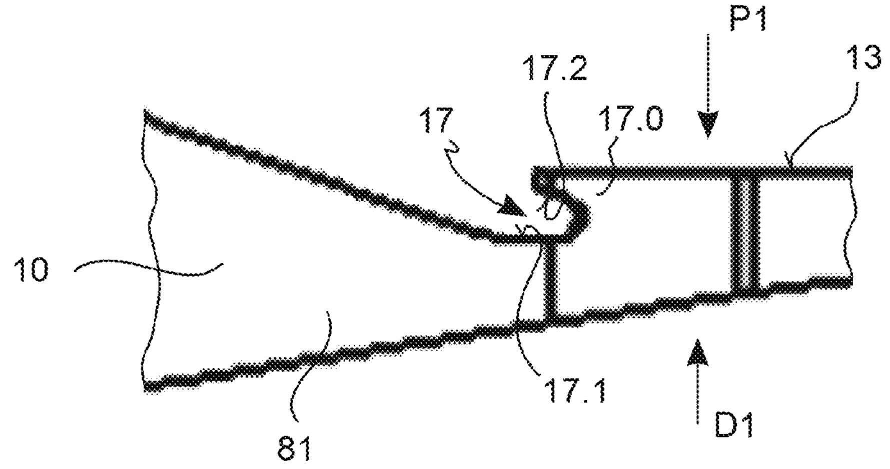
FIG. 13B shows a vertical elevation view of a portion of the blade holder link of the end-effector portion in FIG. 10, according to an embodiment.

With further advantage, a counter-blade surface 24 integral in rotation with the second tip link 20 is provided. In other words, the articulated end-effector 9 further comprises said counter-blade surface 24 integral in rotation with the second tip link 20. The counter-blade surface 24 is not necessarily made in a single piece with the second tip link 20, although in accordance with a preferred embodiment it is made in a single piece with said second tip link 20, as shown for example in FIG. 12.

Figure 21:
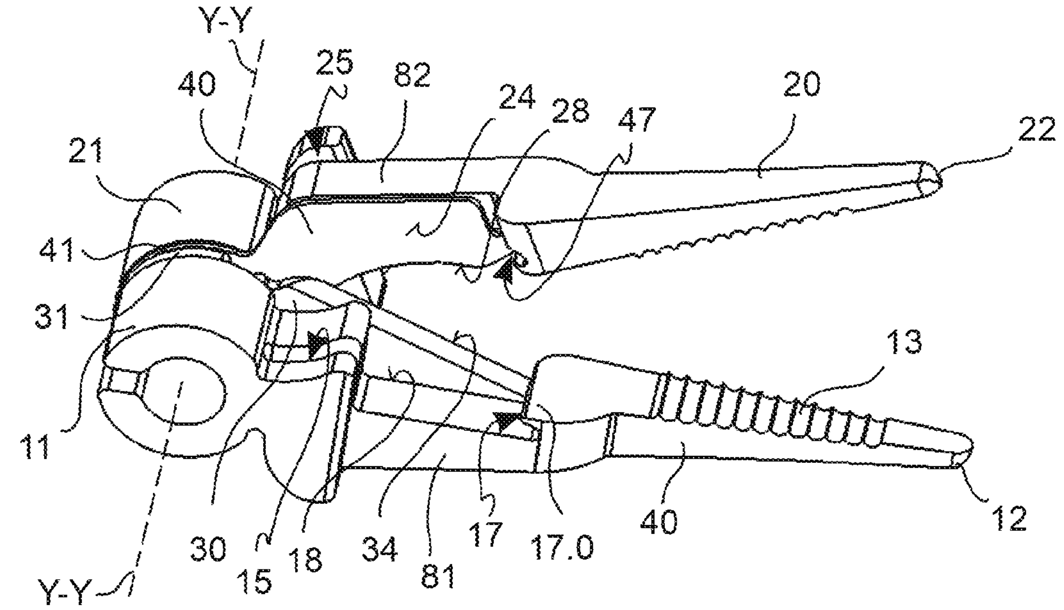
FIG. 21 shows an axonometric view of a portion of the end-effector in FIG. 19 in assembled configuration.
Figure 22:
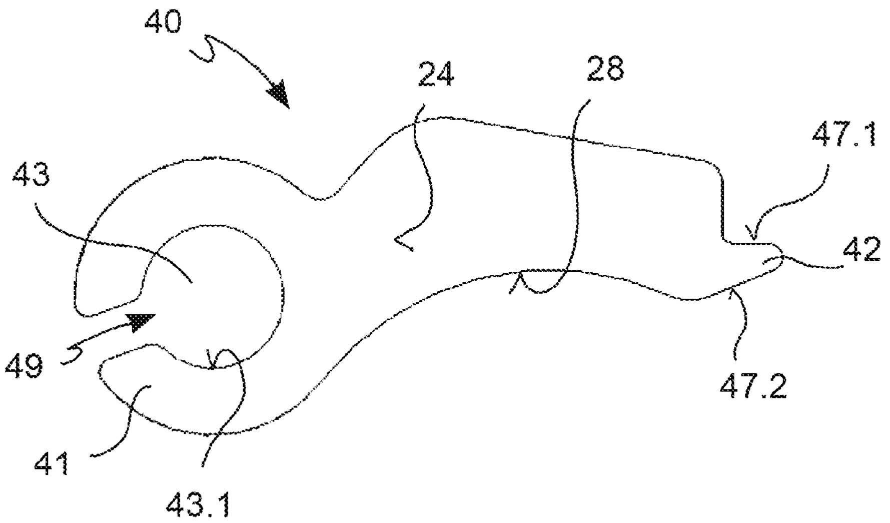
FIG. 22 shows a vertical elevation view of a counter-blade link of the end-effector in FIG. 19.
Figure 23:
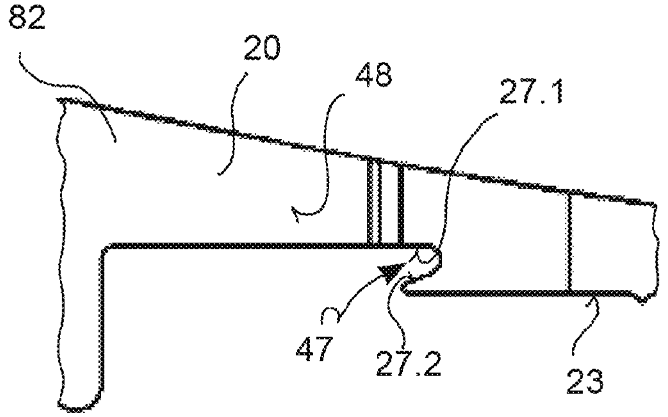
FIG. 23 shows a vertical elevation view of a portion of a second tip link of the end-effector of FIG. 19.
Figure 24:
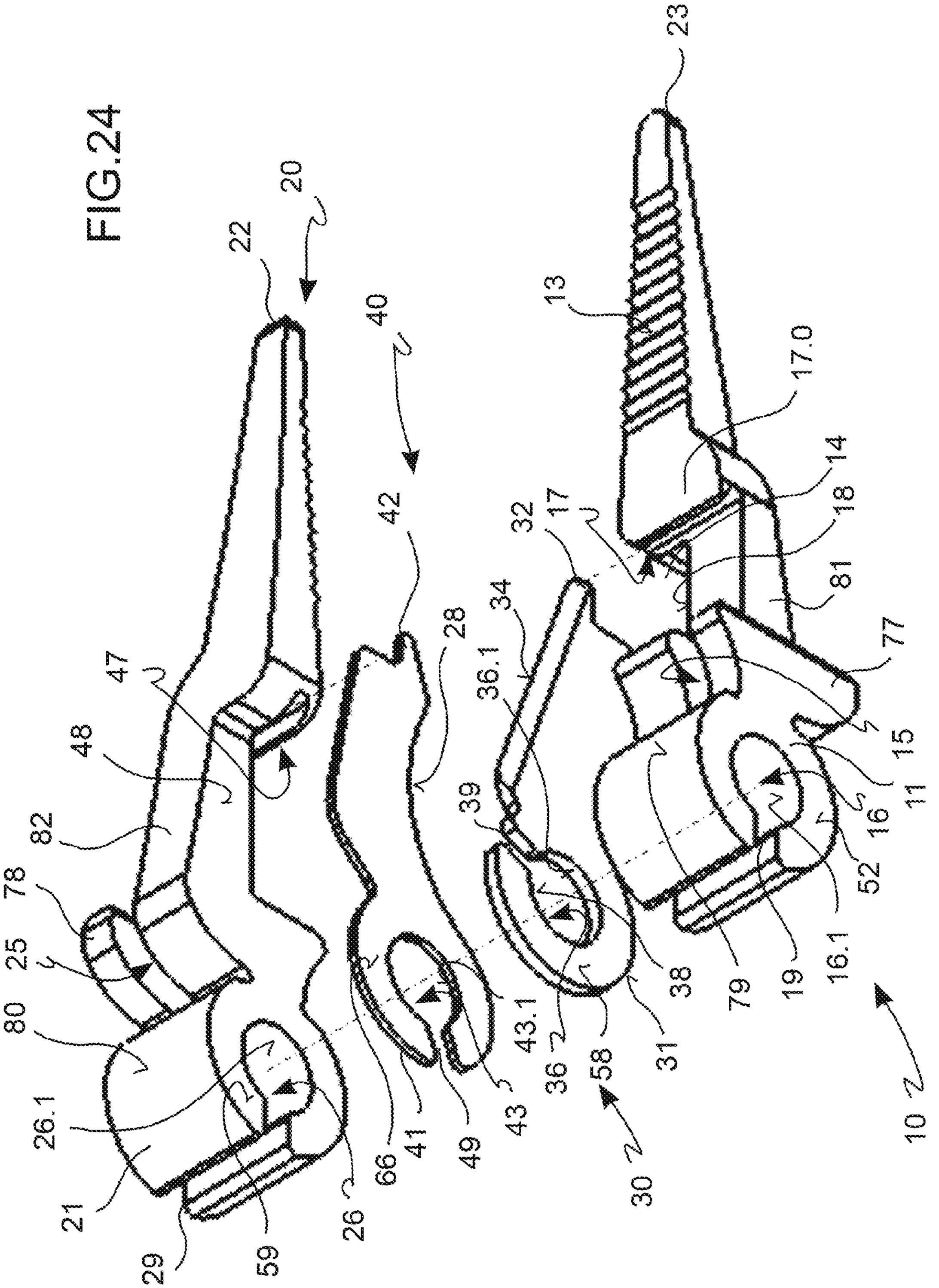
FIG. 24 shows an axonometric view with separate parts of a portion of the end-effector in FIG. 19.
Figure 25:
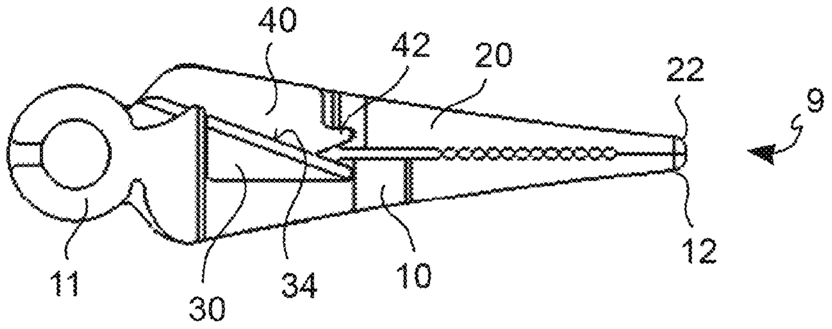
FIG. 25 shows a vertical elevation view in assembled configuration of the portion of the end-effector in FIG. 24.
Figure 26:
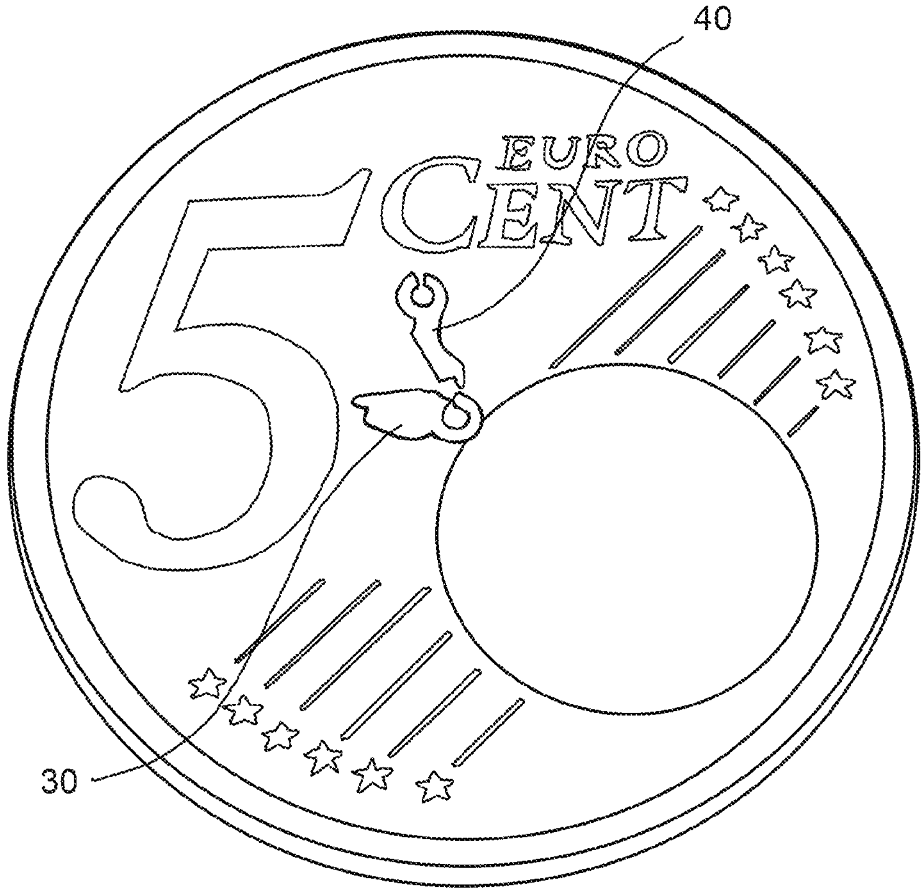
FIG. 26 is an electron microscope photographic image depicting a blade link and a counter-blade link placed on a face of a five euro cent coin.

In accordance with an embodiment as shown for example in FIG. 21, a counter-blade link 40 can be provided in a separate piece with respect to said second tip link 20 and integral in rotation therewith, said counter-blade link 40 comprising said counter-blade surface 24 and a fourth proximal attachment root 41 articulated in said common rotation axis Y-Y.

Said counter-blade surface 24 is adapted to abut against said cutting edge 34 of the elastically deformable blade link 30, so that said counter-blade surface 24 and said cutting edge 34 of the blade link 30 reach a mechanical interference contact condition to exert a cutting action. Preferably, the cutting edge 34 of the blade link 30 is sharpened so as to be flush with the axially facing blade surface 35 of the blade link 30 which is placed axially facing the counter-blade surface 24. During the cutting action, at least one portion of the blade surface 35 can contact the counter-blade surface 24 causing direct friction substantially in the opening/closing direction G.

Where the counter-blade surface 24 is made in a single piece with the second tip link 20, it faces axially internally and preferably belongs to the connecting portion 82 of the elongated body of the second tip link 20, so as to be able to go into mechanical interference contact with the cutting edge 34 of the blade to perform a cutting action.

In accordance with a preferred embodiment, the counter-blade surface 24 integral in rotation with the second tip link 20 protrudes towards the rotational footprint of the body of the blade link 30, to elastically bend the blade link 30 when in mechanical interference contact with the cutting edge 34. In other words, the counter-blade surface 24 protrudes axially internally. Said protrusion of the counter-blade surface 24 is accentuated towards the distal direction, i.e., away from the common rotation axis Y-Y along the longitudinal extension of the second tip link 20 and preferably said protrusion is maximum close to or at the distal end 32 of the blade link 30. In accordance with a preferred embodiment, the protrusion of the counter-blade surface 24 is progressively obtained by following the counter-blade surface in the distal direction, in which, for example, progressively more distal sections have accentuated protrusion.

Therefore, in accordance with an embodiment, the first tip link 10 comprises a surface facing axially inwards 18 which is inclined away from the body of the blade link body 30, axially internally delimiting an axial deformation recess 14 (or deformation seat 14) adapted to accommodate the body of the blade link 30 when elastically bent by the action of the protruding counter-blade surface 24 integral in rotation with said second tip link 20 during the cutting action. Therefore, the counter-blade surface 24 and the surface facing axially inwards 18 both face the blade link 30 and are both in contact therewith during the cutting action. The surface 18 facing axially inwards preferably belongs to said connecting portion 81 of the elongated body of the first tip link 10.

Preferably, the internally axially facing surface 18 of the first tip link 10 serves as the axial stroke end abutment surface for the deformation of the blade link 30 when deformed by bending by the counter-blade surface 24, during the cutting action. The profiles of the protruding surface of the counter-blade 24 and the axially facing surface 18 of the first tip link 10 can be parallel to each other, and in an embodiment are correspondingly identical.

Preferably, the terminology “rotational approaching footprint” is meant to indicate the volume of space which the body of an element can occupy during the relative closing rotation movement of the degree of freedom of grip G. Therefore, the terminology “rotational approaching footprint of the blade link 30” is meant to indicate the volume of space which can be occupied by the body of the blade link 30 during the relative closing rotation movement of the degree of freedom of grip G. Similarly, “rotational approaching dimension of the first link of tip 10” is meant to indicate the volume of space which can be occupied by the gripping side P1 of the body of the first tip link 10 during the relative closing rotation movement of the degree of freedom of grip G and “rotational approaching dimension of the second tip link 20” is meant to indicate the volume of space which can be occupied by the gripping side P2 of the body of the second tip link 20 during the relative closing rotation movement of the degree of freedom of grip G.

The mechanical interference contact between the cutting edge 34 and the counter-blade surface 24 which determines the cutting action simultaneously deforms the body of the blade link 30 in bending. The bending deformation of the body of the blade link 30 during the cutting action is preferably directed axially towards the surface 18 facing axially inwards of the first tip link 10. The bending deformation of the body of the blade link 30 during the cutting action is directed, for example, substantially parallel to the common rotation axis Y-Y.

Figure 14:
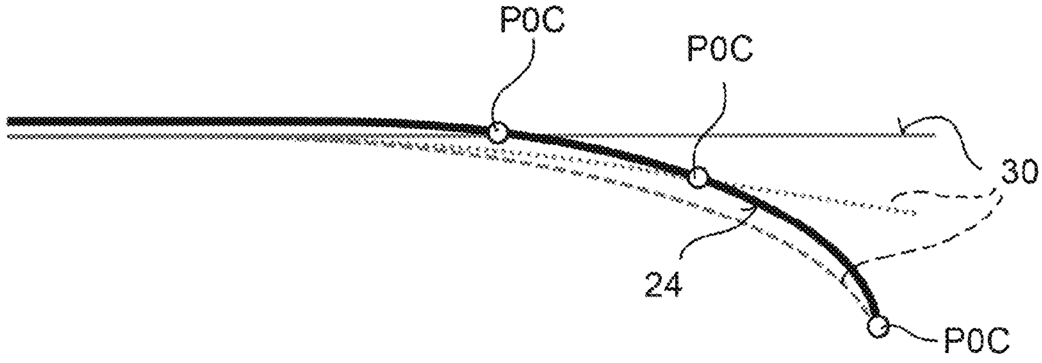
FIG. 14 is a diagram which diagrammatically shows a plan view of the conformation assumed by a blade portion and a counter-blade surface in various mechanical cutting interference configurations, according to an embodiment.
Figure 15A:
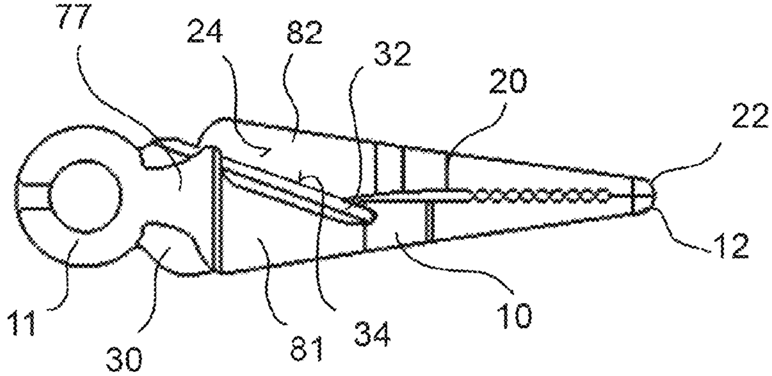
FIGS. 15A and 15B are vertical elevation views of the end-effector portion in FIG. 11 according to the points of view indicated by arrows A and B, respectively.
Figure 15B:
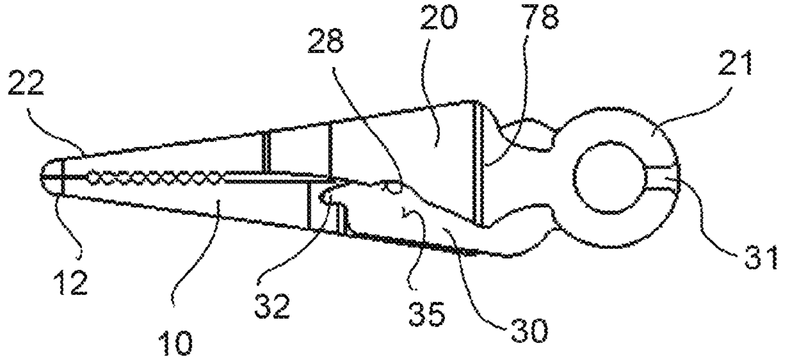
Figure 16:
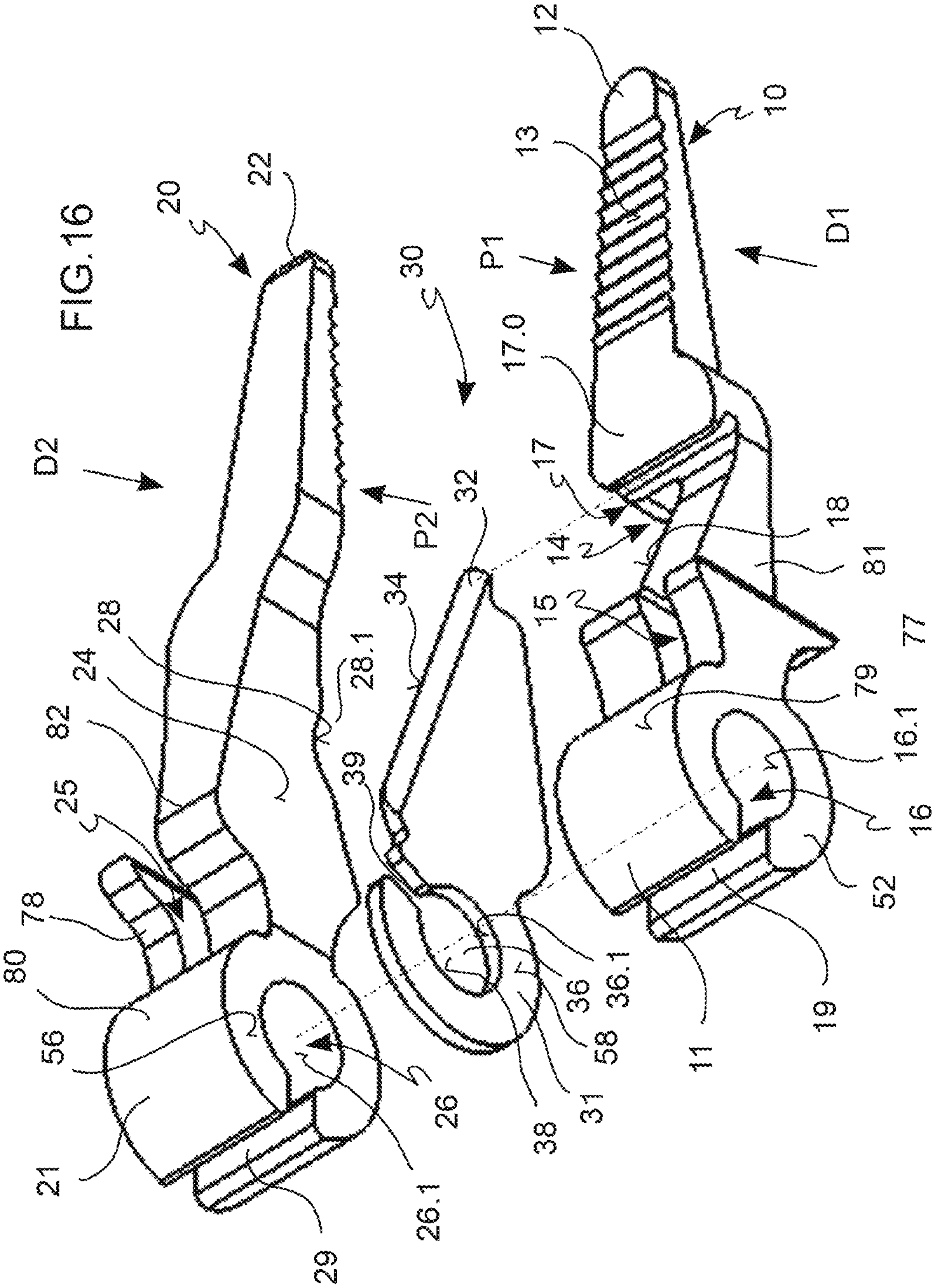
FIG. 16 shows an axonometric view with separate parts of a portion of the end-effector in FIG. 11.
Figure 17A:
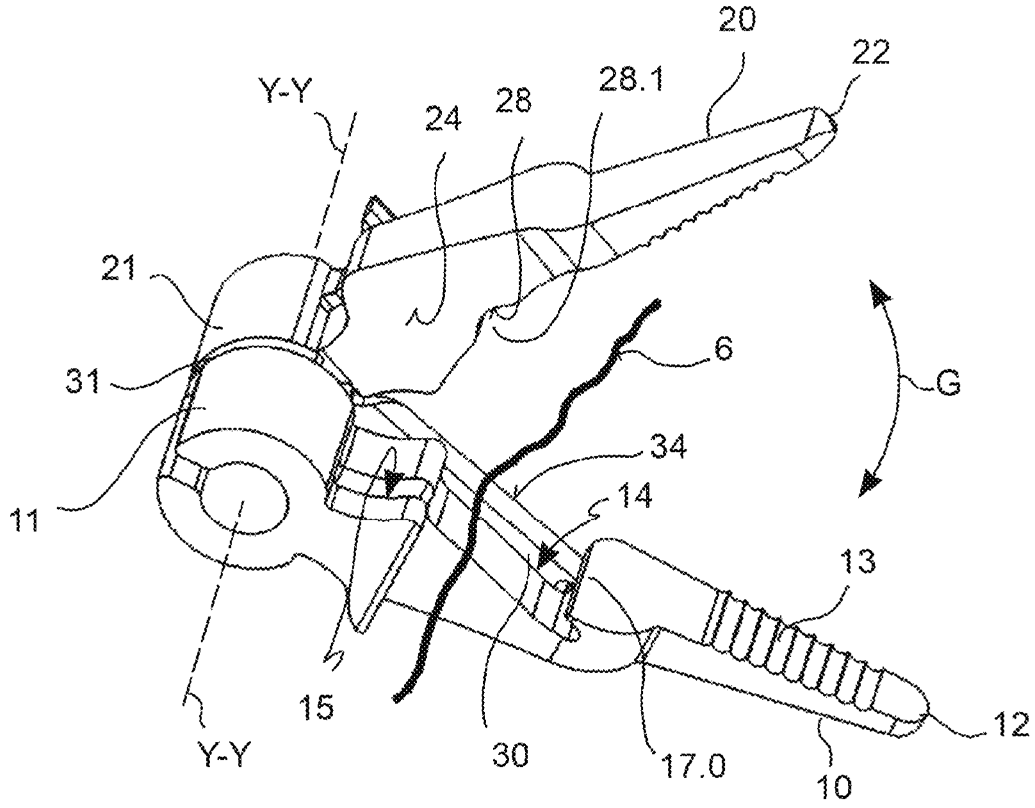
FIGS. 17A, 17B and 17C show a portion of the end-effector in FIG. 11 in a possible cutting sequence of a suture wire.
Figure 17B:
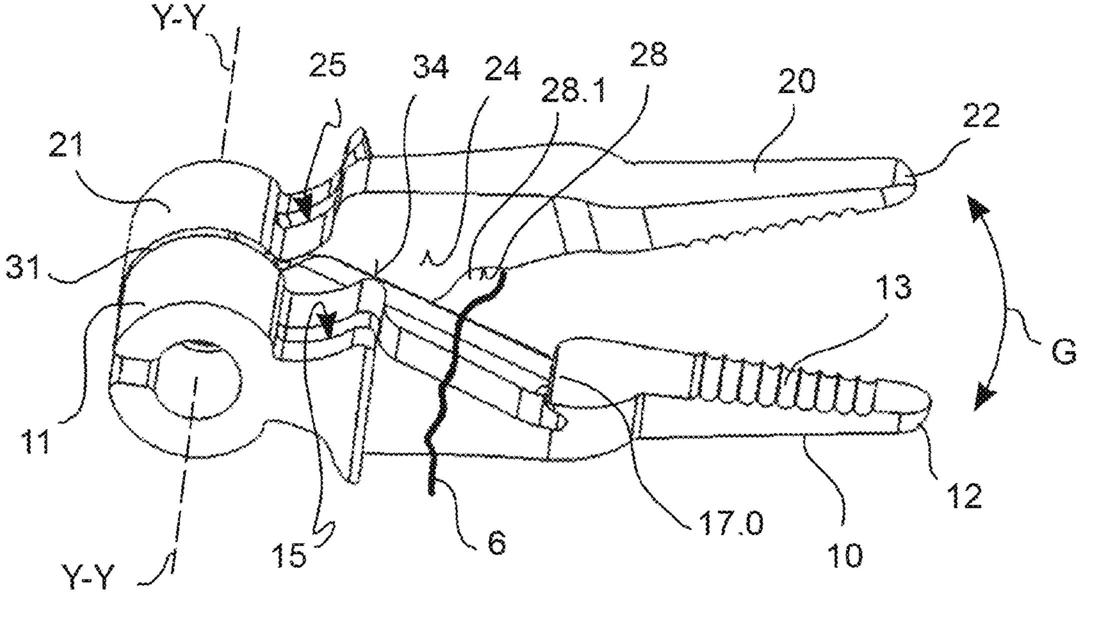
Figure 17C:
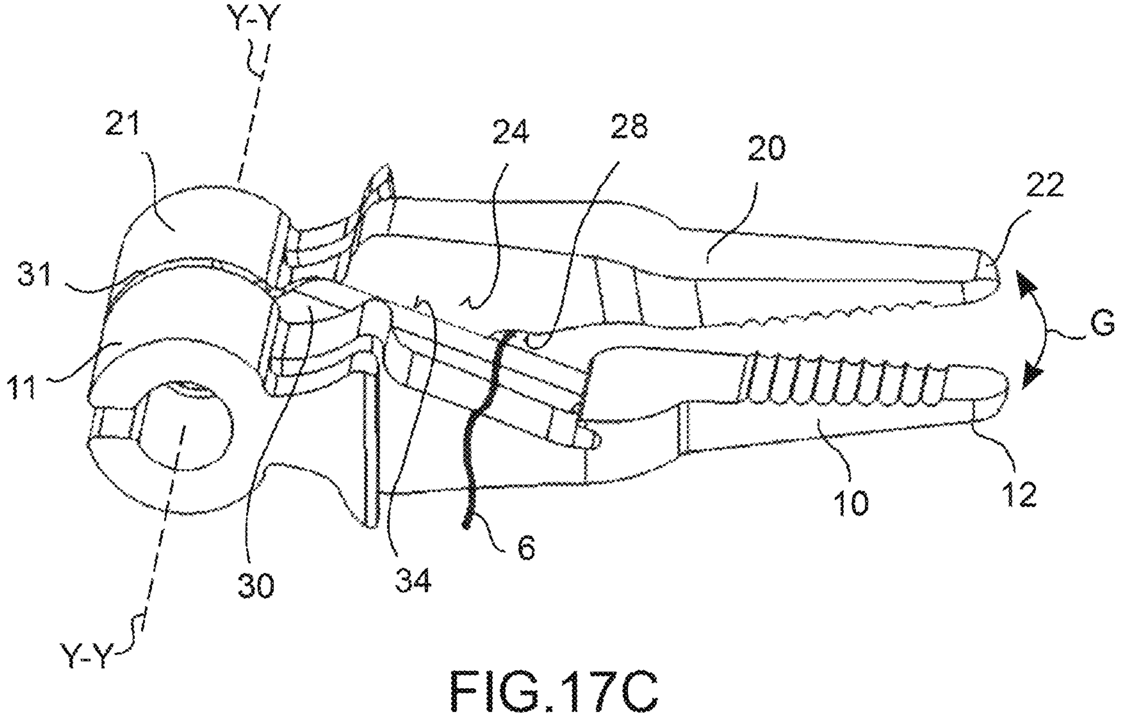

The at least one point of contact POC between the cutting edge 34 and the counter-blade surface 24 preferably varies in position and/or size as a function of the opening angle of the degree of freedom of opening/closing G (grip G), as diagrammatically shown for example in FIG. 14. In particular, at relatively high opening angles (for example an angle in the range 20°-30°) the contact occurs in a more proximal portion of the cutting edge 34, i.e., closer to the third attachment root 31, and gradually the opening angle is reduced as the contact moves in the distal direction, accentuating the bending by elastic deformation of the body of the blade link 30 with respect to the third root 31 of the blade link 30. Therefore, the deformed configuration of the blade link 30 when the first tip link 10 and the second tip link 20 are in a substantially closed configuration is maximally bent, and in any case more bent than the deformed configuration of the blade link 30 when the first link tip 10 and the second tip link 20 are in a partially closed and partially open configuration. Preferably, when the opening angle is maximally open and the blade is free, the blade is straight the blade link has a substantially planar configuration.

In order to move the links of the articulated end-effector 9 about said common axes of proximal and/or distal rotation i.e., pitch P-P and/or yaw Y-Y to activate the degrees of freedom of the articulated end-effector 9, preferably the surgical instrument of the needle-holder/cutter type 1 comprises a plurality of pairs of antagonistic actuation tendons extending from the backend portion 61 to the articulated end-effector 9 through the shaft 9 and ending on at least some of the links of the articulated end-effector 9, as explained below.

In accordance with a preferred embodiment, the first tip link 10 comprises in a single piece a first termination seat 15 which receives a first pair of antagonistic tendons 71, 72, and the second tip link 20 comprises in a single piece a second termination seat 25 which receives a second pair of antagonistic tendons 73, 74. Those skilled in the art will appreciate that in this preferred embodiment, each of said first and second pairs of antagonist actuation tendons comprises an opening actuation tendon 71, 73 and a closing actuation tendon 72, 74. By creating the termination seats 15, 25 in a single piece with the respective tip link 10, 20, it is possible to keep the number of pieces small, facilitating assembly and favoring miniaturization. Furthermore, the third root 31 of the blade link 30 is allowed to be made very thin, or at least thin as the bendable portion, elastically simplifying the creation of the blade link 30 and at the same time allowing a fine characterization of the mechanical properties thereof functional to the cutting action. In addition, in accordance with a preferred embodiment, each termination seat 15, 25 acts as a termination seat for both antagonistic tendons of the respective pair of antagonistic tendons, helping to keep the number of operations to be performed on each of the tip links 10, 20 to a minimum, thus favoring miniaturization. Therefore, the third blade link 30 does not comprise any termination seat and is dragged in rotation by the first tip link 10. Where a fourth link 40 is present, it is dragged in rotation by the second tip link 20 and does not comprise any termination seat. Thereby, it is possible to keep the number of actuation tendons small, as well as to keep the number of termination seats to a minimum, thus favoring miniaturization.

In accordance with an embodiment, the first termination seat 15 of the first tip link 10 and the second termination seat 25 of the second tip link are each delimited by a cantilevered drag leg 77, 78 extending longitudinally from the respective root 11, 21 next to the elongated body of the respective tip link 10, 20, and in particular next to the respective link portion 81, 82. Thereby each termination seat 15, 25 of the first and second tip links 10, 20 are substantially radial slots, and preferably longitudinal slots, having a radially-facing bottom wall formed by the respective attachment root 11, 21.

Preferably, the extension of the cantilevered drag leg 77, 78 and the respective connecting portion 81, 82 between the respective back side D1, D2 and the respective gripping side P1, P2 is substantially identical, so as to face edge surfaces of the respective termination seat 15, 25 which are placed side by side at the same level and which act as stop and drag abutments for the respective termination of tendons 70 of each actuation tendon 71, 72, 73, 74 of the respective pair of antagonistic tendons. The tendon termination 70 of each actuation tendon can be an enlarged portion, for example formed by a knot or a boss, which abuts against said edge walls of the respective termination seat 15, 25. In other words, said edge walls of each termination seat 15, 25 comprise edge walls formed by the respective cantilevered drag leg 77, 78 and by the respective connecting portion 81, 82 facing the respective back side D1, D2 acting as closing drag edge walls, and opposite edge walls of the same respective cantilevered drag leg 77, 78 and of the respective connecting portion 81, 82 facing to be opposite, i.e., facing the respective gripping side P1, P2 acting as opening drag edge walls. Therefore, the edge walls of the termination seats 15, 25 are arranged as an undercut for the respective tendon termination 70 in the respective termination seat 15, 25, and each termination seat 15, 25 is a through termination seat and preferably having an access opening facing longitudinally towards the free end 12, 22 of the respective tip link 10, 20. The distal portions of each actuation tendon 71, 72, 73, 74 of said first and second pairs of antagonistic tendons therefore intersect, and/or overlap, in the respective termination seat 15, 25 to bring the respective tendon termination 70 to abut against the edge walls placed circumferentially undercut with respect thereto to exert the drag in rotation of the first tip or the second tip link 10, 20 in the opening and/or closing direction of the degree of freedom of opening/closing G.

In accordance with a preferred embodiment, the first root 11 of the first tip link 10 and the second root 21 of the second tip link 20 each comprise at least one pulley surface 79, 80 facing to be opposite with respect to the common rotation axis Y-Y which laps the respective drag seat 15, 25 from circumferentially opposite sides and which can continue within the respective termination seat 15, 25 forming the radially facing bottom wall thereof, i.e., facing to be opposite the common rotation axis Y-Y, so that a distal portion close to the respective tendon termination 70 of each of said first and second pairs of tendons 71, 72, 73, 74 winds on said at least one pulley surface 79, 80 which is a convex ruled surface with parallel generatrices to the rotation axis Y-Y.

In accordance with a preferred embodiment, the at least one pulley surface 79 of the first root 11 and the at least one pulley surface 80 of the second root 21 are all convex ruled surfaces with parallel generatrices and parallel to the common rotation axis Y-Y which do not comprise circumferential channels or grooves for guiding or retaining the tendons. The at least one pulley surface 79, 80 can be interrupted at a radial cutting channel 19, 29, where present.

Figure 4:
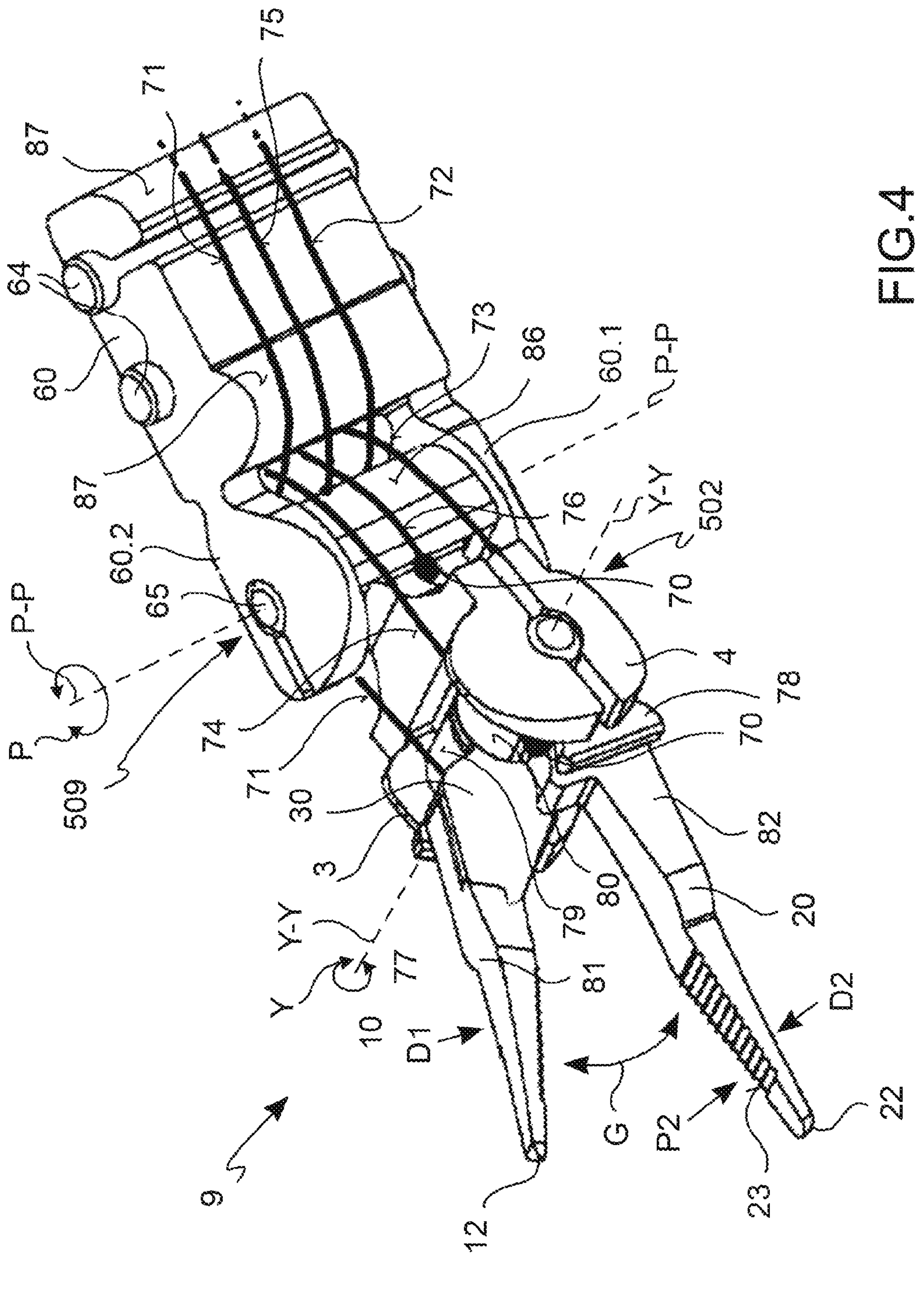
FIG. 4 shows an axonometric view of an end-effector of a surgical instrument of the needle-holder/cutter type according to an embodiment, in which the actuation tendons are diagrammatically shown.

In accordance with an embodiment in which said support link 2 which is articulated with respect to the distal end 8 of the shaft 7 is provided, the surgical instrument 1 of the needle-holder/cutter type further comprises a third pair of antagonistic tendons 75, 76 for moving the support link 2 about said common proximal rotation axis P-P. Therefore, the support link 2 can comprise at least a third termination seat 67 which receives the tendon terminations 70 of said third pair of antagonistic tendons 75, 76. In accordance with an embodiment as shown in FIGS. 3 and 4, for example, said at least a third termination seat 67 of the support link 2 is a single termination seat passing directly axially, i.e., parallel to the common distal rotation axis Y-Y through the body of the support link 2, which forms abutment and drag walls for the tendon terminations 70 placed as undercut for the respective actuation tendon 75, 76 of the third pair of tendons, similarly to what is explained above with reference to the first and second termination seats 15, 25. In accordance with an embodiment, the support link 2 comprises two separate and distinct third termination seats 67, one seat for each tendon 75, 76 of the third pair of antagonistic tendons.

In accordance with a preferred embodiment, the support link 2 comprises one or more convex ruled surfaces 84, 86 with parallel generatrices and all parallel to the common proximal rotation axis P-P, and the actuation tendons 71, 72, 73, 74 of the first and second pairs of antagonistic tendons slide on said one or more convex ruled surfaces 84, 86 of the support link 2 during the actuation of the first and/or second tip link 10, 20, in which said one or more convex ruled surfaces 84, 86 of the support link 2 do not comprise guide channels or grooves for receiving and guiding the tendons. The support link 2 can also comprise one or more convex ruled surfaces parallel to the common distal rotation axis Y-Y (not shown in the figure) on which the actuation tendons 71, 72, 73, 74 of the first and second pairs of antagonistic tendons slide during the actuation of the first and/or second tip links 10, 20.

The same one or more convex ruled surfaces 84, 86 with parallel generatrices and all parallel to the common proximal rotation axis P-P of the support link 2 can also act as a pulley surface for the actuation tendons 75, 76 of the third pair of antagonistic tendons, where the support link 2 is articulated with respect to the distal end 8 of the shaft 7 about the common proximal rotation axis P-P. Said one or more convex ruled surfaces 84, 86 of the support link 2 extend on opposite sides of the support link 2. In accordance with an embodiment, the pulley surface for the actuation tendons 75, 76 of the third pair of antagonistic tendons is formed by the internal surface of the termination seat 67 of the support link 2.

In accordance with an embodiment, in which said connection link 60 is provided, the connection link 60 comprises one or more convex ruled surfaces 85, 87 with parallel generatrices and all parallel to the common proximal rotation axis P-P, in which the actuation tendons 71, 72, 73, 74, 75, 76 of said first, second and third pairs of antagonistic tendons slide on said one or more convex ruled surfaces 85, 87 of the connection link 60. Said one or more convex ruled surfaces 85, 87 of the connection link 60 extend on opposite sides of the connection link 60 and between the connection link 60 and the support link 2 the tendons 71, 72, 73, 74, 75, 76 of each of said first, second and third pairs of antagonistic tendons mutually cross to slide or wrap without sliding on one or more convex ruled surfaces 84, 86 of the support link 2 facing to be opposite with respect to the ruled surface 85, 87 of the connection link 60 on which they slide proximally. For example, said one or more convex ruled surfaces 84, 86 of the support link 2 are interposed between the prongs 60.1, 60.2 of the link 60 and are oriented opposite with respect to the common proximal rotation axis P-P.

The convex ruled surfaces 79, 80, 84, 85, 86, 87 with parallel generatrices of the links in sliding or winding contact with the tendons 71, 72, 73, 74, 75, 76 are preferably all external surfaces for the respective link.

The actuation tendons 71, 72, 73, 74, 75, 76 are preferably polymer tendons formed by intertwined polymer fibers.

In accordance with a preferred embodiment, the group formed by said first root 11 of the first tip link 10, and said second root 21 of the second tip link 20, and said third root 31 of the blade link 30 is overall interposed between said two prongs 3, 4 of the support structure and in direct and intimate contact therewith. Thereby, relative movements between the roots and between each root and the prongs are avoided, and therefore where the articulation pin 5 is provided, relative sliding along the articulation pin 5 between the roots and the prongs are avoided during the elastic deformation of the blade link 30. In other words, the roots and the prongs are preferably placed side by side and in direct and intimate contact with each other and there are no elastic reactions therebetween, even if distally, i.e., at a certain longitudinal distance with respect to the common rotation axis Y-Y the geometric conformation of the respective links imposes that the rotational approaching dimensions of the respective links can overlap and/or interfere, as for example can occur for the gripping contact between the first gripping surfaces 13 of the first tip link 10 and the second gripping surface 23 of the second tip link 20, as well as for the cutting interference contact between the cutting edge 34 of the blade link 30 and the counter-blade surface 24 integral in rotation with the second tip link 20.

Similarly, the counter-blade surface 24 can overlap at least in part with the rotational approaching footprint of the body of the first tip link 10 and the body of the blade link 30 when in an elastically deformed configuration it translates locally with respect to the rotational footprint of the first tip link 10 in a direction transverse to the longitudinal extension direction of the body of the first tip link 10, although in accordance with a preferred embodiment, the counter-blade surface 24 and the surface 18 facing axially inwards of the first link tip 10 are geometrically shaped so as not to overlap in the respective rotational footprint.

In accordance with an embodiment, where there is a counter-blade surface 24 made in a separate piece with respect to the second tip link 20 and in particular belonging to a counter-blade link 40 having a fourth proximal attachment root 41, then the group formed by said first root 11 of the first tip link 10, and said second root 21 of the second tip link 20, and said third root 31 of the blade link 30, and said fourth root 41 of the counter-blade link 40 is overall interposed between said two prongs 3, 4 of the support structure and in direct and intimate contact therewith.

By virtue of such a package arrangement of the roots, a reaction is provided to the elastic bending of the blade body during the cutting action, meanwhile avoiding providing elements which exert an elastic action between the roots, consequently simplifying the assembly and favoring an extreme miniaturization.

By virtue of such a pack arrangement of the roots, impingements of the third root 31 of the blade link 30, which is preferably thinner, with respect to the articulation pin 5 are avoided so as to provide a satisfactory certainty of positioning the cutting edge 34 with respect to the counter-blade surface 24 for each opening angle of the degree of freedom of grip G, thus providing extreme cutting precision. Similarly, this can apply to the fourth root 41 of the counter-blade link 40, if provided.

A distal rotational joint 502 is thus allowed to be made axially rigid, i.e., rigid in the direction of the rotation axis Y-Y.

Figure 5A:
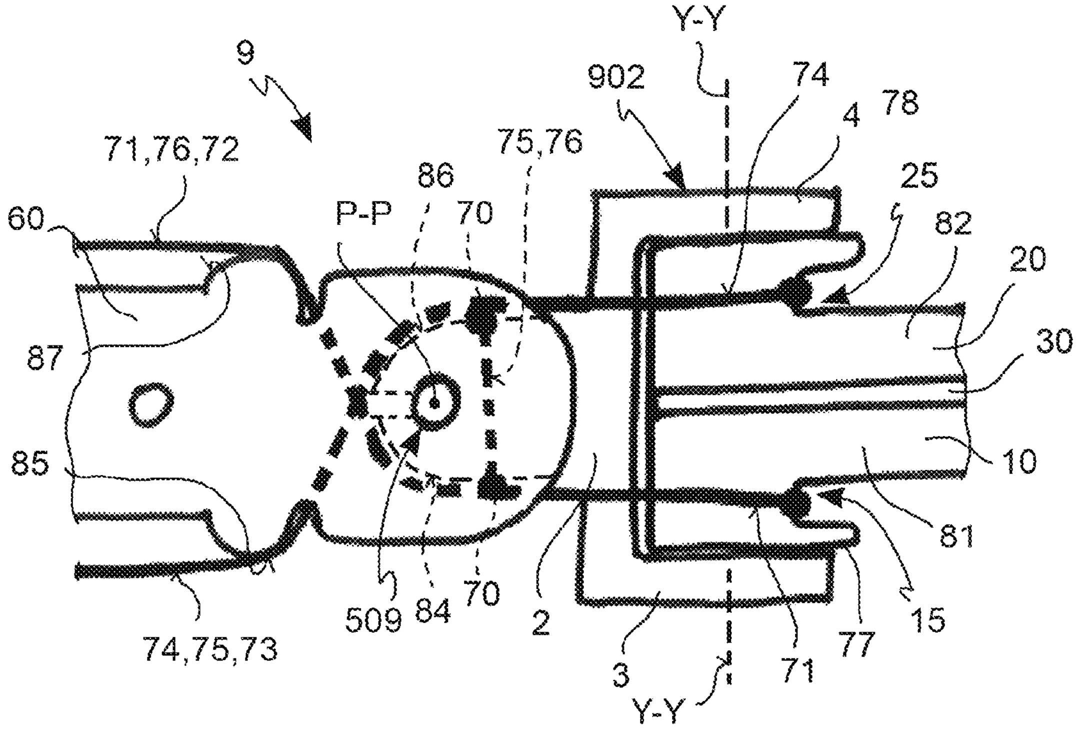
FIGS. 5A and 5B diagrammatically show an end-effector portion of a surgical instrument of the needle-holder/cutter type in two operating configurations, respectively, according to an embodiment, in which the actuation tendons are diagrammatically shown.
Figure 5B:
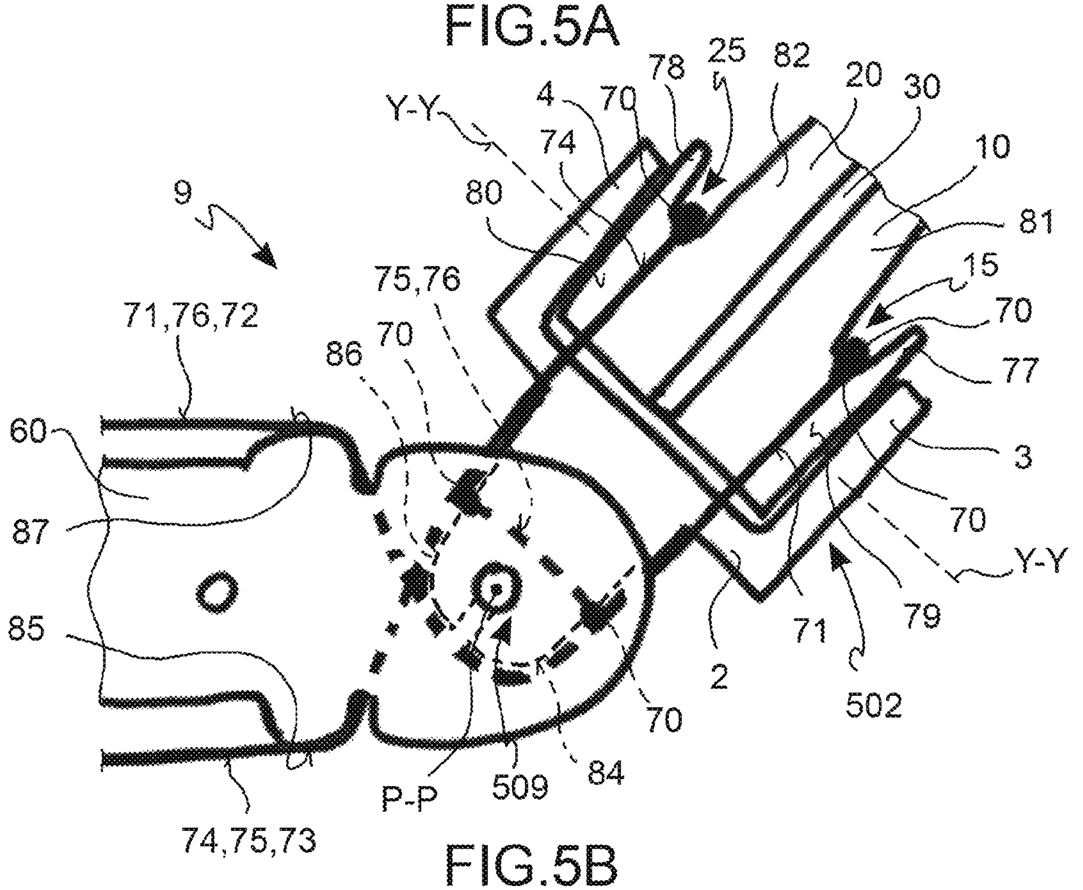
Figure 6:
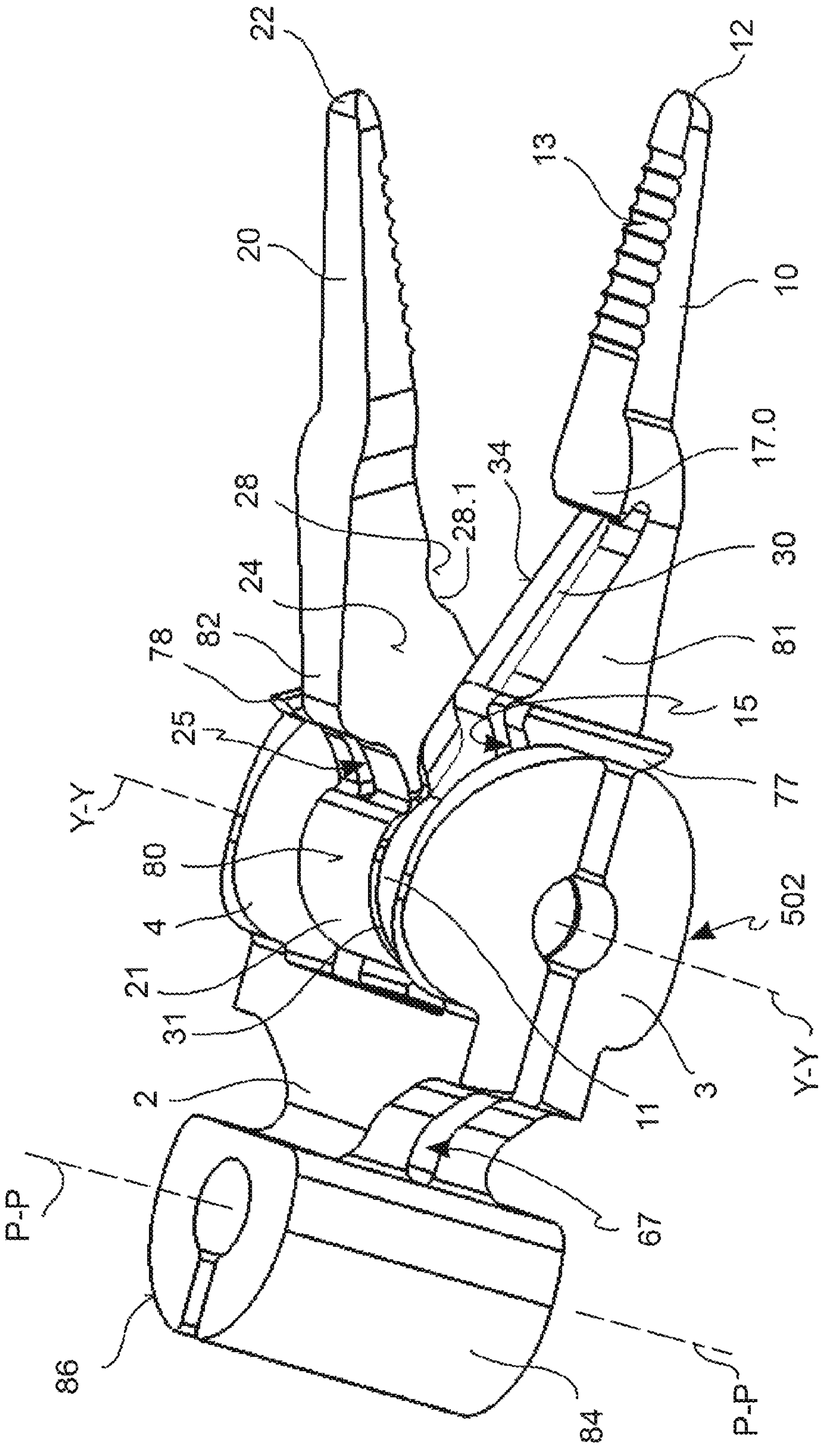
FIG. 6 shows an axonometric view of a portion of an end-effector of a surgical instrument of the needle-holder/cutter type, according to an embodiment.
Figure 7:
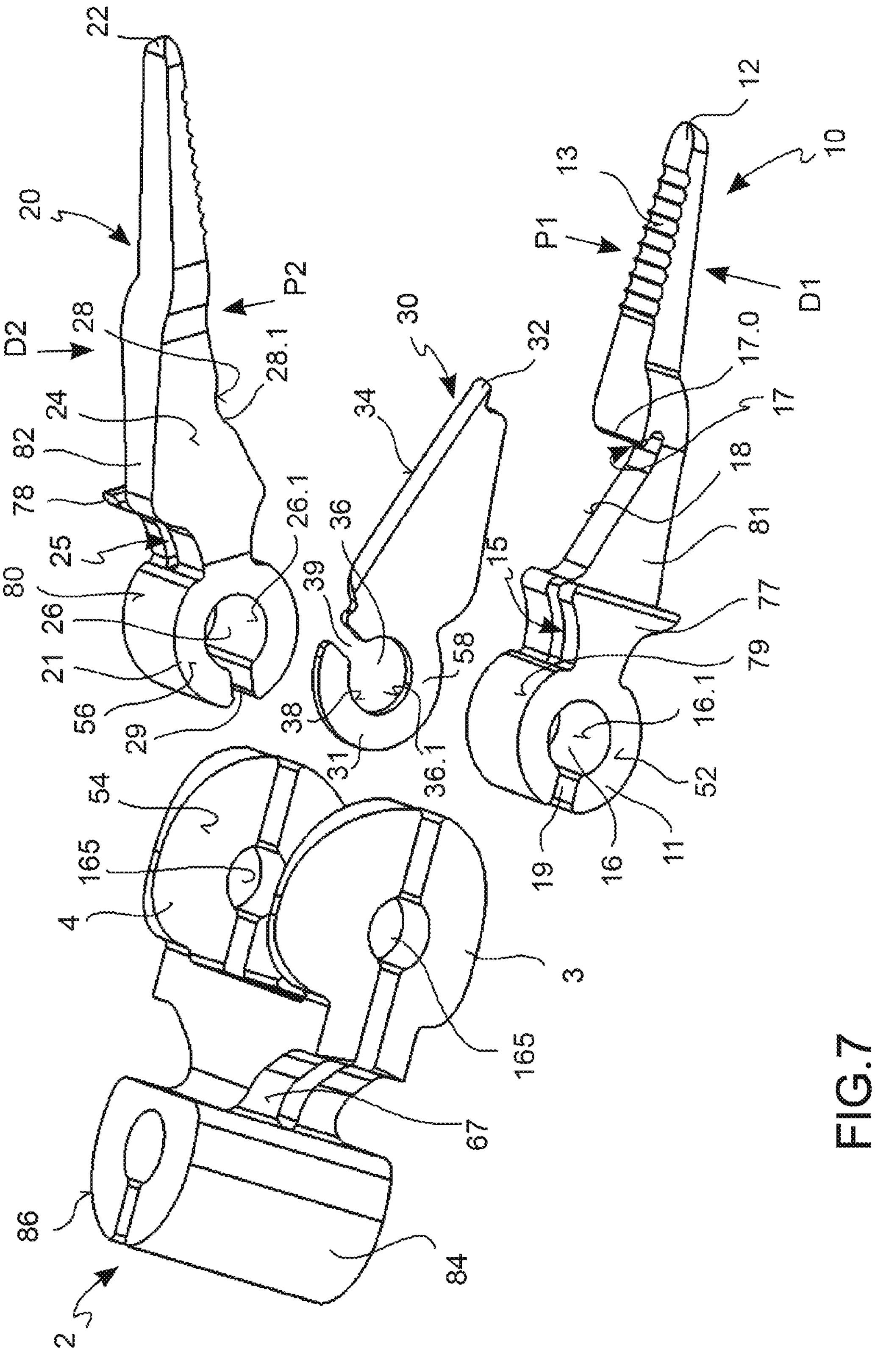
FIG. 7 shows an axonometric view of the portion of the end-effector in FIG. 6 with separate parts.

In accordance with an embodiment, as diagrammatically shown in FIGS. 5A and 5B, the actuation tendons 71, 72, 73, 74 of the pairs of antagonistic tendons adapted to activate the distal rotational joint 502 of the end-effector 9 and slide longitudinally on one or more convex ruled surfaces 85, 87 of the connection link 60, and slide longitudinally on one or more convex ruled surfaces 84, 86 of the support link 2. In other words, the sliding of the actuation tendons on the ruled surfaces occurs in the longitudinal extension direction of the tendons themselves 71, 72, 73, 74. The path of each tendon 71, 72, 73, 74 is stationary with respect to the convex ruled surfaces on which it slides, i.e., although each tendon slides longitudinally, it does not slide axially, and the longitudinal extension direction of each tendon does not vary in any operating condition. In addition, preferably the actuation tendons 71, 72, 73, 74 of the pairs of antagonistic tendons adapted to activate the distal rotational joint 502 of the end-effector 9 comprise a first pair of tendons 71, 72 terminated on the root 11 of the first tip link 10 and a second pair of tendons 73, 74 terminated on the root 21 of the second tip link, in which the first pair of tendons 71, 72 winds without sliding longitudinally on said pulley surface 79 formed by one or more convex ruled surfaces 79 with parallel generatrices to the distal rotation axis Y-Y, and in which the second pair of tendons 73, 74 winds without sliding longitudinally on said pulley surface 80 formed by one or more convex ruled surfaces 80 with parallel generatrices to the distal rotation axis Y-Y.

Meanwhile, the convex ruled surfaces 85, 87 of the connection link 60, and the convex ruled surfaces 84, 86 of the support link 2 lack guide channels or grooves for keeping the tendon inside a guide groove. The geometric relationship between the termination seats 15, 25 of the tendons 71, 72, 73, 74 and the ruled surfaces 79, 80, 84, 85, 86, 87 on which the actuation tendons of the distal rotational joint 502 slide longitudinally or wind without sliding favors the stationarity of the path of each tendon even in the absence of guide channels, or grooves on the body of the links of the end-effector 9. In addition, the absence of guide channels or grooves to guide the tendons allows to keep the contact surface between the cross-section of each tendon and the convex ruled surface on which it slides reduced to a minimum, while keeping the sliding friction reduced to a minimum.

In accordance with an embodiment, as diagrammatically shown in FIGS. 5A and 5B, the antagonistic actuation tendons 75, 76 adapted to activate the proximal rotational joint 509 of the articulated end-effector 9 terminate on the support link 2 and do not slide longitudinally with respect to the support link 2, i.e., they do not slide longitudinally on said one or more ruled surfaces 84, 86 of the support link 2, but wind thereabout without sliding, while they slide longitudinally on said one or more ruled surfaces 85, 87 of the link 60 to move the proximal rotational joint 509. Preferably, the body of the support link 2 comprises in a single piece at least a third termination seat 67 for receiving the third pair of antagonistic actuation tendons 75, 76. Therefore, the longitudinal extension of the tendons is locally orthogonal to the lines generating the ruled surfaces on which the tendons are locally in contact.

The distal rotational joint 502 is capable of causing a cutting action. The cutting edge 34 of the blade link 30 is adapted to abut against said counter-blade surface 24 integral in rotation with the second tip link 10, during the movement of the degree of freedom of opening/closing G in a mechanical interference contact condition to exert a cutting action. Thereby, the elasticity in axial direction for obtaining the cutting action is provided at least partially by the elasticity of the blade link 30, while the distal rotational joint 502 to which the third root 31 of the blade link 30 is articulated, is axially rigid, i.e., it is not elastically loaded because relative displacements between the prongs 3, 4 and the roots 11, 21, 31 on the distal rotation axis Y-Y are avoided.

Preferably, the axial distance Y5 in a direction parallel to the common distal rotation axis Y-Y between the first termination seat 15 of the root 11 of the first tip link 10 and a surface 84 of said one or more convex ruled surfaces 84, 86 of the support link 2 is constant for any cutting condition. Likewise, the axial distance Y5' in a direction parallel to the common distal rotation axis Y-Y between the second termination seat 25 of the root 21 of the second tip link 20 and a surface 86 of said one or more convex ruled surfaces 84, 86 of the support link 2 is constant for any cutting condition. I.e., as the opening angle of the degree of freedom of opening/closing G varies, the axial distance Y5, Y5' between a convex ruled surface 84, 86 of the support link 2 and a termination seat 15, 25 of the first or second pair of tendons 71, 72, 73, 74 remains the same.

In accordance with an embodiment, said first distance Y5 is zero i.e., the termination seat 15 is longitudinally aligned with a convex ruled surface 84 of the support link 2. In such a case, the actuation tendons 71, 72 of the first tip link 10 can have respective distal paths parallel to each other. Similarly, in accordance with an embodiment, said second distance Y5' is zero i.e., the termination seat 25 is longitudinally aligned with a convex ruled surface 86 of the support link 2. In such a case, the actuation tendons 73, 74 of the reaction link 20 can have respective distal paths parallel to each other.

In accordance with a preferred embodiment, the axial distance Y5 between the first termination seat 15 of the root 11 of the link 10 and a surface 84 of said one or more convex ruled surfaces 84, 86 of the support link 2 is equal to the axial distance Y5' between the second termination seat 25 of the root 21 of the link 20 and a surface 86 of said one or more convex ruled surfaces 84, 86 of the support link 2.

Therefore, avoiding axial sliding along the articulation pin 5 between the roots, as well as between the roots and the prongs, keeps the geometric relationship between the ruled surfaces 84, 86 of the support link 2 on which the tendons 71, 72, 73, 74 of the first or second pair of tendons slide longitudinally to actuate the degree of freedom of opening/closing G, i.e., to exert the cutting action and the termination seats 15, 25 for the respective tendons made in a single piece with the root 11 of the link 10 or the root 21 of the link 20, respectively, without thereby preventing the relative rotation between said links about the common distal rotation axis Y-Y.

In the direction parallel to the rotation axis the tendons do not slide with respect to the respective ruled surfaces thereof.

It thus allows making an axially rigid rotational joint 502 of a cutting joint. A blade having a cutting edge 34 and a counter-blade surface 24 which are integral in rotation with the axially rigid rotational joint 502 are provided, capable of jointly exerting a cutting action during the closing movement of the degree of freedom of opening/closing. Therefore, it is possible to avoid the provision of elastic elements of the Belleville type fitted to the articulation pin 5 or otherwise interposed between the prongs 3, 4 of the support structure. In addition, the provision of an adjustment screw adapted to tighten the roots together in an axial direction is avoided.

Said axially rigid distal rotational joint 502 also allows the cutting edge 34 to be oriented by rotating it about the rotation axis of yaw Y-Y, allowing control over the adjustment of the cutting orientation.

Such a distal rotational joint 502 is axially rigid also for any orientation of the degree of freedom of yaw Y, i.e., for any movement of the group formed by the first tip link 10, the blade link 30 and the second tip link 20 with respect to the support structure, as well as when present for any orientation of the degree of freedom of pitch P of the proximal rotational joint 509, i.e., for any movement of the group formed by the support link 2, and first tip link 10, the blade link 30 and the second tip link 20 with respect to the link 60 to the shaft 7. Preferably, the connection link 60 to the shaft is rigidly fixed to the distal end 8 of the shaft 7, for example by means of a pair of pins 94, and in this case the degree of freedom of pitch P can be understood as an orientation of the support link 2 with respect to the shaft 7 particularly where the shaft 7 is a rigid shaft.

Preferably, the distance between the prongs 3, 4 of the support structure remains constant for any cutting condition and the prongs remain in direct and intimate contact with the respective surfaces of the first root 11 and the second root 21.

Preferably, therefore, the first root 11 of the first tip link 10 comprises a first external contact surface 52 and the first prong 3 of the support structure comprises a first internal contact surface 53, said first external contact surface 52 of the first root 11 is in contact with said first internal contact surface 53 of the first prong 3, and in which the second root 21 of the second tip link 20 comprises a second external contact surface 55 and the second prong 4 of the support structure comprises a second internal contact counter-surface 54, said second external contact surface 55 of the second root 21 is in contact with said second internal contact counter-surface 54 of the second prong 4.

Figure 30:
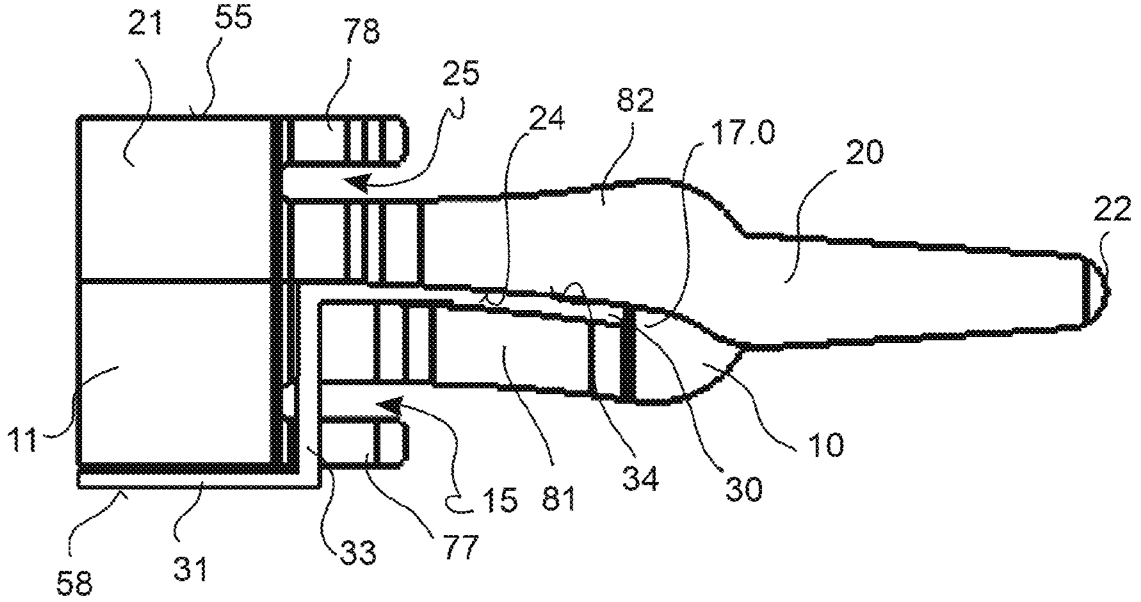
FIG. 30 shows a plan view in cutting configuration of a portion of an end-effector of a surgical instrument of the needle-holder/cutter type, according to an alternative embodiment.

In accordance with an embodiment as shown in FIG. 30, for example, the third root 31 of the blade link 30 is interposed between and in direct and intimate contact with the first prong 3 of the support structure and the first root 11 of the first tip link 10. The provision of a transverse bridge 33 in the body of the blade link 30 which crosses the rotational approaching footprint of the body of the first tip link 10 brings the cutting edge 34 into contact position with the counter-blade surface 24 integral in rotation with the second tip link 20, i.e., between the first tip link 10 and the second tip link 20. In other words, the transverse bridge 33 can cross the connecting portion 81 of the elongated body of the first tip link 10 and/or the first root 11 of the first tip link 10. In such a case, the first internal contact surface 51 of the first root 11 is in contact with the second internal contact surface 56 of the second root 21, and in which the first external contact surface 52 of the first root 11 is in contact with the second contact surface 57 of the third root 31, and in which the first contact surface 53 of the first prong 3 is in contact with the first contact surface 58 of the third root 31. In accordance with this embodiment, therefore, the blade with the cutting edge 34 remains interposed between the first and second tip links, while the third root 31 of the blade link 30 is interposed between the first prong 3 of the support structure and the first root 11 of the first tip link 10.

Figure 11:
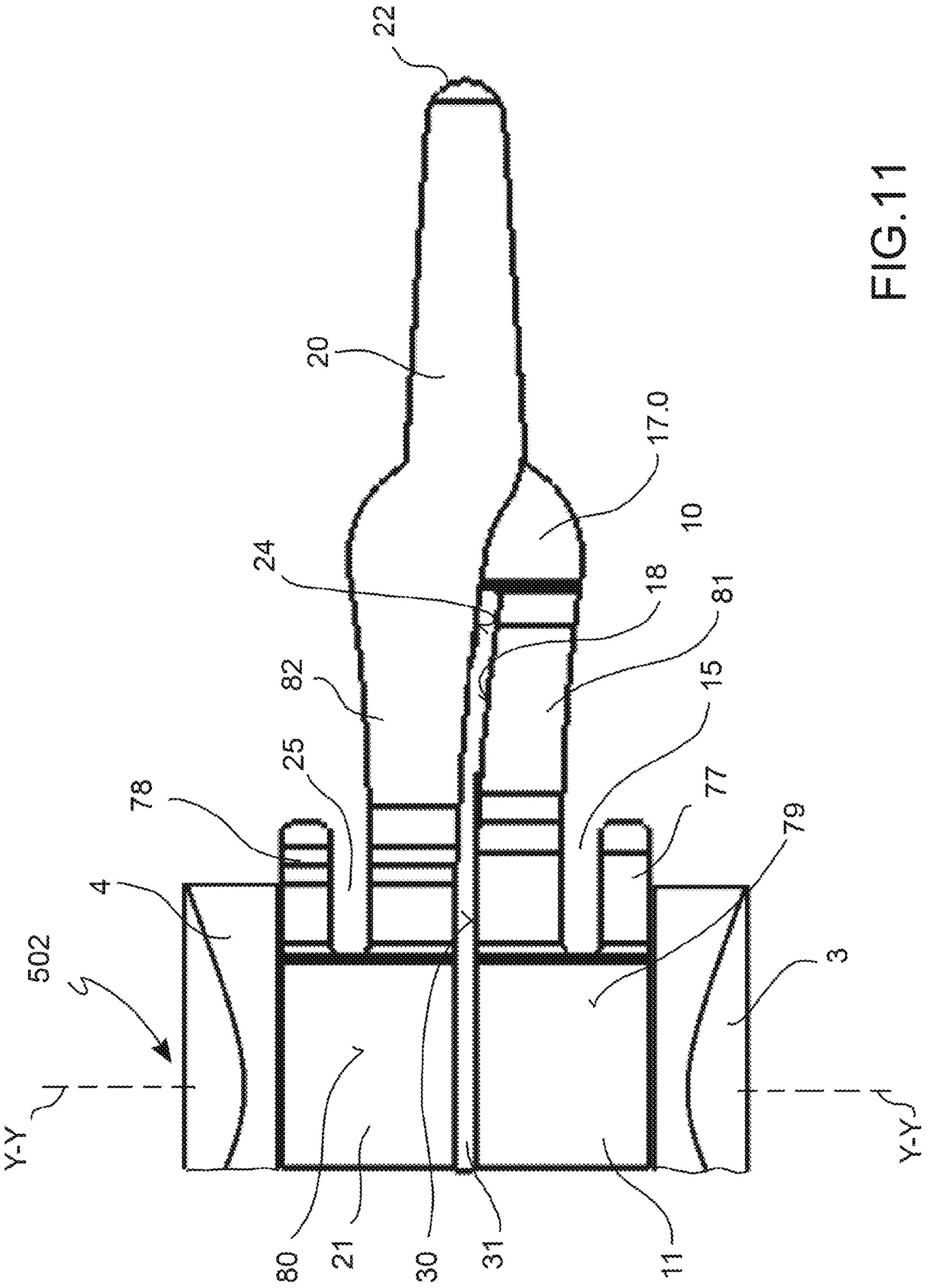
FIG. 11 shows a plan view of the portion of the end-effector in FIG. 10 in an assembled and cutting configuration.

In accordance with a preferred embodiment as shown in FIG. 11, for example, the third root 31 of the blade link 30 is interposed between said first root 11 of the first tip link 10 and said second root 21 of the second tip link 20, and in direct and intimate contact therewith, to provide a reaction to the elastic bending of the blade 34 of the blade link 30 during the cutting action. Contacting the third root of the blade link between said first root 11 of the first tip link 10 and said second root 21 of the second tip link 20 determines that during the elastic deformation of the body of the blade link 30 in the direction of the thickness thereof carried out from the interference contact of the cutting edge 34 with the counter-blade surface 24, the third root 31 of the blade link 30 does not deform with respect to the first root 11 and the second root 21 because it is constrained with respect to the deformation in the direction of the common axis rotation Y-Y between the first root 11 of the first tip link 10 and the second root 21 of the second tip link 20.

Preferably, therefore, the first root 11 of the first tip link 10 comprises a first internal contact surface 51 and the third root 31 of the blade link 30 comprises a first contact surface 58, said first internal contact surface 51 of the first root 11 is in contact with the first contact surface 58 of the third root 31, and in which the second root 21 of the second tip link 20 comprises a second internal contact surface 56 and the third root 31 of the blade link 30 comprises a second contact surface 57 or contact surface facing the counter-blade 57, said second internal contact surface 56 of the second root 21 is in contact with said second contact surface 57 of the third root 31.

In accordance with a preferred embodiment, all said contact surfaces of the roots 11, 21, 31 and of the prongs 3, 4 are parallel to one another and preferably are all orthogonal to the common rotation axis Y-Y. Preferably, in each configuration of the degree of freedom of opening/closing G all of said contact surfaces of the roots 11, 21, 31 and of the prongs 3, 4 always remain parallel with one another and in direct and intimate contact with one another.

In accordance with an embodiment, where a counter-blade surface 24 made in a separate piece with respect to the second tip link 20 is present, and in particular belonging to a counter-blade link 40 having a fourth proximal attachment root 41, then the third root 31 of the blade link 30 is axially interposed between said first root 11 of the first tip link 10 and said fourth root 41 of the counter-blade link 40, and in direct and intimate contact therewith, and in which said fourth root 41 of the counter-blade link 40 is axially interposed between said third root 30 of the blade link 30 and said second root 21 of the second tip link 20 and in direct and intimate contact therewith, to provide a reaction to the elastic bending of the blade of the blade link 30 during the cutting action. Therefore, according to this embodiment, said fourth root 41 of the counter-blade link 40 comprises two opposite contact surfaces 59, 66, so that said first, second, third and fourth roots 11, 21, 31, 41 and said prongs 3, 4 comprise respective contact surfaces 51, 52, 53, 54, 55, 56, 57, 58, 59, 66 turned axially which are all parallel to one another.

The roots preferably have a cylindrical geometry about the common rotation axis Y-Y, and where the third root 31 has a substantially smaller thickness with respect to the first root 11 and the second root 21, the third root 31 has a discoidal-type cylindrical geometry. Similarly, this can apply to the fourth root 41 of the counter-blade link 40, if provided.

Although the manufacture of the pieces by means of a wire electro-erosion process allows obtaining boosted tolerances, minimum local micro-clearances can be provided in the direction of the common rotation axis Y-Y of the order of a fraction of a tenth of a millimeter between at least some of said contact surfaces of the roots and/or the prongs to ensure a direct and intimate contact and at the same time allow the relative rotation about the common rotation axis Y-Y during the actuation of the degree of freedom of grip G and/or yaw Y. The articulation pin 5 can be in interference, i.e., integral in rotation with at least one of said roots and/or said prongs.

In particular, as a consequence of the fact that the support structure with two prongs 3, 4, the first root 11 of the first tip link 10, the second root 21 of the second tip link 20 and the third root 31 of the blade link 30 are made in separate pieces, however a minimum micro-clearance is necessarily provided in the axial direction, i.e., in the direction of the common rotation axis Y-Y between the respective contact surfaces, and said micro-clearance as a whole is in accordance with an embodiment in a range between 1/20 and 1/5 of the thickness of the third root 31 of the blade link 30 and is divided, i.e., locally distributed between the contact surfaces of the prongs 3, 4 and the roots of the respective links, where the contact surfaces of the prongs 3, 4 and of the first and second roots 11, 21 respectively of the first and second tip links 10, 20 are made by wire electro-erosion (WEDM).

Therefore, the wording "direct and intimate contact" also intends to indicate the embodiments in which a minimum micro-clearance is in any case provided between at least some of, but also all, the contact surfaces of the prongs of the support structure and of the roots of the respective links. During the cutting action and in particular for relatively high opening angles of the degree of freedom of opening/closing G (e.g., angle of about 20°-30° between the gripping surfaces 13, 23), the mechanical interference contact between the cutting edge 34 of the blade link 30 and the counter-blade surface 24, therefore, can generate a minimum micro-displacement of the order of one hundredth of a millimeter of the third root along the articulation pin 5 as well as of the fourth root 41, when present.

For example, from an analysis conducted by the inventors, it emerges that in accordance with an embodiment the thickness of the third root 31 of the blade link 30 is about 0.2 mm and the overall micro-clearance in the direction of the common rotation axis Y-Y which is in operating conditions distributed locally between the contact surfaces of the prongs and the roots of the respective links is overall about 0.02 mm, and that when in operating conditions the local micro-clearance in the direction of the common rotation axis Y-Y between the third root 31 of the blade link 30 and the second root 21 of the second tip link 20 is about 0.01 mm, i.e., substantially equal to 1/20 of the thickness of the third root 31 of the blade link 30.

By virtue of the fact that the support structure with two prongs 3, 4, the first root 11 of the first tip link 10, the second root 21 of the second tip link 20 and the third root 31 of the blade link 30 are made in separate pieces imposing both a minimum clearance in the direction of the common rotation axis Y-Y as explained above, it allows maneuvering in opening/closing rotation said degree of freedom of opening/closing G in a precise and controlled manner both in the opening direction and in the closing direction, at the same time exerting the gripping action and/or the cutting action.

The articulation pin 5 can be made in the form of two opposite and aligned cantilevered legs in a single piece with the first root 11 of the first tip link 10 or in the form of two opposite and aligned cantilevered legs in a single piece with the second root 21 of the second tip link 20. Alternatively, the articulation pin 5 can be made in two pieces, a first piece in the form of two opposite and aligned cantilevered legs in a single piece with the first root 11 of the first tip link 10, and a second piece in the form of two opposite and aligned cantilevered legs in a single piece with the second root 21 of the second tip link 20, said first and second pieces of the articulation pin 5 being aligned along the common rotation axis Y-Y.

In accordance with a preferred embodiment, said first root 11 of the first tip link 10 comprises a first through hole 16, and said second root 21 of the second tip link 20 comprises a second through hole 26, and said third root 31 of the blade link 30 comprises a third through hole 36, in which said first through hole 16 of the first root 11, and said second through hole 26 of the second root 21, and said third through hole 36 of the third root 31 are aligned in axis with said common rotation axis Y-Y. In accordance with an embodiment, a articulation pin 5 is received inside said first, second and third through holes 16, 26, 36. In this case, said articulation pin 5 can be made as a cantilevered leg in a single piece with one of the prongs 3, 4 of the support structure, or it can be made in two pieces in the form of two opposite and aligned cantilevered legs each in a single piece with one of the prongs 3, 4 of the support structure, although in accordance with a preferred embodiment the articulation pin 5 is a separate piece both with respect to the roots 11, 21, 31, and with respect to the prongs 3, 4. In accordance with an embodiment, each of the two prongs 3, 4 comprises a through hole of the prong 165 aligned in axis with said common rotation axis Y-Y and aligned with each and all of said first, second and third through holes 16, 26, 36 respectively of the first, second and third root 11, 21, 31.

In accordance with an embodiment, said first through hole 16 of the first root 11, and said second through hole 26 of the second root 21, and said third through hole 36 of the third root 31 are all circular through holes and coaxial to said common rotation axis Y-Y and receive a single articulation pin 5 extending in the direction of the common rotation axis Y-Y from a first prong 3 of the support structure to a second prong 4 of the support structure. In accordance with an embodiment, said first through hole 16 of the first root 11, and said second through hole 26 of the second root 21, and said third through hole 36 of the third root 31 all have substantially the same diameter and receive said articulation pin 5 in direct and intimate contact for the entire circumferential extension of the respective hole edge 16.1, 26.1, 36.1.

The provision of said third circular through hole 36 of the third root 31 of the blade link 30 in direct and intimate contact with the articulation pin 5 for the entire circumferential extension of the hole edge 36.1 thereof, allows exerting a reaction to the cutting action exerted by the cutting edge 34 of the blade link 30. In particular, during the cutting action the opening angle of the degree of freedom of grip G is progressively reduced, determining a mechanical interference contact between the cutting edge 34 (and preferably also the blade surface 35) of the blade link 30 and the counter-blade surface 24 integral in rotation with the second tip link 20, and therefore a direct friction force in the opening direction is generated on the cutting edge 34 (and preferably also on the blade surface 35) of the body of the blade link 30 in contact with the counter-blade surface 24 which is balanced by a reaction to the friction of the cutting action exchanged in a portion of mutual contact between the hole edge 36.1 of the third through hole 36 of the third root 31 of the blade link 30 and the articulation pin 5. The friction reaction of the cutting action is preferably directed substantially along a radial direction with respect to the common rotation axis Y-Y. The reaction to the friction of the cutting action preferably affects an arc surface 38 of the thickness of the hole edge 36.1 of the third circular through hole 36 of the third root 31 of the blade link 30 facing the through hole 36.

In accordance with an embodiment, where there is a counter-blade surface 24 made in a separate piece with respect to the second tip link 20 and in particular belonging to said counter-blade link 40 having said fourth proximal attachment root 41, then said fourth root 41 of the counter-blade link 40 comprises a fourth through hole 43, in which said first through hole 16 of the first root 11, and said second through hole 26 of the second root 21, and said third through hole 36 of the third root 31, and said fourth through hole 43 of the fourth root 41 are all circular through holes and coaxial to said common rotation axis Y-Y and receive a single articulation pin 5 extending in the direction of the common rotation axis Y-Y from a first prong 3 of the support structure to a second prong 4 of the support structure. In accordance with an embodiment, said fourth through hole 43 of the fourth root 41 of the counter-blade link 40 has a hole edge 43.1 in direct and intimate contact with a articulation pin 5 for the entire extension of the hole edge, to exert with an arc surface thereof of the thickness of the hole edge a reaction to the friction exchanged between the blade link 30 and the counter-blade surface 24 of the counter-blade link 40 during the cutting action.

Where at least some, but also all, of the through holes of the roots are made by wire electro-erosion (WEDM), a radial cutting channel 19, 29, 39, 49 is provided on the respective root between the hole edge and the external edge of the respective root as an effect of the continuous cutting path of the cutting wire used for making the through holes by wire electro-erosion. Preferably, the arrangement of the radial cutting channel on the respective root is studied based on the static or dynamic behavior of the respective link, when in operating conditions. In particular, in accordance with a preferred embodiment, the cutting channel 39 of the root 31 of the blade link 30 is radially offset with respect to the cutting channel 29 of the second root 21 of the second tip link 20 as well as with respect to the cutting channel 49 of the fourth root 41 of the counter-blade link 40, to prevent the edges of the cutting channels from interlocking with each other during the opening/closing action.

In accordance with an embodiment, the through hole of the prong 165 of each of said two prongs 3, 4 is a circular through hole coaxial to said common rotation axis Y-Y. Where the prongs 3, 4 of the support structure are made by wire electro-erosion, at least one radial channel between the hole edge and the external edge of the respective prong can be provided on the prong.

In accordance with an embodiment, said counter-blade surface 24 can be made sloping in a direction which is transverse, preferably orthogonal, to the longitudinal extension of the body of the second tip link 20 and is also transverse, preferably orthogonal, to the common rotation axis Y-Y, i.e., in other words, said counter-blade surface 24 can be made sloping in the direction that joins the back side D2 with the gripping side P2 of the second tip link 20, preferably protruding more towards the back side D2. The counter-blade surface 24 is not necessarily made sloping, even while protruding.

In accordance with an embodiment, said counter-blade surface 24 is a curved surface. Thereby, the counter-blade surface 24 protrudes due to the arched shape thereof. The concavity of the counter-blade surface 24 is preferably axially and internally facing i.e., in a direction parallel to the common rotation axis Y-Y and facing the rotational footprint of the blade link 30.

The counter-blade surface 24 can act as a wedge to appropriately bend the cutting edge 34 and the blade link 30 to exert the cutting action substantially along the entire longitudinal extension of the counter-blade surface 24.

In accordance with an embodiment, the blade link 30 is substantially planar when in a non-deformed configuration, i.e., it lies on a definable lying plane. The bending elasticity of the blade link 30 tends to bring the blade link 30 back into said non-deformed planar configuration. Therefore, the blade surface 35 facing axially inwards can be parallel, and preferably also aligned for example seamlessly, to the second contact surface 57 of the third root 31 of the blade link 30. In other words, according to an embodiment, the definable lying plane of the blade link 30 is parallel to the second contact surface 57 of the third root 31 of the blade link 30 as well as parallel to the first contact surface 58 of the third root 31 of the blade link 30. Preferably, the cutting edge 34 is straight when in non-deformed condition i.e., extends substantially in a straight line parallel to, and preferably as a straight extension of, the second contact surface 57 of the third root 31 of the blade link 30. In other words, in accordance with an embodiment, the cutting edge 34 extends parallel to the definable lying plane of the blade link 30.

The cutting edge 34 of the blade link 30 can be aligned with the longitudinal extension direction X-X of the shaft 7 in at least one operating configuration, for example in the case in which the shaft 7 is a straight and rigid shaft and the cutting edge 34 is out of contact with a protruding portion of the counter-blade surface 24.

In accordance with an embodiment, a drag engagement arranged distally with respect to the common rotation axis Y-Y is provided for making the blade link 30 integral in rotation together with the first tip link 10. The drag engagement can be made along the longitudinal extension of the cutting edge 34 of the blade link 30 (not necessarily by interrupting the cutting edge 34) and is preferably made close to or at the distal end of the cutting edge 34 of the blade link 30. The drag engagement can be obtained by an engagement between the blade link 30 and the first tip link 10.

In accordance with an embodiment, said first tip link 10 comprises at least one drag surface 17.1, 17.2 to drag into ration the blade link 30 and preferably comprises an opening drag surface 17.2 and a closing drag surface 17.1. In accordance with an embodiment, said at least one drag surface 17.1, 17.2 of the first tip link 10 delimits a drag seat 17 which receives a drag portion of the blade link 30, to make said blade link 30 and said first tip link 10 integral in rotation. In this case, the at least one drag surface 17.1, 17.2 of the first tip link 10 comprises two opposite and facing dragging counter-surfaces 17.1, 17.2 to rotate the blade link 30 both in the opening direction and in the closing direction of the degree of freedom of opening/closing G, interfacing with two opposite drag counter-surfaces 37.1, 37.2 of the blade link 30. In such a case, the drag portion of the blade link 30 is preferably positioned away from the third root 31 of the blade link 30 so as to ensure precise drag, even though the drag portion of the blade link 30 can be positioned at the third root 31 to achieve a more advantageous mechanical transfer. The opening drag counter-surface 37.2 and the closing drag counter-surface 37.1 of the blade link 30 can be arranged on a single portion, for example as opposite surfaces of a single protrusion that can coincide with the distal end 32 of the blade link 30.

In accordance with an embodiment, the drag portion of the blade link 30 coincides with the distal end 32 of the blade link 30 and the drag seat 17 of the first tip link 10 is located distally with respect to the surface 18 facing axially inwards of the first tip link 10, i.e., with respect to the surface that can act as an abutment for the deformation of the blade. In such a case, the drag seat 17 has an axial extension such as to accommodate the distal end 32 of the blade link 30, thus receiving together with said deformation seat 14 the deformation of the blade link 30 during the cutting action. The distal end 32 of the blade link 30 can comprise a distal portion of said cutting edge 34, and in such a case said distal portion of said cutting edge 34 acts as a drag counter-surface in the opening direction 37.2 cooperating against a respective opening drag surface 17.2 of the first blade link 10. In accordance with an embodiment, proximally with respect to the first gripping surface 13 a drag tooth 17.0 extends proximally, i.e., towards the common rotation axis Y-Y, forming an undercut seat with respect to the first gripping surface 13 which opens proximally and extends axially, and forming the drag seat 17 which receives the distal end 32 of the blade link 30.

In accordance with an embodiment in which the drag portion of the blade link 30 coincides with the distal end 32 of the blade link 30, said distal end 32 of the blade link 30 is constrained in rotation with the first tip link 10 and is free to slide axially with respect to the tip link 10 inside a drag seat 17 during the elastic bending deformation during the cutting action.

Figure 28A:
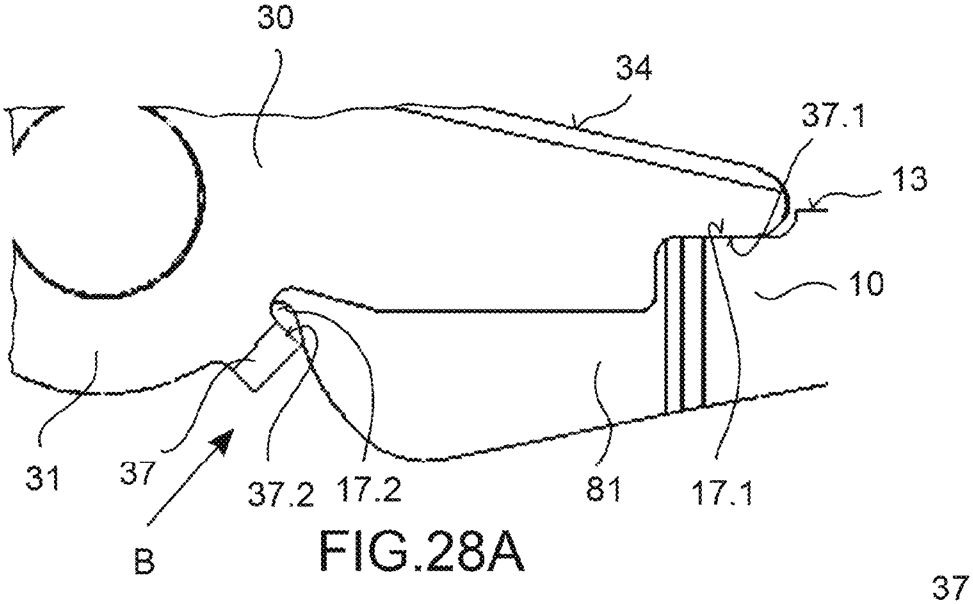
FIG. 28A shows a vertical elevation view of a portion of a first tip link of an end-effector of a surgical instrument of the needle-holder/cutter type, according to an embodiment.
Figure 28B:
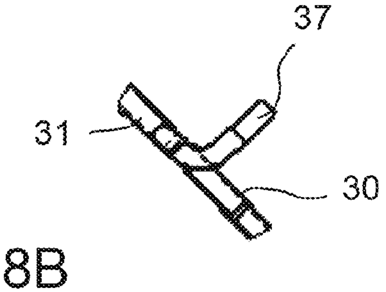
FIG. 28B is an enlargement of a detail of a blade link of FIG. 28A according to the point of view indicated by arrow B.
Figure 28C:
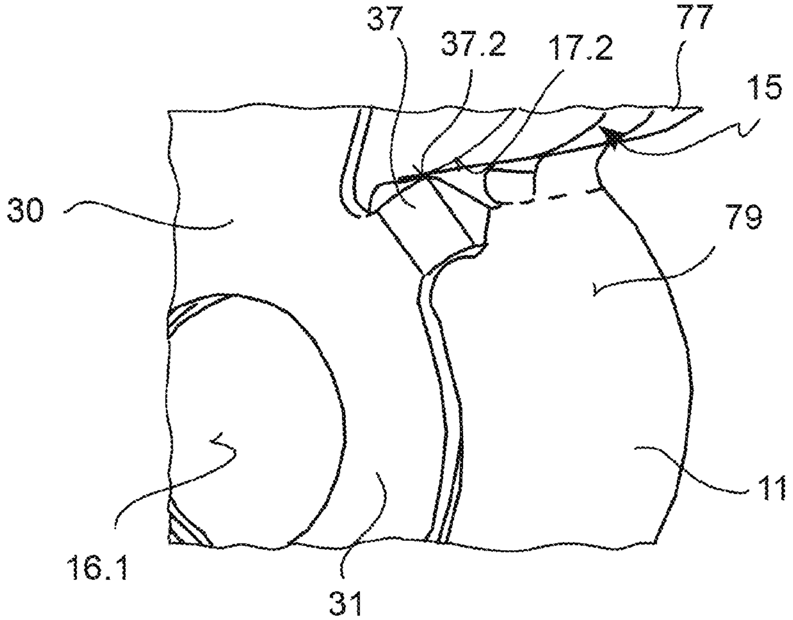
FIG. 28C shows in axonometry view a detail of the portion of the first tip link shown in FIG. 28A.
Figure 29A:
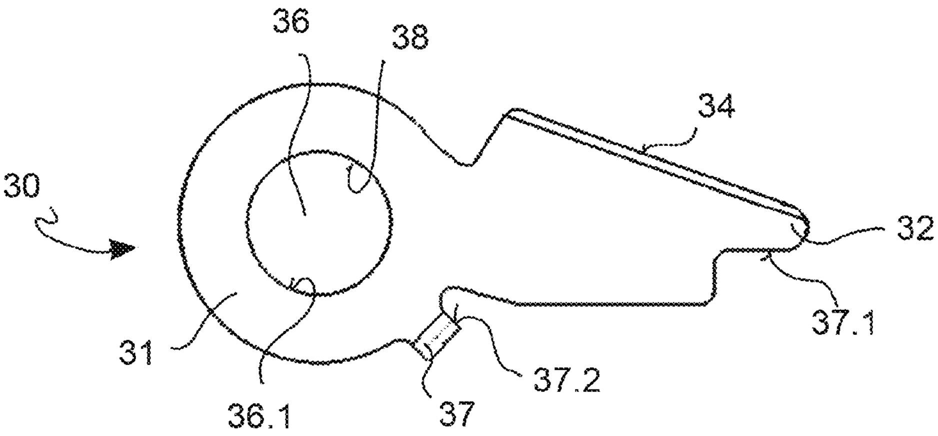
FIG. 29A shows a vertical elevation view of a blade link, according to an embodiment.

The opening drag counter-surface 37.2 and the closing drag counter-surface 37.1 of the blade link 30 can be arranged at different distances from the common rotation axis Y-Y, for example on different protrusions of the blade link 30, as shown for example in FIG. 28A. In particular with reference to FIGS. 28A, 28B and 28C, as well as FIG. 29A, the third root 31 of the blade link 30 can comprise a radial drag ear 37 folded onto the first root 11 of the first tip link 10, said drag ear 37 comprising said opening drag counter-surface 37.2 in drag contact with an opening drag surface 17.2 which is for example placed on a portion of the back D1 of the connecting portion 81 of the body of the first tip link 10.

In accordance with an embodiment, said first tip link 10 and said blade link 30, being made in separate pieces, are integral in rotation with each other in a releasable manner and the release can preferably occur only by disassembling the articulated end-effector 9.

Figure 18:
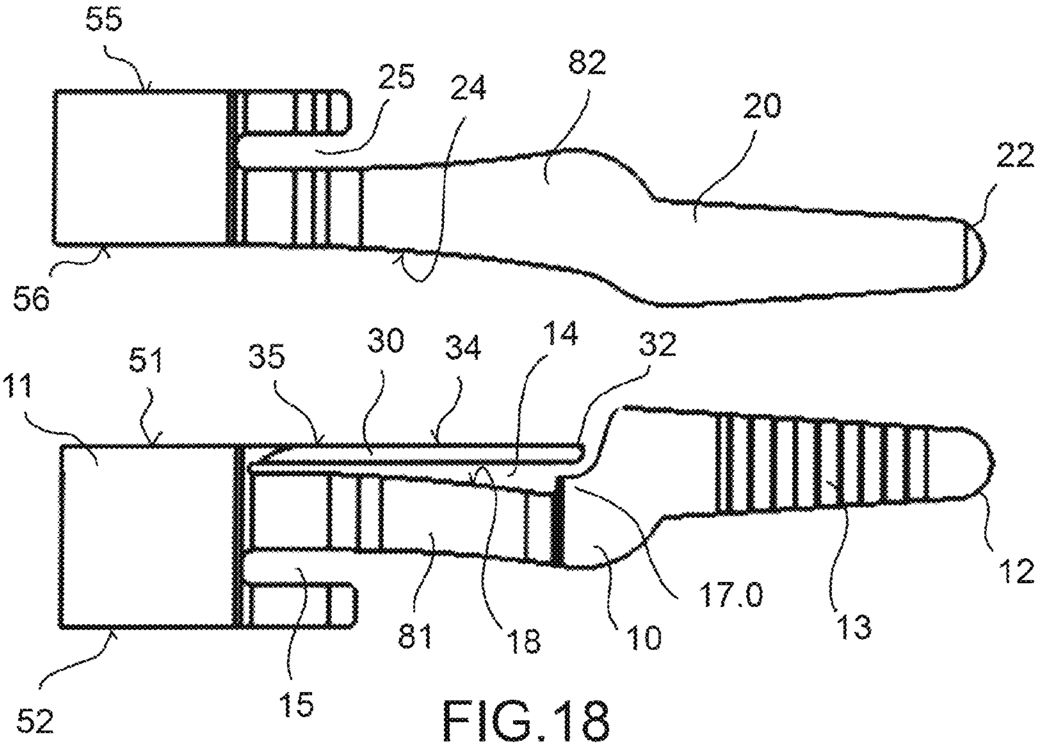
FIG. 18 shows a plan view with separate parts of a portion of an end-effector of a surgical instrument of the needle-holder/cutter type, according to an embodiment.
Figure 19:
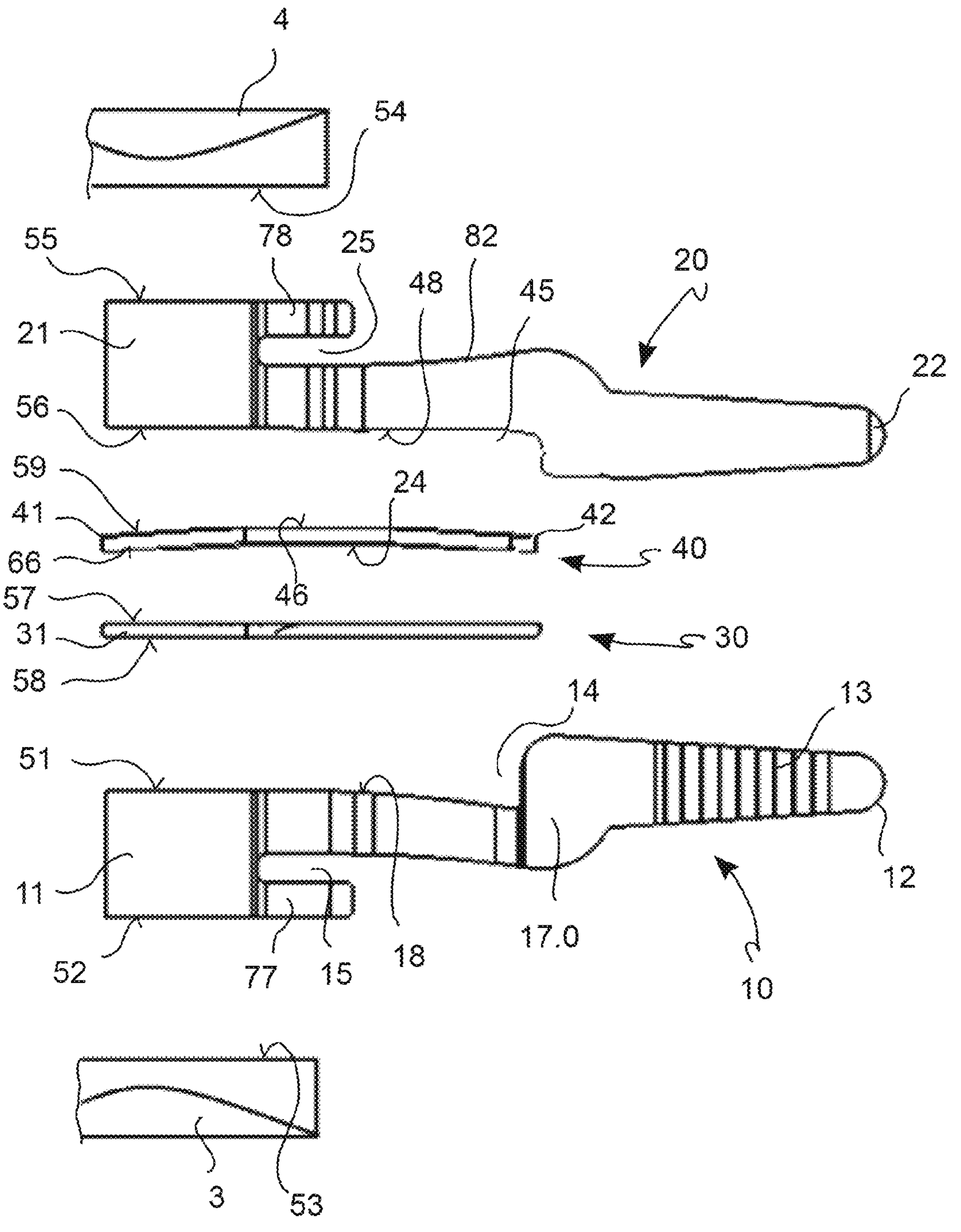
FIG. 19 shows a plan view with separate parts of end-effector of a surgical instrument of the needle-holder/cutter type, according to an embodiment.
Figure 20:
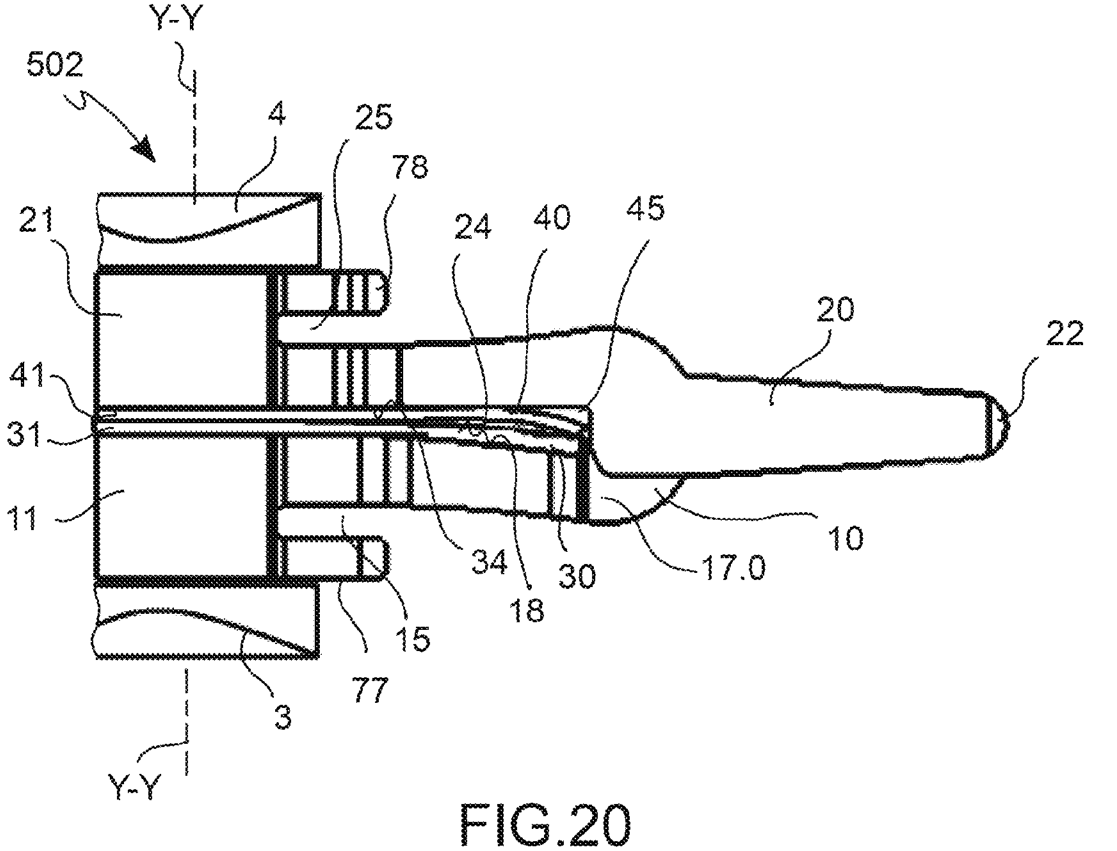
FIG. 20 shows the end-effector in FIG. 19 in an assembled and cutting configuration.

In accordance with an alternative embodiment not necessarily combinable with all the embodiments described herein, as shown in FIG. 18, for example, the blade 30 is made in a single piece with the first tip link 10, thereby defining a blade 30 having a cutting edge 34 extending longitudinally and cantilevered from the first root 11 of the first tip link 10. In particular, in this alternative, the third root 31 of the blade link 30 and the first root 11 of the first tip link 10 are made in a single piece, and the blade body having said cutting edge 34 extends cantilevered from the root of the first tip link 10 next to the connecting portion 81 of the first tip link 10. Therefore, in this alternative, the first internal contact surface 51 of the first root 11 of the first tip link 10 is in direct and intimate contact with the second internal contact surface 56 of the second root 21 of the second tip link 20, and the cutting edge 34 as well as the blade surface 35 of the blade 30 can be aligned with said first internal contact surface 51. This alternative can be combined with any embodiment of the counter-blade surface 24 described herein, for example the counter-blade surface 24 can be made in a single piece with the second tip link 20 or in a separate piece providing a counter-blade link 40.

In accordance with an embodiment, said second tip link 20 comprises a thread-stop wall 28 facing the common rotation axis Y-Y delimiting a thread-stop recess 28.1 for receiving a suture wire 6 to keep the suture wire 6 in contact with the cutting edge 34 of the blade of the blade link 30 during a cutting closure. The provision of the thread-stop wall 28 prevents the suture wire 6 from sliding distally during the cutting action beyond the distal end 32 of the blade, as an effect of the closing action.

The thread-stop wall 28 and the thread-stop recess 28.1 preferably face the gripping side P2 of the second tip link 20, for example the thread-stop wall 28 is an arched wall which has a concavity defining the recess 28.1 facing the gripping side P2 of the second tip link 20. The recess 28.1 can be made in the form of a notch provided in the body of the second tip link 20 and in such a case the thread-stop wall 28 is a wall delimiting said notch. The recess 28.1 can be made in the form of an undercut wall provided on a protrusion of the body of the second tip link 20 and in such a case the thread-stop wall 28 is an undercut wall of said protrusion facing the common rotation axis Y-Y.

In accordance with an embodiment, the thread-stop wall 28 delimits with an axially internal edge thereof the counter-blade surface 24 from the gripping side P2 of the second tip link 20. Where the counter-blade surface 24 is made in a separate piece with respect to the second tip link 20, the thread-stop wall 28 and the recess 28.1 can be formed in the body of the counter-blade link 40.

As mentioned above, in accordance with an embodiment, said second tip link 20 comprises in a single piece said counter-blade surface 24. Alternatively, as mentioned above, a counter-blade link 40 can be provided in a separate piece with respect to said second tip link 20 and integral in rotation therewith, said counter-blade link 40 comprising said counter-blade surface 24 and a fourth proximal attachment root 41 articulated in said common rotation axis Y-Y. In accordance with an embodiment, the second tip link 20 comprises an axial recess 45 forming a housing seat for the counter-blade link 40. Said axial recess 45 is preferably axially delimited by a surface 48 facing axially inwards of the second tip link 20.

In accordance with a preferred embodiment, the counter-blade link 40 is elastically deformable by bending. Thereby, when the cutting edge 34 of the blade link 30 is in mechanical interference contact with the counter-blade surface 24 of the counter-blade link 40 to exert a cutting action, the body of the counter-blade link 40 elastically bends in the axial direction as well.

The counter-blade link 40 is preferably made from an elastic sheet or strip and is pre-curved to form a curved, protruding counter-blade surface 24 having a concavity facing axially inwards, in order to elastically bend the blade link 30 during the cutting action. The provision of a counter-blade link 40 having a curved, protruding counter-blade surface 24 elastically deformable by bending allows obtaining an elastic reaction between the surface 48 facing axially inwards of the axial recess 45 of the second tip link 20 and the cutting edge 34 of the blade link 30, during the cutting action. In particular, the counter-blade link 40 comprises a resting surface 46 directed axially and opposite the counter-blade surface 24 which abuts against said surface 48 facing axially inwards of the axial recess 45 of the second tip link 20 to allow the counter-blade link 40 to provide an elastic action on the cutting edge 34 of the blade link 30 aimed at resiliently bending the blade link 30 during the cutting action.

The counter-blade link 40 can have at least some, but also all, of the features and properties described above with reference to the blade link 30. The thickness of the counter-blade link 40 can be substantially comparable to or equal to the thickness of the blade link 30, as described above. In accordance with an embodiment, the counter-blade link 40 comprises a counter-blade cutting edge 44 which is preferably arranged opposite with respect to the cutting edge 34 of the blade link 30, i.e., in other words the cutting edge of the counter-blade 44 faces the gripping side P2 of the second tip link 20. The fourth proximal attachment root 41 of the counter-blade link 40 can have at least some, but also all, of the features and properties described above with reference to the third root 31 of the blade link 30. In particular, in accordance with a preferred embodiment, said fourth root 41 of the counter-blade link 40 delimits a fourth through hole 46 for receiving said articulation pin 5. The fourth root 41 can comprise a radial cutting channel 49 misaligned with the radial cutting channel 39 of the blade link 30.

In accordance with an embodiment, to make the counter-blade link 40 and the second tip link 20 integral in rotation, a drag engagement is provided along the longitudinal extension of the counter-blade surface 24 or distally with respect thereto. Preferably, the drag engagement is obtained close to or at the distal end 42 of the counter-blade link 24.

In accordance with an embodiment, the second tip link 20 comprises a drag seat 47 having an opening drag surface 27.2 and an opposite closing drag surface 27.1 to make the blade holder link 40 integral in rotation. The drag seat 47 can be placed distally in a drag seat made as an undercut with respect to the second gripping surface 23 of the second tip link 20 to receive the distal end 42 of the counter-blade link 40. In accordance with an embodiment, said distal end 42 of the counter-blade link comprises an opening drag surface 47.2 in dragging contact with said opening drag surface 27.2 of the second tip link 20, and an opposite closing drag surface 47.1 in dragging contact with said closing drag surface 27.1.

Figure 29B:
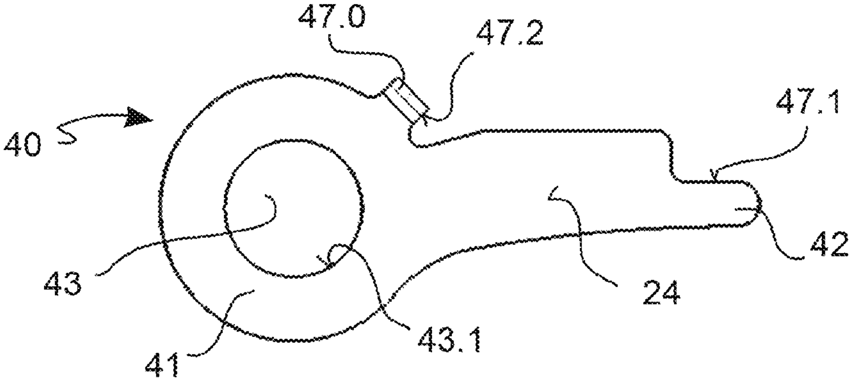
FIG. 29B shows a vertical elevation view of a counter-blade link, according to an embodiment.
Figure 29C:
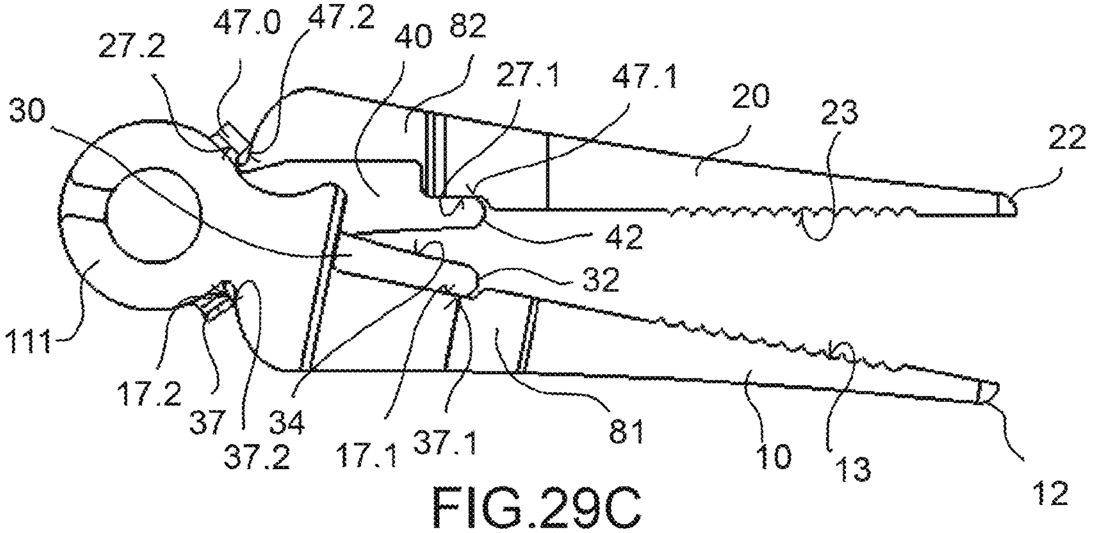
FIG. 29C shows a vertical elevation view of a portion of an end-effector of a surgical instrument of the needle-holder/cutter type comprising the blade link of FIG. 29A and the counter-blade link of FIG. 29B in an assembled configuration.
Figure 31:
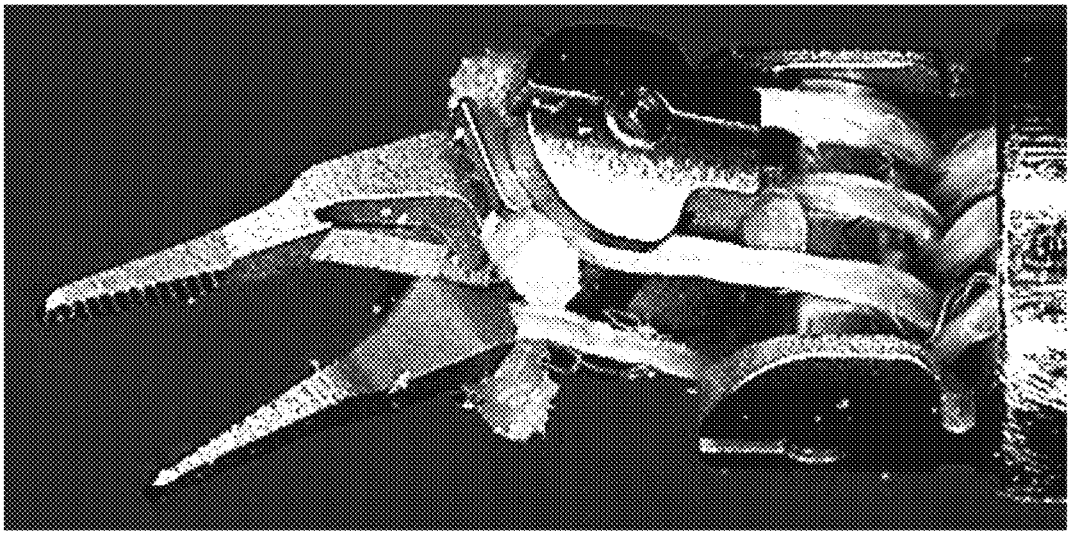
FIG. 31 is an electron microscope photographic image depicting an end-effector of a surgical instrument of the needle-driver/scissor gripper type at the distal end of a shaft, according to an embodiment.
Figure 32:
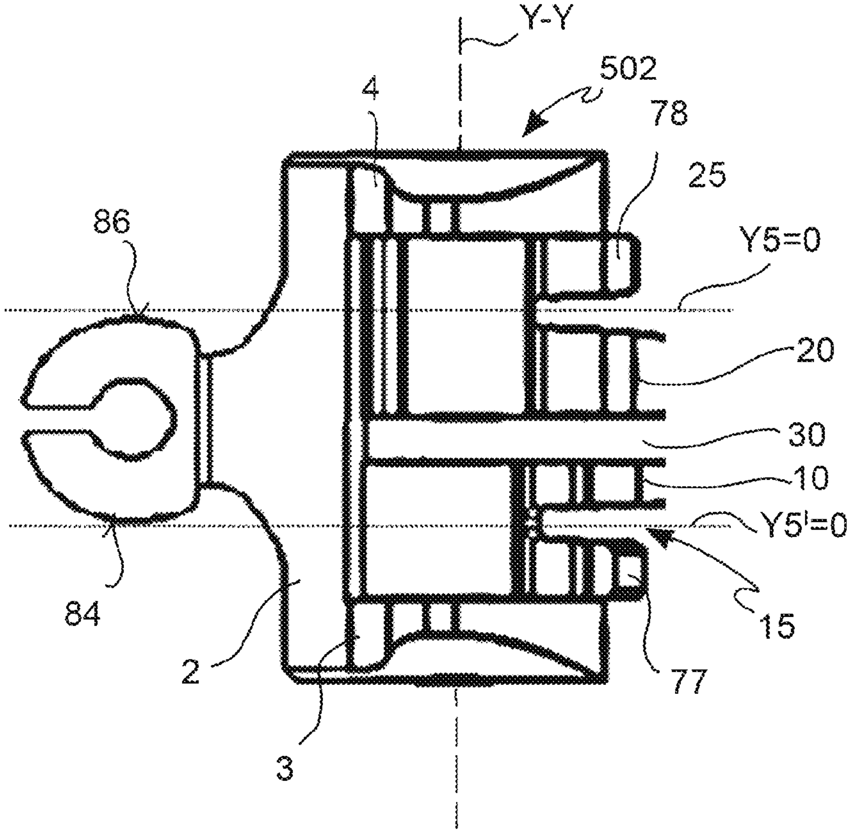
FIG. 32 is a view showing a rotational joint of a cutting joint of an articulated end-effector of a surgical instrument, according to an embodiment.

In accordance with an embodiment as shown in FIG. 29B, for example, the counter-blade link 40 comprises a radial drag ear 47.0 folded on the second root 21 of the second tip link 20, said drag ear 47.0 of the counter-blade link 40 comprising an opening drag surface 47.2 in drag contact with an opening drag surface 27.2 which is for example placed on a back portion D2 of the connecting portion 82 of the body of the second tip link 20, and in which the counter-blade link 40 further comprises a closing drag surface 47.1 placed close to the distal end 42 of the counter-blade link 40 in drag contact with a closing drag surface 27.1 of the second tip link 20.

Figure 27:
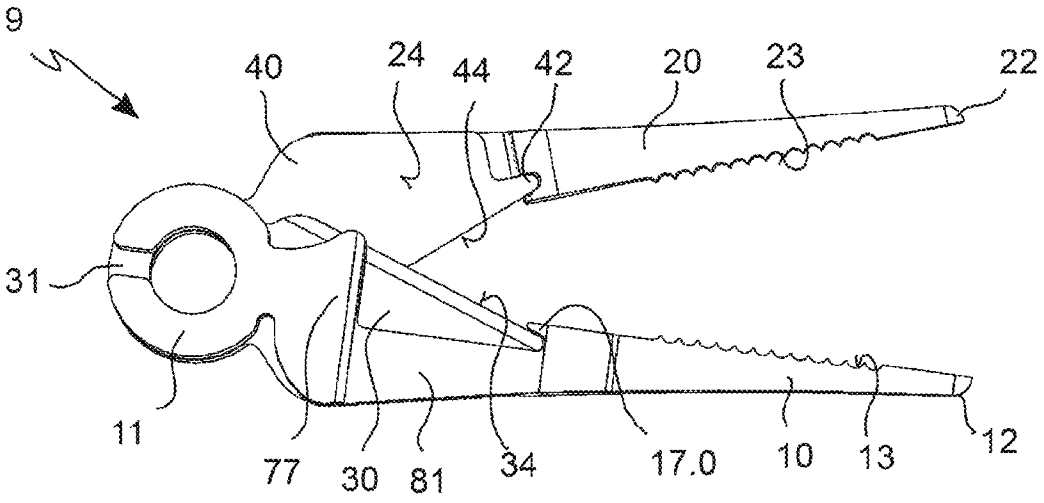
FIG. 27 shows a vertical elevation view of a portion of an end-effector of a surgical instrument of the needle-holder/cutter type, according to an embodiment.

In accordance with an embodiment as shown in FIG. 27, for example, the counter-blade cutting edge 44 can have a concave shape with respect to the opening/closing direction.

In accordance with a general embodiment, a rotational joint 502 of an articulation according to any one of the previously described embodiments is provided.

The rotational joint 502 of the cutting joint is an axially rigid coupling.

In accordance with a general embodiment, a robotic surgery system 101 is provided comprising at least one surgical instrument 1 of the needle-holder/cutter type according to any one of the embodiments described above. The robotic surgery system 101 is thus capable of performing surgical or microsurgical procedures of anastomoses and/or sutures in which a surgical instrument of the needle-holder/cutter type 1 is capable of manipulating the surgical needle and at the same time cutting the suture wire.

In accordance with an embodiment, said robotic surgery system 101 comprises two surgical instruments, at least one of which is a surgical instrument of the needle-holder/cutter type 1 according to any one of the embodiments described above and the other surgical instrument can be a surgical instrument of the needle-driver type or a surgical instrument of the dilator type, although in accordance with an embodiment both surgical instruments are surgical instruments of the needle-holder/cutter type 1.

The robotic surgery system 101 preferably comprises at least one robotic manipulator 63 and the at least one surgical instrument of the needle-holder/cutter type 1 is operatively connected to said at least one robotic manipulator 63. For example, a sterile surgical barrier (not shown), such as for example a sterile surgical cloth, is interposed between the at least one robotic manipulator 63 and the backend portion 61 of the at least one surgical instrument of the needle-holder/cutter type 1. The robotic manipulator 63 can comprise motorized actuators for stressing said actuation tendons of the degrees of freedom of pitch P, yaw Y and grip G, i.e., gripping and cutting the surgical instrument 1, and a motorized actuator for rotating the surgical instrument 1 about the shaft 7 defining a degree of freedom of roll. The robotic surgery system 101 can comprise a support portion 69 (cart or tower) for example comprising wheels or other ground contact units, and an articulated positioning arm 70, for example manually movable, i.e., passive, extending between the support portion 69 and the at least one robotic manipulator 63. In accordance with an embodiment, the robotic surgery system 101 comprises at least one master console 68 for controlling the at least one surgical instrument of the needle-holder/cutter type 1 and preferably also the respective robotic manipulator 62 according to a master-slave architecture, and preferably the robotic surgery system 101 further comprises a control unit operatively connected to the master console 68 and the robotic manipulator 63 for determining the tracking of the surgical instrument of the needle-holder/cutter type to at least one master control device 50 of the master console 68. In accordance with an embodiment, the master console 68 comprises at least one master control device 50 which is unconstrained, i.e., mechanically disconnected from the ground, and a tracking system, for example optical and/or magnetic.

By virtue of the features described above, provided either separately or in combination in particular embodiments, it is possible to meet the needs mentioned above, even conflicting, and to obtain the aforementioned advantages, and in particular:

the degree of freedom of opening/closing allows performing a gripping action of a surgical needle in a portion of the end-effector at the gripping surfaces of the first and second tip links and a cutting action of a suture wire in a proximal portion with respect to the gripping surfaces of the first and second tip links;

an extreme miniaturization of the articulated end-effector of the surgical instrument of the needle-holder/cutter type with respect to known solutions is allowed;

it is possible to stack the roots of the links between the prongs of the support structure, while avoiding the provision of elastic washers as well as adjustment screws, as well as tapping or threading machining at the level of the attachment roots, thus allowing an extreme miniaturization of the articulated end-effector;

in particular, the articulation pin 5 is unthreaded;

neither are the hole edges surfaces of the through holes of the roots of the respective links tapped, i.e., internally threaded, nor are the internal surfaces of the through holes of the prong through the prongs of the support structure;

there are no elements, such as the Belleville washer type, fitted on the articulation pin;

meanwhile, all the elasticity necessary for the cutting action is concentrated outside the roots, i.e., in the body of the blade link 30 (and in the counter-blade link when present), allowing performing a precise cutting action while creating extremely miniaturized articulated end-effectors;

in particular, for relatively high degree of freedom angles of opening/closing the blade is free, i.e., elastically unstressed, and preferably in such a configuration it is straight; in an open configuration of the degree of freedom of opening/closing the blade can overlap the rotational footprint of the protruding counter-blade i.e., overlap the rotational footprint of the second tip link (as well as of the counter-blade link, when present); in an open configuration of the degree of freedom of opening/closing the blade is spaced with respect to the connecting portion of the first tip link, and in particular is spaced from the surface 18 facing axially inwards of the first tip link, thereby defining a deformation seat 14 for the blade;

as the opening angle of the degree of freedom of opening/closing closes, the blade is elastically bent, elastically pushing against the counter-blade 24; in a closed configuration of the degree of freedom of opening/closing the blade can be interposed between the connecting portions of the first and second tip links and in contact therewith (or in contact with the counter-blade link, when present and in turn interposed between the blade and the body of the second tip link);

since the elasticity necessary for the cutting action is concentrated distally in the blade link body with respect to the roots, a deformation seat can be provided which receives the relatively high axial bending of the blade;

the roots stacked in a pack between the prongs provide a reaction to the elastic bending deformation of the blade, avoiding axial sliding on the pin, thus allowing a precise and effective cutting action of the cutting edge 34 even at high opening angles, i.e., the cutting edge is able to push on the counter-blade even proximally, at the level of the roots, next to the articulation pin;

while the first tip link and the second tip link are directly actuated by actuation tendons, the blade link and the counter-blade link, when present, are dragged in rotation by the first tip link and by the second tip link;

the provision of such a third root 31 of the blade link 30 allows the blade link 30 to be firmly anchored to the common rotation axis Y-Y when in operating conditions, for example during the cutting action, as well as the provision of such a drag seat 17 to make the blade link 30 integral in rotation with the first tip link 10 placed close to the distal end 32 of the blade link allows the blade link 30 to be firmly anchored while receiving the axial deformation of the distal end 32 of the blade link (the same applies to the counter-blade link 40, when present), allowing extreme miniaturization of the articulated end-effector without imposing positioning and cutting inaccuracies, and meanwhile allows a robust and reliable solution to be provided which avoids the risk of loss of the blade link i.e., the detachment thereof when in operating conditions;

the provision of through holes of all the coaxial roots receiving with contact the articulation pin allows avoiding unintentional relative rotations between the roots, providing positioning certainty of the cutting edge 34 of the blade link 30 with respect to the counter-blade surface 24, as well as to the gripping surfaces 13, 23, when in operating conditions, thus allowing an extreme miniaturization of the articulated end-effector, since small rotational movements at the level of the root, i.e., next to the common rotation axis would impose relatively large cutting inaccuracies;

in addition, the hole 36 of the blade link exerts with the proximal edge thereof pushing on the pin a reaction to the friction between the blade and the counter-blade during the cutting action, helping obtain a precise cutting action;

the cutting edge of the blade link can be made straight i.e., without concavity, facilitating production in series, for example starting from a single band or strip;

the integral rotation of the blade link and the counter-blade link, where present, with the free ends allows performing the cutting action in various orientations of the degree of freedom of yaw, so as to be able to reproduce the orientation of a surgeon's hands, thus being of a marked intuitiveness, as well as easier to view, for example, under a microscope;

the provision of an abutment of the closing stroke end distant from the articulation pin and distal with respect thereto allows a high precision in closing and at the same time does not occupy the proximal area of the support fork, favoring an extreme miniaturization;

the termination seats of the tendons and the ruled pulley surfaces made in a single piece with the respective links favor miniaturization, helping keep the number of pieces small and the articulated end-effector compact;

in case of a surgical instrument of the needle-driver/scissor type, interposing the blade between the tip links allows it to be concealed with a closed end-effector allowing, for example, to wrap the suture wire around the tip links without damaging it;

the provision of a single drag engagement portion in rotation between two links allows minimizing the drag clearance, favoring miniaturization;

the rotational joint 502 defining the common rotation axis Y-Y can be a hinge.

It is well understood that the combination of features, structures or functions disclosed in one or more of the appended claims forms an integral part of the present description.

In order to meet specific, contingent needs, those skilled in the art can make several changes and adaptations to the above-described embodiments and can replace elements with other functionally equivalent ones, without departing from the scope of the appended claims.

LIST OF REFERENCE SIGNS

| | |
|---|---|
| 1 | Needle-holder/cutter type surgical instrument |
| 2 | Support link |
| 3 | First support structure prong |
| 4 | Second support structure prong |
| 5 | Pivot pin or articulation pin |
| 6 | Suture thread or suture wire |
| 7 | Surgical instrument shaft |
| 8 | Distal shaft end |
| 9 | Articulated end-effector, or articulated terminal |
| 10 | First tip link or blade holder link |
| 11 | First proximal attachment root of the first tip link, or attachment root of the first tip link |
| 12 | First distal free end of the first tip link, or free end of the first tip link |
| 13 | First gripping surface of the first tip link, or gripping surface of the first tip link |
| 14 | Deformation seat for the first tip link blade |
| 15 | First termination seat of the first link, or first link termination seat |
| 16 | First through hole of the first root of the first tip link, or root hole of the first tip link |
| 16.1 | Hole edge of the first hole of the first root |
| 17 | First tip link drag seat |
| 17.0 | First tip link drag tooth |
| 17.1 | First tip link closing drag surface |
| 17.2 | First tip link opening drag surface |
| 18 | First tip link surface facing axially inwards |
| 19 | Cutting channel of the first root of the first tip link |
| 20 | Second tip link or reaction link |
| 21 | Second proximal attachment root of the second tip link, or attachment root of the second tip link |
| 22 | Second distal free end of the second tip link, or free end of the second tip link |
| 23 | Second gripping surface of the second tip link, or gripping surface of the second tip link |
| 24 | Counter-blade surface |
| 25 | Second termination seat of the second link, or second link termination seat |
| 26 | Second through hole of the second root of the second tip link, or root hole of the second tip link |
| 26.1 | Hole edge of the second hole of the second root |
| 28 | Thread-stop wall |
| 28.1 | Thread-stop wall recess |
| 29 | Cutting channel of the second root of the second tip link |
| 30 | Blade link, or blade |
| 31 | Third proximal attachment root of the blade link, or blade link root |
| 32 | Distal blade link end |
| 33 | Transverse blade link bridge |
| 34 | Blade link cutting edge |
| 35 | Blade surface facing axially inwards of the blade link |
| 36 | Third through hole of the third root of the blade link, or root hole of the blade link |
| 36.1 | Hole edge of the third hole of the third root |
| 37 | Third blade link drag ear |
| 37.1 | Blade link closing drag counter-surface |
| 37.2 | Blade link opening drag counter-surface |
| 38 | Arc surface of the hole edge of the third root of the blade link |
| 39 | Cutting channel of the third root of the blade link |
| 40 | Counter-blade link |
| 41 | Fourth proximal attachment root of the counter-blade link, or fourth root of the counter-blade link |
| 42 | Distal counter-blade link end |
| 43 | Through hole of the counter-blade link, or fourth hole of the fourth root of the counter-blade link |
| 43.1 | Hole edge of the through hole of the counter-blade link root |
| 44 | Counter-blade cutting edge |
| 45 | Axial recess of the counter-blade link |
| 46 | Counter-blade link support surface |
| 47 | Second tip link drag seat |

-continued

| | |
|---|---|
| 47.0 | Counter-blade link drag ear |
| 47.1 | Counter-blade link closing drag counter-surface |
| 47.2 | Counter-blade link opening drag counter-surface |
| 48 | Second tip link surface facing axially inwards |
| 49 | Counter-blade link cutting channel |
| 50 | Master control device |
| 51 | First internal contact surface of the first root of the first tip link, or internal contact surface of the first tip link root |
| 52 | First external contact surface of the first root of the first tip link, or external contact surface of the first tip link root |
| 53 | First internal contact surface of the first prong of the support link, or internal contact surface of the first prong of the support link |
| 54 | Second internal contact surface of the second prong of the support link, or internal contact surface of the second prong of the support link |
| 55 | Second external contact surface of the second root of the second tip link, or external contact surface of the second tip link root |
| 56 | Second internal contact surface of the second root of the second tip link, or internal contact surface of the second tip link root |
| 57 | Contact surface of the third root of the blade link facing the counter blade, or second contact surface of the third root of the blade link |
| 58 | First contact surface of the third root of the blade link |
| 59 | Contact surface of the fourth root of the counter-blade link |
| 60 | End-effector link for the connection with the shaft, or connection link |
| 60.1 | First prong of the connection link |
| 60.2 | Second prong of the connection link |
| 61 | Surgical instrument backend portion, or proximal interface portion |
| 62 | Proximal shaft end |
| 63 | Robotic manipulator |
| 64 | Shaft fixing device |
| 66 | Contact surface of the fourth root of the counter-blade link facing the blade |
| 67 | Third termination seat of the support link |
| 68 | Master console |
| 69 | Support portion, or cart, or tower, of the robotic system |
| 70 | Articulated positioning arm of the robotic system |
| 71 | First tip link opening actuation tendon |
| 72 | First tip link closing actuation tendon |
| 73 | Second tip link opening actuation tendon |
| 74 | Second tip link closing actuation tendon |
| 75 | Support link actuation tendon |
| 76 | Support link actuation counter-tendon |
| 77 | Cantilevered drag leg of the first termination seat of the first tip link |
| 78 | Cantilevered drag leg of the second termination seat of the second tip link |
| 79 | Ruled pulley surface of the first tip link |
| 80 | Ruled pulley surface of the second tip link |
| 81 | First tip link connecting portion between the first root and the first gripping surface |
| 82 | Second tip link connecting portion between the first root and the first gripping surface |
| 70 | Tendon termination |
| 84 | Convex ruled surface of the support link |
| 85 | Convex ruled sliding surface of the connection link |
| 86 | Opposite convex ruled surface of the support link |
| 87 | Opposite convex ruled sliding surface of the connection link |
| 101 | Robotic surgery system |
| 165 | Prong hole |
| 502 | Rotational joint of the cutting joint, or distal rotational joint |
| 509 | Proximal rotational joint |
| X-X | Longitudinal shaft axis |
| Y-Y | Common rotation axis, or common distal rotation axis or common yaw rotation axis |
| P-P | Common proximal rotation axis, or common pitch rotation axis |
| Y | Degree of freedom of yaw |
| P | Degree of freedom of pitch |
| G | Opening/closing direction, or degree of freedom of grip |
| R | Degree of freedom of roll |
| POC | At least one point of contact between blade and counter-blade |
| D1 | First tip link back side |
| P1 | First tip link gripping side |
| D2 | Second tip link back side |
| P2 | Second tip link gripping side |

The invention claimed is:

1. A needle-holder/cutter type surgical instrument for a robotic surgery system comprising an articulated end-effector comprising:

a support structure comprising two prongs;

a first tip link having an elongated body comprising in a single piece a first proximal attachment root, a first distal free end and a first gripping surface intermediate the first proximal attachment root and the first distal free end;

a second tip link having an elongated body comprising in a single piece a second proximal attachment root, a second distal free end, and a second gripping surface intermediate the second proximal attachment root and the second distal free end;

a blade link comprising in a single piece a third proximal attachment root, an elastically deformable bending body and a cutting edge;

wherein:

the support structure, the first tip link, the second tip link and the blade link are separate pieces articulated to one another in a common rotation axis defining an axial direction coincident with or parallel to the common rotation axis;

the blade link is integral in rotation with said first tip link; and wherein:

the first root of the first tip link, the second root of the second tip link and the third root of the blade link are axially proximate one another;

the first root of the first tip link, the second root of the second tip link and the third root of the blade link are articulated with respect to the prongs of the support structure about said common rotation axis defining a degree of freedom of orientation between the support structure and the group formed by said first tip link, said second link tip and said blade link;

the first root of the first tip link and the second root of the second tip link are mutually articulated about said common rotation axis, defining a relative degree of freedom of opening/closing between the second tip link and a group formed by the first tip link and the blade link; and wherein the articulated end-effector comprises:

a counter-blade surface which is integral in rotation with the second tip link;

said counter-blade surface is adapted to abut against said cutting edge of the blade link, elastically bending said blade link axially, so that said cutting edge of the blade link and said counter-blade surface reach a mechanical interference contact condition to exert a cutting action.

2. The surgical instrument according to claim 1, wherein a group formed by said first root of the first tip link, and said second root of the second tip link, and said third root of the blade link is jointly interposed between said two prongs of the support structure and in direct and intimate contact with said two prongs of the support structure.

3. The surgical instrument according to claim 1, wherein the third root of the blade link is axially interposed between said first root of the first tip link and said second root of the second tip link and in direct and intimate contact with said first root of the first tip link and said second root of the second tip link.

4. The surgical instrument according to claim 1, wherein said first, second and third roots and said prongs comprise respective axially facing contact surfaces which are all parallel to one another.

5. The surgical instrument according to claim 1, wherein said first root of the first tip link comprises a first through hole, and said second root of the second tip link comprises a second through hole, and said third root of the blade link comprises a third through hole, wherein said first through hole of the first root, and said second through hole of the second root, and said third through hole of the third root are all circular through holes and coaxial to said common rotation axis and receive a single articulation pin extending in an axial direction from a first prong of the support structure to a second prong of the support structure.

6. The surgical instrument according to claim 5, wherein said third through hole of the third root of the blade link has a hole edge in direct and intimate contact with an articulation pin for an entire extension of the hole edge.

7. The surgical instrument according to claim 1, wherein said counter-blade surface integral in rotation with said second tip link axially protrudes for bending the blade link;

and wherein preferably said counter-blade surface is a curved protruding surface having concavity facing axially internally.

8. The surgical instrument according to claim 1, wherein the body of the blade link is substantially planar when in a non-deformed configuration and lying on a definable lying plane;

and wherein an axially facing blade surface of the blade link is parallel and aligned with a contact surface of the third root of the blade link in direct and intimate contact with the second root of the second tip link.

9. The surgical instrument according to claim 1, wherein said cutting edge of the blade link is interposed between, and proximate: a first connecting portion extending between the first root and the first gripping surface and a second connecting portion between the second root and the second gripping surface, respectively of the body of the first tip link and the body of the second tip link.

10. The surgical instrument according to claim 1, wherein said first tip link comprises an axial deformation seat extending axially to receive the elastic bending of the blade of the blade link during the cutting action;

and wherein the axial deformation seat is axially delimited by a surface facing axially inwards of the first tip link which is parallel to the counter-blade surface.

11. The surgical instrument according to claim 1, wherein said second tip link comprises a thread-stop wall, facing a gripping side of the body of the second tip link, delimiting a recess to receive a suture wire, to keep the suture wire in contact with the cutting edge of the blade of the blade link during a cutting closure.

12. The surgical instrument according to claim 1, wherein said articulated end-effector comprises:

three pieces, comprising: said first tip link, said second tip link and said blade link, wherein said three pieces are articulated in said common axis with respect to said support structure comprising said two prongs, a further piece comprising an articulation pin defining said common rotation axis;

or wherein said articulated end-effector consists of exactly four pieces articulated in said common axis, comprising: a support link, said first tip link, said second tip link and said blade link, the prongs belonging to said support link, the further piece comprising the articulation pin defining said common rotation axis, an additional piece comprising a proximal articulation pin defining a proximal rotation axis for the support link.

13. The surgical instrument according to claim 1, wherein the first root of the first tip link comprises in a single piece at least a first termination seat for at least one actuation tendon of the first tip link about said common rotation axis, and wherein the second root of the second tip link comprises in a single piece at least a second termination seat for at least one actuation tendon of the second tip link about said common rotation axis;

and wherein said support structure comprising said two prongs belongs to a support link which is articulated with respect to a distal end of a shaft about a proximal rotation axis and comprises in a single piece at least a third termination seat for at least one actuation tendon of the support link about said rotation proximal axis.

14. A robotic surgery system comprising at least one needle-holder/cutter type surgical instrument according to claim 1.

* * * * *